(12) United States Patent
Berreklouw

(10) Patent No.: US 8,142,496 B2
(45) Date of Patent: Mar. 27, 2012

(54) FIXING DEVICE, IN PARTICULAR FOR FIXING TO VASCULAR WALL TISSUE

(75) Inventor: Eric Berreklouw, Son (NL)

(73) Assignee: Daidalos Solutions B.V., Son (NL)

( * ) Notice: Subject to any disclaimer, the term of this patent is extended or adjusted under 35 U.S.C. 154(b) by 265 days.

(21) Appl. No.: 12/403,495

(22) Filed: Mar. 13, 2009

(65) Prior Publication Data
US 2009/0234446 A1    Sep. 17, 2009

Related U.S. Application Data

(62) Division of application No. 10/822,682, filed on Apr. 13, 2004, now Pat. No. 7,524,330, which is a division of application No. 09/979,668, filed as application No. PCT/NL00/00265 on Apr. 25, 2000, now Pat. No. 6,790,229.

(30) Foreign Application Priority Data

May 25, 1999  (NL) .................................. 1012150
Dec. 23, 1999  (NL) .................................. 1013933

(51) Int. Cl.
    *A61F 2/24* (2006.01)
(52) U.S. Cl. ...................... 623/2.37; 623/2.36
(58) Field of Classification Search ................. 623/1.26, 623/2.1–2.42
    See application file for complete search history.

(56) References Cited

U.S. PATENT DOCUMENTS

| | | | |
|---|---|---|---|
| 3,143,742 A | 8/1964 | Cromie | |
| 3,371,352 A | 3/1968 | Siposs et al. | |
| 3,574,865 A | 4/1971 | Hamaker | |
| 3,686,740 A | 8/1972 | Shiley | |
| 4,182,446 A | 1/1980 | Penny | |
| 4,506,394 A | 3/1985 | Bedard | |
| 5,370,685 A | 12/1994 | Stevens | |
| 5,397,355 A | 3/1995 | Marin et al. | |
| 5,478,354 A | 12/1995 | Tovey et al. | |
| 5,535,549 A * | 7/1996 | Weder et al. ...................... 47/72 |
| 5,593,424 A * | 1/1997 | Northrup, III ................ 606/232 |
| 5,695,504 A | 12/1997 | Gifford, III et al. | |
| 5,716,370 A | 2/1998 | Williamson, IV et al. | |
| 5,797,933 A | 8/1998 | Snow et al. | |
| 5,855,601 A | 1/1999 | Bessler et al. | |
| 5,868,763 A | 2/1999 | Spence et al. | |
| 5,957,949 A | 9/1999 | Leonhardt et al. | |
| 5,984,959 A | 11/1999 | Robertson et al. | |
| 6,106,550 A | 8/2000 | Magovern et al. | |
| 6,312,465 B1 | 11/2001 | Griffin et al. | |
| 6,458,153 B1 | 10/2002 | Bailey et al. | |

(Continued)

FOREIGN PATENT DOCUMENTS

| | | |
|---|---|---|
| EP | 0 145 166 B2 | 6/1995 |
| WO | 97/28745 | 8/1997 |
| WO | 98/07399 | 2/1998 |

(Continued)

*Primary Examiner* — David H Willse
*Assistant Examiner* — Javier Blanco
(74) *Attorney, Agent, or Firm* — Young & Thompson

(57) ABSTRACT

A device for narrowing the passage through surrounding vascular wall tissue, such as a ring prosthesis for reducing the size of the passage of a heart valve, includes a ring shaped element which is elastically contractile under influence of a resilient force for contracting the ring shaped element from an expanded, wide condition to a narrow condition to narrow the passage. A method of narrowing the passage through surrounding vascular wall tissue using such a device is also disclosed.

18 Claims, 21 Drawing Sheets

U.S. PATENT DOCUMENTS

| | | |
|---|---|---|
| 6,503,272 B2 | 1/2003 | Duerig et al. |
| 6,524,322 B1 | 2/2003 | Berreklouw |
| 6,629,534 B1 * | 10/2003 | Dell et al. .................. 128/898 |
| 6,660,015 B1 | 12/2003 | Berg et al. |
| 7,147,663 B1 | 12/2006 | Berg et al. |
| 2002/0032481 A1 | 3/2002 | Gabbay |

FOREIGN PATENT DOCUMENTS

| | | |
|---|---|---|
| WO | 98/19634 | 5/1998 |
| WO | 99/15112 | 4/1999 |
| WO | 99/18887 | 4/1999 |
| WO | 99/37218 | 7/1999 |
| WO | 99/52481 | 10/1999 |

* cited by examiner

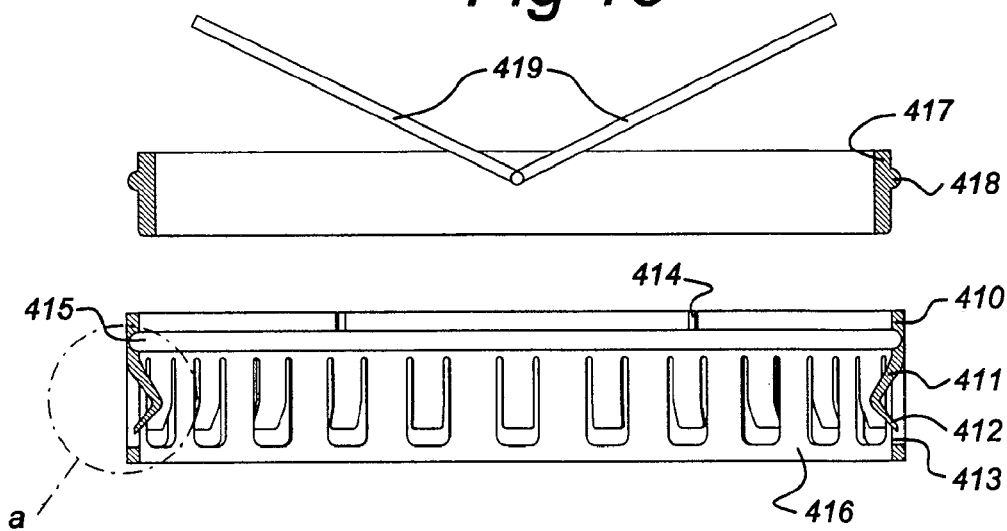
*Fig 15*
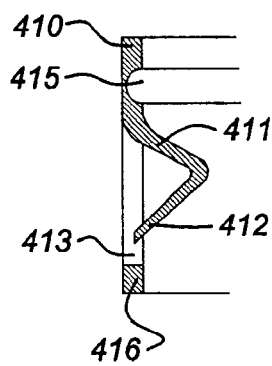
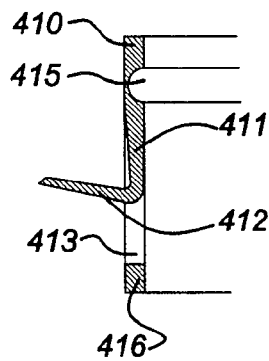
*Fig 15A*  *Fig 15B*
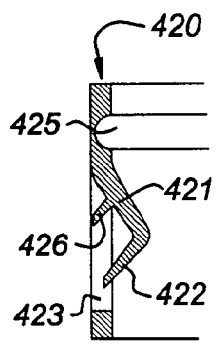
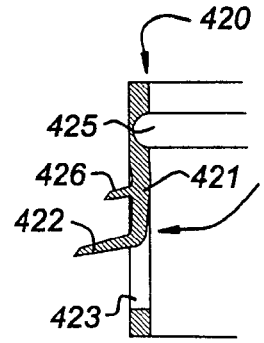
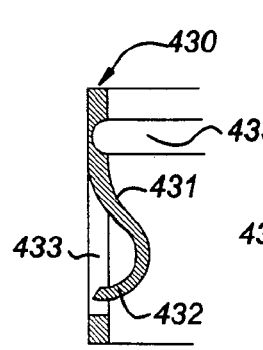
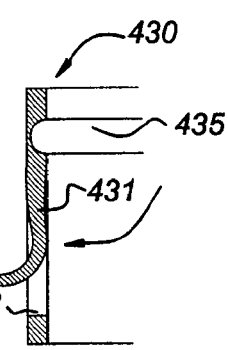
*Fig 16A*  *Fig 16B*  *Fig 17A*  *Fig 17B*

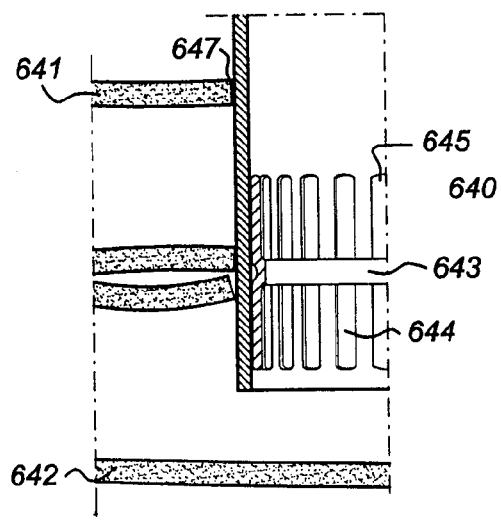
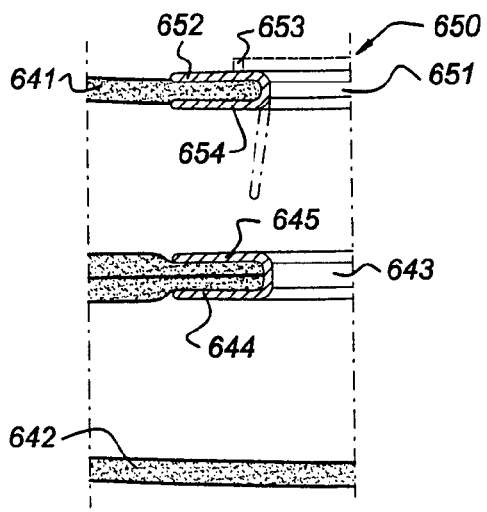
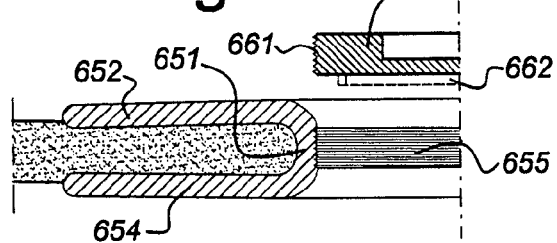
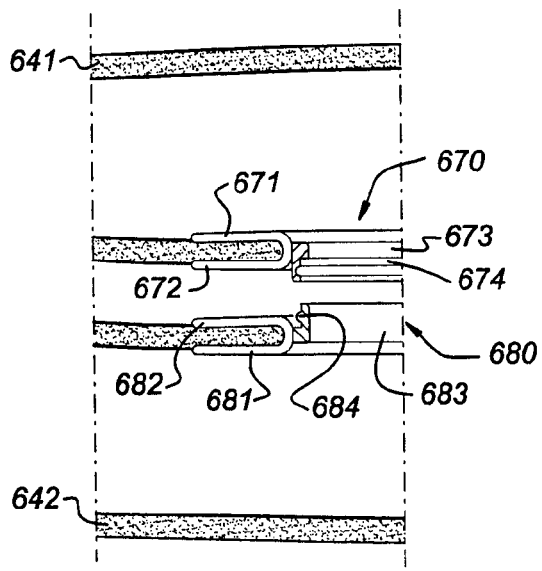
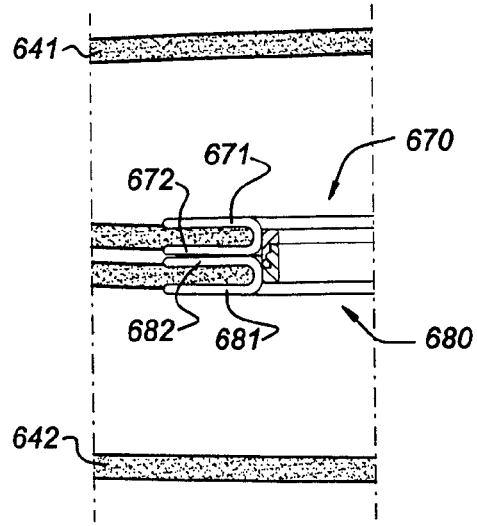

FIXING DEVICE, IN PARTICULAR FOR FIXING TO VASCULAR WALL TISSUE

CROSS REFERENCE TO RELATED APPLICATIONS

This application is a division of application Ser. No. 10/822,682 filed on Apr. 13, 2004, now U.S. Pat. No. 7,524,330; which is a division of application Ser. No. 09/979,688 filed on Mar. 8, 2002, now U.S. Pat. No. 6,790,229; which is the 35 U.S.C. 371 national stage of International application PCT/NL00/00265 filed on Apr. 25, 2000; which claimed priority to Netherlands application 1012150 and 1013933 filed May 25, 1999 and Dec. 23, 1999, respectively. The entire contents of each of the above-identified applications are hereby incorporated by reference.

INTRODUCTION

The present application is subdivided into 16 sections, i.e.: Sections X.Y, where X=1, 2, 3 or 4 and Y=1, 2, 3 or 4.

The sections where X=1 are sections relating to the preamble to the description; the sections where X=2 are sections relating to listing of the figures; the sections where X=3 are sections relating to the description of the figures; and the sections where X=4 are sections relating to preferred features (clauses).

The sections where Y=1, i.e. Sections 1.1, 2.1, 3.1 and 4.1 and associated FIGS. 1-14 have been taken as a whole from NL-A 1 012 150 with date of filing 25, May 1999. Section 1.1 is the preamble to the description of NL-A 1 012 150, Section 2.1 is the list of figures in NL-A 1 012 150; Section 3.1 is the description of the figures in NL-A 1 012 150 and Section 1.4 contains the claims of NL-A 1 012 150. It should be clear that Sections 1.1, 2.1, 3.1, 4.1 and the associated FIGS. 1-14 can in the future be split off in isolation from the present application as an individual application without any problem. It is not precluded that these sections will be supplemented from other sections when they are split off, as will be clear from the remainder of the application.

The sections where Y=2, i.e. Sections 1.2, 2.2, 3.2 and 4.2 and associated FIGS. 15-25 have been taken as a whole from NL-A 1 013 933 with date of filing 23, Dec. 1999. However, the figure numbers and reference numerals have been adjusted to prevent duplication with FIGS. 1-14 from NL-A 1 012 150. It should once again be clear that Sections 1.2, 2.2, 3.2, 4.2 and the associated FIGS. 15-25 can in the future be split off from the present application as an individual, isolated application, without any problem. It should also be clear from the remainder of this application that material from other sections of this application could be added hereto.

Sections 1.3, 2.3, 3.3, 4.3 and the associated FIGS. 25-32 relate to a particular embodiment disclosed in NL 1 012 150 (that as such is identical to the content of Sections 1.1, 2.1, 3.1, 4.1 and associated FIGS. 1-14) and further developments thereof. It should once again be clear that Sections 1.3, 2.3, 3.3 and 4.3 and the associated FIGS. 26-32 can in the future be split off from the present application as an individual, isolated application without any problem and that this could also be done in combination with the material from Sections 1.1, 2.1, 3.1, 4.1 and associated FIGS. 1-14. It should also be clear from the remainder of this application that material from other sections of this application could be added hereto.

Sections 1.4, 2.4, 3.4 and 4.4 relate to a number of inventions, such as, inter alia, more detailed embodiments or particular embodiments of the subjects of Sections 1.1, 2.1, 3.1, 4.1 and 1.2, 2.2, 3.2 and 4.2. Various aspects from Sections 1.4, 2.4, 3.4 and 4.4 and associated figures, on their own or in combination with material from other sections and figures, could also lead to split-off applications in the future.

Where reference is made below to Section X.1, this is intended to be a reference to Sections 1.1, 2.1, 3.1 and 4.1 and the associated figures. Where reference is made below to Section X.2, this is intended to be a reference to Sections 1.2, 2.2, 3.2, 4.2 and the associated figures. Where reference is made below to Section X.3, this is intended to be a reference to Sections 1.3, 2.3, 3.3, 4.3 and the associated figures. Where reference is made below to Section X.4, this is intended to be a reference to Sections 1.4, 2.4, 3.4, 4.4 and the associated figures.

Where the term "first, second, third embodiment and/or first, second, third, etc. aspect" or "invention" is used in a Section X.1, X.2, X.3 or X.4 in the present application, this must be read as relating to the relevant Section X.1, X.2, X.3 or X.4. It is thus possible, for example, for mention to be made of a first embodiment in Section 3.3 and for this to be a different embodiment from a first embodiment mentioned in Section 3.4.

In all sections of this application a portal fixing device is understood to be a device which is fixed to a vascular wall provided with a passage and is positioned around said passage in order to feed through said passage, for example, a cannula or other surgical or medical instrument or vascular fixing device or implant, such as valve or ring fixing device, or the obturator prosthesis fixing device to be mentioned below. The opening delimited by the tubular element of such a portal fixing device can be (temporarily) fully open, but can also be occluded by a (temporary) membrane, sphincter or valve mechanism. Such a portal fixing device can also serve as a coupling piece for a cannula or a working conduit, which may or may not be provided with said membranes, sphincters or valves. In the case of the last-mentioned applications, the portal fixing device can first be joined to the vascular tissue or element, after which the portal fixing device is joined to the cannula or the working conduit. It is also possible for the portal fixing device already to be integrated with the cannula or working conduit, so that only the join to the tissue has to take place. After removal of the cannula, medical or surgical instrument, implant, working conduit, etc. via or from the portal fixing device, the portal can be closed off by means of a cap. Such a cap can be made of or covered by anticoagulant material, such as carbon, carbon coating, urethane, urethane coating, heparin, heparin-like materials, but also by vascular tissue or pericardium, which may or may not be from the patient him/herself, or vascular prosthesis materials such as, for example, Dacron or Teflon. That side of the cap which can come into contact with the blood can also consist of a network structure, which is optionally coated with absorbable material such as, for example, PDS, to promote the growth of endothelial cells.

In all sections of this application an obturator prosthesis fixing device is understood to be a device for fixing an obturator prosthesis, optionally the entire obturator prosthesis itself, which can be used to close one or more holes or cavities in blood vessels or organs, such as, for example, in the case of an atrium or ventricle septum defect, rupture of the ventricle septum or aorta, true or false aneurysms, fistulas, etc. It is optionally conceivable with this arrangement for the tubular element already to be closed on the inside from the start and, for example, to assume the form of a closed disc. The materials which can be used for this will consist of the same materials or coatings as mentioned above for the cap for closing off the portal fixing device, in any event on the side or sides which can come into contact with blood.

Where STS anastomosis is mentioned in any section of this application, this refers to a so-called side-to-side anastomosis.

Where ETS anastomosis is mentioned in any section of this application, this refers to a so-called end-to-side anastomosis.

Where ETE anastomosis is mentioned in any section of this application, this refers to a so-called end-to-end anastomosis.

Wherever tube-like or tubular is mentioned in any section of this application it will be clear that this can also be understood to mean tube-like or tubular elements which are short in the axial direction, or ring-like or annular elements.

It is pointed out that where reference is made in any section to inner flange, outer flange, bottom flange, top flange, flange segments, etc. said flanges can always be either flanges which extend uninterrupted or flanges which extend with interruptions (which then are thus made up of flange sections with gaps between them).

SECTION 1.1

The present invention relates to a cardiac prosthesis fixing device comprising a tubular element which can be accommodated within a valve annulus of a heart and is provided with a bottom flange and a top flange, the bottom and top flanges extending in the peripheral direction of the tubular element, and the bottom and top flanges having a first position in which they extend outwards from the tubular element in order to be able to accommodate the valve annulus between them.

A cardiac prosthesis fixing device of this type is disclosed in U.S. Pat. No. 3,143,742 and in U.S. Pat. No. 3,574,865.

U.S. Pat. No. 3,143,742 discloses an inner ring 3, provided with external screw thread, and two rigid flanges provided with corresponding internal screw thread. By screwing the flanges over the inner ring the flanges can be turned towards one another in order to clamp the annulus in the vertical direction. Arc-shaped clasps are also provided between the flanges, the points of which clasps are driven outwards as the flanges are turned towards one another, in order to pierce tissue close to the valve annulus for fixing.

U.S. Pat. No. 3,574,865 discloses two flanges which can be joined to one another via a snap-fit joint in order to enclose tissue between them. With this arrangement the snap-fit joint is obtained by pressing an annular section, which widens towards the outside and has been formed as an integral whole with the one flange, into an annular recess, which widens towards the outside, in the other flange. In addition, pins, which extend in the direction from the one flange to the other flange and which, when the flanges are snapped together, pierce the tissue to be accommodated between the flanges, are also provided for fixing.

When fitting a valve prosthesis to replace a natural heart valve, in general the natural so-called valve cusps are cut away, after which the natural valve annulus remains behind at the location of the original valve. The natural valve annulus is a ligament on the inside of the blood vessel which extends in the peripheral direction of the blood vessel and forms a local constriction in the blood vessel. A valve prosthesis is frequently attached to this valve annulus. Notwithstanding what is known from the abovementioned U.S. Pat. Nos. 3,143,742 and 3,574,865, general practice is that a so-called suture ring made of textile material consisting of synthetic fibres (usually Dacron or Teflon) is attached to the valve annulus by suturing. A second annular, rotatable housing containing the valve cusps has already been located in this suture ring during production. In this context the valve prosthesis can be entirely synthetic, but can also be an animal or human donor prosthesis. Fixing the suture ring in place, referred to as suturing in, is a time-consuming activity which on average takes 30 to 60 minutes. Throughout this time the heart has been stopped with the aid of a heart/lung machine since the heart and/or the major blood vessels have to be opened for the operation.

Stopping the heart is damaging to the heart, and is so in proportion to the time for which the heart is stopped. Consequently, what it comes down to is that the shorter the period for which the heart is stopped the better this is for the patient. There is thus a need for a fixing technique which takes only little time, at least in any event takes appreciably less time than the current manual suture technique. Furthermore, the fixing technique must be reliable in the sense that the fixing is reliable and essentially leak-tight. Insofar as the devices disclosed in U.S. Pat. Nos. 3,143,742 and 3,574,865 meet this requirement, the positioning of, in particular, the bottom flange, that is to say the flange facing the heart, is, however, difficult since this flange has to pass through a local constriction in the form of the valve annulus, which has a diameter smaller than that of the bottom flange. Moreover, currently an increasing number of valve operations are carried out "minimally invasive". In this case there is then little space available for surgical suturing of the suture ring or for complex manipulation of separate components. There is thus a need for mechanisation or robotisation of the implantation.

The aim of the present invention is to provide a heart valve fixing device which makes reliable fixing of the heart valve prosthesis to the natural heart or a blood vessel possible, which fixing moreover can be produced relatively rapidly and preferably demands few manual fixing operations.

These aims are achieved with a cardiac prosthesis fixing device of the type indicated in the preamble in that the bottom flange is bent, or can be bent, reversibly, against a resilient force, from the first position into a second position in which the projection of the bottom flange on a radial transverse surface of the tubular element is located essentially on and/or within the periphery of the tubular element; and in that the bottom flange is fixed or can be fixed in said second position in such a way that the fixing can be released in order to bend back the bottom flange towards the first position under the influence of said resilient force.

In the case of the cardiac prosthesis fixing device according to the invention the terms bottom and top flange are intended primarily to differentiate between a first and a second flange. The terms bottom and top are certainly not intended to differentiate between a flange located in a lower position and a flange located in a higher position relative to one another in the vertical direction. The bottom flange is in particular understood to be the flange which, when feeding the cardiac prosthesis fixing device towards the fixing location, is located on that side of the valve annulus which faces the heart and has to pass through said valve annulus when positioning the cardiac prosthesis fixing device in order to be able to accommodate the valve annulus between the two flanges. If the direction in which the cardiac prosthesis fixing device is fed towards the valve annulus were to be vertical, the so-called bottom flange is then actually the flange located at the top and the so-called top flange is actually the flange located at the bottom.

When fitting the cardiac prosthesis fixing device, in particular when bringing it into its position, the bottom flange will already have been fixed to the tubular element or integrated therewith and have been brought into its second position, also referred to as the extended position, and fixed in place. Taking into account that the diameter of the tubular element is sized such that this fits between the valve annulus, this means that the bottom flange is able to pass through the valve annulus when in its second position. After the bottom flange has been inserted through the valve annulus, the fixing of the bottom flange can be released or removed, after which the bottom flange is able to return to the first position, or at least towards the first position, under the influence of the resilient force. Thus, the bottom flange is then able, in the first position, as it were to hook behind the valve annulus and, together with the top flange, which optionally can be fitted afterwards, to enclose the valve annulus. With this arrangement the valve annulus is enclosed between the bottom and top flanges and then acts as a reliable fixing point for fixing the cardiac prosthesis fixing device and valve prosthesis provided therein or valve prosthesis which may still have to be fitted therein. Because the valve annulus locally constricts the passage in which the valve prosthesis has to be fitted, the cardiac prosthesis fixing device according to the invention can be moved relatively easily through the relatively wider passage since the tubular element and the bottom flange in its second position have a diameter which is able to pass through the valve annulus and thus have a diameter which makes feeding through the passage, in particular a blood vessel, in the direction of the valve annulus possible. With this arrangement the tubular element and the bottom flange in the second position can optionally have an external diameter such that the whole can be fed through the passage to the annulus with some play. So as to be able to allow the tubular element to abut tightly on the valve annulus, which, inter alia, promotes sealing, the tubular element will have a diameter such that, or at least will be chosen by the surgeon with a diameter such that, it can be accommodated in the valve annulus with some stretching of the latter.

According to a further particular embodiment of the invention, it is advantageous if the top flange is bent, or can be bent, reversibly from the first position, against a resilient force, into a second position in which the projection of the top flange on a radial transverse surface of the tubular element is located essentially on and/or within the periphery of the tubular element; and if the top flange is fixed, or can be fixed, in said second position in a manner such that the fixing can be released in order to cause the top flange to bend back in the direction of the first position under the influence of said resilient force. In this way it is possible for the top flange already to be fixed to the tubular element, and optionally integrated therewith, before fitting the cardiac prosthesis fixing device and, at the same time, to ensure an adequate play in the passage via which the cardiac prosthesis fixing device has to be fed to its destination, the valve annulus, or at least to ensure easy feeding to said valve annulus. After all, the top flange also can then have a diameter narrower than the diameter of the passage via which the whole has to be fed.

Both in the case of the bottom flange and in the case of the top flange, if the latter has at least been bent, or is bendable, into a second position, the releasable fixing in the second position can be produced in a number of ways. Consideration can be given, inter alia, to making the cardiac prosthesis fixing device of a so-called memory metal, such as, for example, a nickel-titanium alloy. With such a construction the bottom and top flanges can be brought from the first position into the second position in order then, as it were, to freeze in said second position. This fixing can then be cancelled by heating the cardiac prosthesis fixing device, or at least the respective memory metal part thereof, above a certain temperature, after which the bottom, and optionally the top, flange return to their first position under the influence of the pretensioning. With this construction the so-called second position is, as it were, a frozen position which is cancelled by exceeding a certain temperature or at least releasing the frozen pretensioning forces. With this construction the temperature above which the fixed second position is released can be adjusted by means of suitable choice of the composition of the memory metal alloy. Releasable fixing in the second position can also be achieved in other ways. This will be further discussed further below.

In order to achieve clamping of the valve annulus it is advantageous according to the invention if, in the first position, the axial spacing between the bottom and the top flange, in particular the outside edges thereof, is less than the thickness of the valve annulus to be accommodated between them in order to be able to clamp the valve annulus between the bottom and top flanges in the assembled position. Specifically, on returning from the second position to the first position the bottom and top flanges will come into contact with the valve annulus before achieving the so-called first position at a point in time when there is still residual pretensioning force present in order to bend back the bottom and, respectively, top flange further in the direction of the so-called first position.

Clamping of the valve annulus can, moreover, also be ensured or, supplementary thereto, also further ensured if the bottom and the top flange in the first position are in a position in which they are pretensioned facing towards one another. This can be achieved, for example, by making the cardiac prosthesis fixing device available to the medical specialist with a spacer clamped between the bottom and top flanges. Before fitting the heart valve fixing device the bottom and, if appropriate, also the top flange must then be brought into and fixed into its/their second position, the spacer then being removed.

The bottom and top flanges can each be a flange extending uninterrupted around the periphery of the tubular element. However, it is also very readily conceivable to construct both the bottom flange and the top flange or one of these two flanges as an interrupted flange. In this context the flange constructed as an interrupted flange can, as it were, consist of flange lips or flange fingers which are separated from one another in the circumferential direction by cut-outs or incisions. Assuming an essentially round tubular body and cut-outs, the angular spacing between adjacent flange lips or fingers can then be, for example, 5, 10 or more degrees. The cut-outs or incisions can also extend over a much smaller angular spacing of 1 degree or even less, in which case the incisions are more or less pure incised slits. In order to facilitate, in particular, bringing the bottom and/or top flange from a first into a second position and causing the bottom and/or top flange to return from said second position to the first position, it is particularly advantageous according to the invention if the bottom and/or top flange comprises a number of fingers arranged distributed around the periphery of the tubular element and separated from one another by incisions, cut-outs or folds. Furthermore, it can also be advantageous if the inner flange and optionally also the outer flange have a more or less uninterrupted and an interrupted section. For example, the central section of the flange can be uninterrupted (which improves the seal with the annulus) and the peripheral section can be constructed as an interrupted section with fingers (which promotes firm fixing to the tissue).

In order, in particular, to restrict the number of further manual or at least medical operations, and thus the duration of the operation, after fitting the cardiac prosthesis fixing device, it is advantageous according to the invention if the tubular element is integrated with a valve or ring prosthesis or with a, preferably round or cylindrical, housing thereof. In this context integrated must be understood to mean that the valve or ring prosthesis or housing thereof has already been fixed to the tubular element prior to fitting or, in the extreme case, has been formed as an integral whole therewith. In practice, fixing of the valve prosthesis to the tubular element will preferably take place in such a way that the valve prosthesis is still turnable relative to the tubular element (about a longitudinal axis of the tubular element) in order to be able accurately to position the valve prosthesis.

With a view to accessibility of the tubular element during implantation, in particular the fixing to the surrounding tissue, it can be advantageous according to the invention if the tubular element and the valve prosthesis are assembled together only after implantation of the cardiac prosthesis fixing device. With a view to this it is advantageous according to the invention if the tubular element is provided with a lower limit in order to prevent a valve prosthesis positioned in the tubular element after implantation of the cardiac prosthesis fixing device from becoming detached in the downward direction from the tubular element and/or with a top closure in order to prevent a valve prosthesis fitted in the tubular element after implantation of the cardiac prosthesis fixing device from becoming detached in the upward direction from the tubular element. With this arrangement the lower limit and top closure do not necessarily have to be provided at the bottom and the top, respectively, of the tubular element. The point at issue here is that the lower limit prevents the valve prosthesis from being able to detach from the tubular element in the downward direction and that the top closure prevents the valve prosthesis from being able to detach from the tubular element in the upward direction. According to one embodiment, the lower limit can comprise a stop, such as an inward-pointing rib extending in the peripheral direction, arranged inside the tubular element at the bottom thereof. According to the invention the top closure can comprise a screw ring or snap-fit ring and/or resilient lips. It is also conceivable that the lower limit and top closure are provided simultaneously by the same elements. In this context consideration can be given, inter alia, to internal screw thread in the tubular element which is able to interact with external screw thread on the valve prosthesis or a bayonet fitting or a bayonet-like closure.

In order to improve the clamping of the valve annulus, it is advantageous according to the invention if the bottom and top flanges are at least partially arranged in accordance with a sinusoidal pattern in the peripheral direction of the tubular element. The reason for this is that the valve annulus, in particular in the case of an aortic valve, follows a sinusoidal pattern and that in this way the bottom and top flanges can be matched to the path of this sinusoidal pattern. The shape of the valve annulus will in general be dependent on the type of heart valve, such as aortic valve, mitral valve, pulmonary valve or tricuspid valve. Practice has shown that in other respects more or less standardised dimensions, in particular as far as the so-called diameter is concerned, can be maintained for the various types of heart valves. What this comes down to is that the heart valves are made available in various standardised sizes and that, before or during the surgical operation, the correct size for the patient is determined and the correct standardised heart valve or cardiac prosthesis fixing device is taken.

As far as the shape and size of natural heart valves are concerned, it can be pointed out in a general sense that natural heart valves consist of two or three valve cusps which are attached to the heart or a major blood vessel along a rim or a ligament. This rim or ligament, the valve annulus, can be calcified to a greater or lesser extent, which is usually the case if a valve prosthesis has to be fitted. The mitral valve consists of two valve cusps and the annulus in the case of a mitral valve is located in a more or less flat plane. The aortic valve consists of three valve cusps, the attachment of the valve cusps being half-moon-shaped, as a consequence of which the natural annulus of the aortic valve has a half-moon shape with three troughs at the location of the middle of the valve cusps and three peaks at the location of the commissura. The shape of the opening is more or less circular in the case of the three-cusp aortic valve and is somewhat kidney- or bean-shaped in the case of the two-cusp mitral valve. In principle, the cardiac prosthesis fixing device according to the invention can be used with any type of heart valve. According to the invention, this means that the so-called tubular element according to the invention does not have to have a circular shape, certainly in the case of a so-called mitral ring prosthesis. The shape of a cardiac prosthesis fixing device for a mitral ring prosthesis according to the invention could, in essence, also be kidney-shaped or bean-shaped as well as circular.

In particular if the cardiac prosthesis fixing device is intended for fixing an aortic valve prosthesis, the sinusoidal path of the bottom and top flanges will have a length of three sine periods together spanning the circumference of the tubular body. In particular in the case of a cardiac prosthesis fixing device for an aortic valve prosthesis, it is furthermore also very readily conceivable that the tubular element is a sinusoidally wave-shaped ring or sinusoidally wave-shaped cylindrical element with three sine periods.

If the valve annulus to be accommodated between the bottom and top flanges has a sinusoidal shape three periods long, as is the case with the annulus of the aortic valve, it is advantageous according to the invention if:

the top and bottom flanges comprise flange segments for clamping the sine wave troughs of the valve annulus, which flange segments are preferably positioned approximately 120° apart; and/or the top and bottom flanges comprise flange segments for clamping the sine wave peaks of the valve annulus, which flange segments are preferably positioned approximately 120° apart; and/or the top and bottom flanges comprise flange segments for clamping the sine wave origins of the valve annulus, which flange segments are preferably positioned approximately 60° apart.

The advantage of this is that in the case of such a sinusoidally wave-shaped valve annulus said valve annulus can be gripped by means of a segmented, in general discontinuous, bottom flange and optionally discontinuous top flange. With this arrangement the point of fixation to the valve annulus, that is to say the sine wave peaks and/or sine wave troughs and/or sine wave origins, can be chosen depending on the anatomy and/or condition of the valve annulus of the patient concerned. From the standpoint of accessibility, it will frequently be preferable to opt for clamping the sine wave peaks, which are, in fact, on the side facing away from the heart, which in general is the easiest to reach. However, depending on the anatomy and/or condition of the valve annulus, other locations for clamping the valve annulus can be chosen, depending on the patient. The fact that the fixing of the cardiac prosthesis fixing device becomes more reliable and robust with more clamping points should be obvious. A leak-tight seal on the valve annulus can be further ensured by making the segments sufficiently broad and/or making the top flange continuous and optionally rigid (that is to say not bendable into a second position) and/or using supplementary additional segments and/or constructing the tubular body such that it is an oversized fit in the valve annulus (which is then stretched somewhat) and/or some other means.

In order to improve the closure along the outer surface of the tubular element and to be able reliably to ensure this, it is advantageous according to the invention if the outer surface of the tubular element is concave. In this context it is optionally even possible for this concavity to continue into the bottom and/or top flange, which bottom and/or top flange then, as it were, form the ends of the concavity.

In order further to improve the anchoring or fixing of the cardiac prosthesis fixing device according to the invention it is advantageous according to the invention if the bottom and/or top flange or fingers of the bottom and/or top flanges is/are provided with anchoring means, such as barbs, points or roughenings, for anchoring in the valve annulus. Said barbs, points or roughenings, referred to in general as anchoring means, can then penetrate into the tissue of the valve annulus and fasten therein. For the same purpose it is also possible for roughenings to be provided on the outside of the tubular element.

Although, according to the invention, use can be made of memory metals, such as nickel-titanium alloys, which are fixable/freezable in a pretensioned state, it is preferable according to the invention if the cardiac prosthesis fixing device further comprises fixing means for releasably fixing the bottom and/or top flange in the second position. Such fixing means can comprise at least one annular element, such as a sleeve, ring or suture, which are placed or can be placed around the bottom and/or top flange, when the flange is in the second position, in order to fix the bottom and, respectively, top flange in their second position. When the cardiac prosthesis fixing device has then been brought into place inside the valve annulus, the fixing means can be removed or the fixing effect thereof can be cancelled. According to a particularly preferred embodiment, the fixing means comprise a sleeve in which the tubular element with the bottom flange in the second position and optionally the top flange in the second position can be accommodated or have been accommodated in such a way that the tubular element, the bottom flange and the optional top flange can be pushed out of the sleeve by retracting the sleeve from the tubular element in the longitudinal direction facing away from the bottom flange. In this way the entire heart valve fixing device, which may or may not already be provided with the heart valve prosthesis, accommodated in a sleeve can be brought into position inside the valve annulus, after which the sleeve can be withdrawn and the bottom and, optionally, top flange can return to a first position so that the bottom and top flanges together are able to engage/enclose the valve annulus. However, according to the invention it is also very readily conceivable for the fixing means to comprise a suture, such as a ligature, which is stretched taut around the bottom flange in the second position and for the two ends of the suture to run over the outside of the tubular element to that side of the tubular element which faces away from the bottom flange in order to be fixed in place at that side or beyond that end, it being possible to remove the suture after detaching the one end of the suture by pulling on the other end of the suture and those parts of the suture running over the tubular element preferably being guided in guide means. Such an embodiment with which the fixing means for fixing the bottom flange comprise a suture is in particular advantageous when the cardiac prosthesis fixing device has already been provided with the valve prosthesis concerned prior to fitting. Specifically, in such a case it is less sensible to remove, or at least to cut through or cut, the suture around the bottom flange between the valve cusps. This is because the valve cusps could easily be damaged while doing this. With this arrangement the guide means through which the suture sections preferably run have the advantage that cutting of the suture into the valve annulus tissue is counteracted when pulling away the suture. The guide means themselves can also be constructed such that they are also removable and then are withdrawn after removing the suture. Fixing means, such as a suture or ligature, can also be highly advantageously used with the top flange. Since the latter is still accessible from above after fitting, without going through the tubular element, guide means are superfluous and the suture will not have to run over the tubular element either on the inside or on the outside. If the valve prosthesis itself, that is to say the replacement for the valve cusps, is placed in the tubular body only after fitting and fixing the tubular body, the ends of the suture for fixing the bottom flange in the second position can then also run through the tubular body on the inside to the accessible top thereof since it is also possible via the passage through the tubular element to reach the bottom thereof in order to remove the suture.

The cardiac prosthesis fixing device according to the invention can be used both with completely synthetic heart valve prostheses and with biological heart valve prostheses, which can originate from animal or human donors and which may or may not have stents. The cardiac prosthesis fixing device according to the invention can also be used with so-called ring prostheses, which are used to "repair" the diameter of the opening of a leaking valve (usually the mitral valve) by constricting this by means of a ring only. This ring can be placed inside and constrict the diameter of the opening by being engaged by the annulus. Such ring prostheses can be uninterrupted or interrupted and can be round or bean/kidney-shaped.

As far as the flanges are concerned, the cardiac prosthesis fixing device will in particular have been made of a relatively stiff material. The flanges can themselves be bendable against a resilient force or can optionally be mounted on supports, such as arm-like bodies, which are bendable against a resilient force. The cardiac prosthesis fixing device according to the invention can, in particular, have been produced from a metal suitable for implantation. In practice for such applications metals are frequently coated with a carbon coating to counteract clotting. The cardiac prosthesis fixing device, and in particular also the flanges thereof, can be coated on the outside with textile-like material in order to make tissue ingrowth possible and for leak-tight covering of the gap between the tubular element and the valve annulus. Materials of this type are usually made of Dacron or Teflon-like synthetic fibres. This textile-like material can also have been treated with substances which counteract blood clotting and/or infections.

In accordance with the invention, the cardiac prosthesis fixing device according to the invention can also very readily be used for fixing vascular prostheses in major vessels. In this respect the term cardiac prosthesis fixing device must therefore be considered to be broader than a fixing device for fixing prostheses in passages or conduits through which blood flows.

SECTION 1.2

The present invention relates to a prosthesis fixing device, such as for a cardiac prosthesis, comprising a tubular element intended to lie, when the cardiac prosthesis fixing device is in the fitted position, with the outside in contact with the peripheral wall of part of the circulatory system and to accommodate a valve prosthesis inside it, the tubular element having pins arranged distributed around the periphery, which pins penetrate the peripheral wall when the device is in the fitted position.

A cardiac prosthesis fixing device of this type is disclosed in U.S. Pat. No. 3,143,742. This device comprises two flange-like rings which are mounted on a common sleeve provided with screw thread and can be moved towards one another over said screw thread by screwing in order to clamp annulus tissue or possibly some other type of circulatory system wall tissue between them. Both flange-like rings are provided with passages through which anchoring pins can be pressed outwards. With this arrangement the pins are shaped as an arc of a circle and pressure is exerted on the pins which run through passages in the one flange-like ring by the other flange-like ring on moving the two flange-like ring elements towards one another, so as to emerge at the outside in order to penetrate circulatory system wall tissue. This known cardiac prosthesis fixing device has a number of disadvantages. One significant disadvantage is that the fitting of this known cardiac prosthesis fixing device, in particular the clamping of the annulus tissue and simultaneous penetration of the circulatory system wall tissue by the pins, is much less simple than it appears. Firstly, the flange-like rings make it more difficult to position the cardiac prosthesis fixing device in place since these rings must have an external diameter greater than that of the annulus to be clamped and therefore it is relatively difficult for them to pass through the annulus to be clamped. In order to move the flange-like elements towards one another the inner sleeve, provided with external screw thread, has to be turned whilst the ring-like flanges have to be prevented from turning with the sleeve. Turning the inner sleeve, provided with external screw thread, for this purpose will, inter alia, require some force and partly for this reason is difficult to operate remotely by means of catheter-like aids. Furthermore, there is a risk that some turning of the inner sleeve relative to the ring-like flanges can already occur when manoeuvring the sleeve into its destination, as a consequence of which the points of the pins can emerge outwards prematurely. These points can then damage the wall tissue of the circulatory system. Furthermore, it must be pointed out that according to FIG. 10 of U.S. Pat. No. 3,143,742, the points of the upper pins already protrude beyond the upper flange-like ring in advance and thus will already be able to give rise to tissue damage on manoeuvring the ring into its position. Furthermore, the cardiac prosthesis fixing device according to U.S. Pat. No. 3,143,742 consists of a relatively large number of separate components, which is not only a disadvantage from the cost point of view but, moreover, also makes production more difficult and, perhaps even more importantly, increases the risk of failure. If just one of the pins cannot be pushed properly outwards, this is sufficient to impede further screwing of the ring-like flanges towards one another and thus to make the reliability of the fixing of the cardiac prosthesis fixing device uncertain.

The aim of the present invention is to provide an improved cardiac prosthesis fixing device of the type indicated in the preamble. In particular, the aim of the invention is to provide a cardiac prosthesis fixing device which is very reliable, in particular with regard to the fixing on fitting.

The abovementioned aim is achieved according to the invention in that each pin is arranged on an arm which is attached by one end to the tubular element in a manner which permits swinging about a hinge axis, such as via a fold line or bending line, and in that the arms and pins are movable, by swinging about the hinge axis, from an insertion position, in which they are essentially located inside the tubular element, into a fixing position in which at least the pins, viewed in the radial direction, project outside the tubular element. Because the pins are completely inside the tubular element, that is to say inside an imaginary infinitely continual circumferential surface thereof, during insertion, it can be ensured that, on feeding the cardiac prosthesis fixing device to its destination, the pins are not able prematurely to come into contact with the surrounding tissue material of the circulatory system and thus are not able to impede manoeuvring of the device to its destination and possibly to cause damage. Furthermore, the cardiac prosthesis fixing device according to the invention can be produced as an integral whole, although, if desired, it can also be made up of a number of components. A further advantage is that swinging the arms, with the pins thereon, outwards in order to penetrate surrounding tissue of the circulatory system can be achieved in a manner which is not only very simple but also very reliable, inspection afterwards also being readily possible. For example, use can be made of a balloon to be inflated within the circumferential plane defined by the arms or of another type of element that is capable of exerting forces directed radially outwards. Visual inspection from the inside can take place afterwards using known means, by checking whether all arms, and thus also the pins formed thereon or fixed thereto, have swung sufficiently far outwards.

In order to be able to ensure with a high degree of certainty that the pins, or at least the points at the ends thereof, are not able to come into contact with surrounding tissue of the circulatory system while manoeuvring the pins into their destination, it is preferable according to the invention if the pins are located within the longitudinal boundaries of the tubular element in the insertion position and if the tubular element is provided with radial passages located alongside the pins in the radial direction, in particular slit-shaped passages extending in the longitudinal direction of the arms, such that the pins emerge through these passages on swinging from the insertion position into the fixing position. Thus, the tubular element will completely shield the pins from surrounding tissue of the circulatory system while manoeuvring into its destination.

In order to simplify the outward swinging of the arms, with the pins provided thereon, it is preferable if the arms, viewed in the longitudinal direction of the tubular element, extend essentially in said longitudinal direction. This makes it possible, certainly if all arms are oriented in the same direction with respect to the longitudinal axis, to swing said arms outwards by pressing a ring or forcing body, having a diameter greater than the diameter determined by those parts of the arms and/or pins located radially furthest to the inside and a diameter smaller than the internal diameter of the tubular element, between the arms in the longitudinal direction into the tubular element. Such a forcing body could be, for example, the valve prosthesis, or at least a surrounding ring thereof. Furthermore, it is pointed out that it is certainly not necessarily the case that this forcing body has to be pressed between the arms by means of a compressive force, but that it is very readily possible for said forcing body to be driven into the tubular element from one side by pulling a pull element, joined to the forcing body, from the other side. In this context it is particularly preferable if the arms, viewed from the hinge axis, point away from the heart in the insertion position.

According to a further advantageous embodiment, each arm can have at least two, in particular two, pins. In this way the robustness of the fixing can be improved and, moreover, it is possible to penetrate the valve annulus from opposing sides.

In order to improve not only the fixing of the cardiac prosthesis fixing device, but in particular also the seal thereof with the surrounding tissue of the circulatory system wall, it is preferable according to the invention if the tubular element has a bottom and/or top flange extending in the circumferential direction of the tubular element, which flange, at least in the fitted position, projects outwards with respect to the tubular element in order to come into contact with, or at least to overlap, the bottom or, respectively, the top of the valve annulus. In order, in particular, to make it possible with this arrangement for the bottom or, respectively, top flange to point outwards with respect to the tubular element after positioning of the cardiac prosthesis fixing device at its destination, it is preferable according to the invention if the bottom or, respectively, top flange has a number of flange fingers separated from one another by incisions, cut-outs or folds and arranged distributed around the periphery of the tubular element. In this way it is possible to maintain the bottom or, respectively, top flange in the position in which it is extended with respect to the tubular element, or optionally in the inward-pointing position, while manoeuvring into its destination and to bend the bottom or, respectively, top flange into a position in which it points radially outwards only when it is at its destination. In order to ensure that the valve prosthesis to be fitted after positioning the cardiac prosthesis fixing device is not able to detach from the cardiac prosthesis fixing device, it is preferable according to the invention if the tubular element is provided with a lower limit in order to prevent a valve prosthesis placed in the tubular element after implantation of the cardiac prosthesis fixing device from detaching from the tubular element in the downward direction, and/or with a top closure in order to prevent a valve prosthesis placed in the tubular element after implantation of the cardiac prosthesis fixing device from detaching from the tubular element in the upward direction. With this arrangement, the lower limit can be a stop arranged inside the tubular element at the bottom thereof, such as an inward-pointing rib extending in the circumferential direction. With this arrangement the top closure can be a screw ring or a snap-fit ring and/or resilient snap-fit lips.

In order always to be able to orient the valve prosthesis in a specific desired position with respect to the circulatory system, irrespective of the precise rotational position of the cardiac prosthesis fixing device, it is preferable according to the invention if the valve prosthesis can be accommodated in the tubular element such that it can be turned about its longitudinal axis, for example by means of a screw thread connection, a bayonet connection or a combination of a peripheral recess in the one part and one or more ribs on the other part interacting therewith, the cardiac prosthesis fixing device preferably also being provided with a twist lock in order to be able to fix the tubular body and the valve prosthesis in a desired position with respect to one another.

In order to be able to ensure that the pins penetrate the valve annulus as much as possible, in the case of a sine wave-shaped valve annulus, as is the case with the annulus of the aortic valve, it is preferable according to the invention if the arms and fingers are arranged at least partially in accordance with a sine wave-like pattern in the peripheral direction of the tubular element. In this context, it is particularly preferable if the sine wave path has a length of three sine periods together spanning the periphery of the tubular body. Furthermore, according to the invention it can be advantageous in this context if the tubular element is a sine-wave-shaped ring or sine-wave-shaped cylindrical element with three sine wave periods.

In order to facilitate the outward swinging of the arms provided with pins so that surrounding wall tissue is penetrated by the pins, and in particular to restrict or at least to reduce as far as possible the exertion of forces on the cardiac prosthesis fixing device during this operation, it is preferable according to the invention if the arms provided with pins have been bent, or can be bent, against a resilient force from an initial position, corresponding to essentially the fitted position, into the insertion position and are fixed or can be fixed in said insertion position in such a way that the fixing can be released in order to cause the arms provided with pins to bend back to, or at least in the direction of, the fitted position under the influence of the resilient force.

In order to improve the abutment of the cardiac prosthesis fixing device with a valve annulus and, in particular, the seal with said valve annulus, it is preferable according to the invention if at least part of the external surface of the tubular element is concave.

With regard to the material in clauses 28-38 of this application, considered separately from the other clauses, reference can be made for embodiments and further explanation to Netherlands Patent Application 1 012 150 which was filed on May 25, 1999, has not previously been published and is incorporated as an integral part of this PCT application by means of Sections 1.1, 2.1, 3.1, 4.1 and associated FIGS. 1-14.

SECTION 1.3

The present invention relates to a fixing device for fixing to vascular wall tissue, comprising a tubular element which can be accommodated within a passage surrounded by vascular wall tissue and is provided with bottom fingers arranged distributed in the peripheral direction of the tubular element and with top fingers arranged distributed in the peripheral direction of the tubular element, the bottom and top fingers having a first position in which they project outwards from the tubular element with respect to the axial direction of the tubular element in order to be able to accommodate between them the vascular wall tissue surrounding the passage.

A fixing device of this type in the form of a cardiac prosthesis fixing device is disclosed in U.S. Pat. No. 3,143,742 and in U.S. Pat. No. 3,574,865. These publications have both already been discussed at the start of Section 1.1 and therefore it now suffices to refer to the description given there, which can be considered as being incorporated here.

When fitting a fixing device, such as, in accordance with the present invention, in particular a vascular prosthesis fixing device, a portal prosthesis fixing device or an obturator prosthesis fixing device, in a passage surrounded by vascular wall tissue, the fixing device will have to engage on the vascular wall tissue surrounding the passage and at least part of the device will also have to pass through this passage. Furthermore, the fixing device usually has to be fed via the circulatory system to the passage in which the fixing device has to be fitted. When it has reached its destination, the fixing of the fixing device to the vascular wall tissue surrounding the passage must be reliable, robust for a prolonged period and preferably also quick and effective to produce.

The aim of the present invention is to provide an improved fixing device, for fixing to vascular wall tissue, which meets the above requirements.

According to the invention said aim is achieved in that both the bottom and the top fingers have been bent aside, or can be bent aside, reversibly, against a resilient force, from the first position into a second position in which the projection of the bottom and top fingers on a radial transverse surface of the tubular element is located essentially on and/or within the periphery of the tubular element; and in that the bottom and top fingers are fixed or can be fixed in said second position by a sleeve in which the tubular element and at least part of the bottom and top fingers which are in the second position have been accommodated or can be accommodated such that the tubular element, the bottom fingers and the top fingers can be slid completely out of the sleeve by sliding the sleeve in the longitudinal direction of the tubular element, in order to allow the bottom and top fingers to return to the first position. In the so-called first position, which essentially corresponds to the position after fixing, the fingers project outwards with respect to the tubular body in order to accommodate between them the vascular wall tissue that surrounds the passage in which the fixing device is to be fitted. The fingers are, as it were, directed, against a resilient force, along the tubular body, or at least along the imaginary tube surface defined by the tubular body (if the tubular body is shorter or appreciably shorter in the axial direction than the longitudinal direction of the fingers) and held in said position, directed along the tubular body or optionally within the tubular body, by placing a sleeve around the whole. The sleeve is then inserted through the passage, in which the fixing device is to be fitted, until it is correctly positioned, after which the sleeve is withdrawn in one direction in order to release first the bottom fingers (or possibly the top fingers) and then the other fingers, the top fingers (or possibly the bottom fingers), and to allow these to return to their original position under the influence of the resilient force, generated on bringing into the extended position, and in doing so to accommodate between them the vascular wall tissue surrounding the passage. This enclosure between them can be clamping, but it is also conceivable that the fingers puncture said vascular wall tissue and anchor in this way or optionally in combination clamp and penetrate the surrounding vascular wall tissue. The sleeve also makes it easier to feed the device to its destination, that is to say the passage in which the fixing device is to be fitted, and, moreover, at the same time ensures that the means with which the fixing device is fixed to the surrounding vascular wall tissue, that is to say the top and bottom fingers and possibly supplementary anchoring means, remain shielded from surrounding tissue and thus are not able to damage this surrounding tissue.

Although it is not essential, it is advantageous according to the invention if the bottom and top fingers extend essentially axially in opposing directions in the second position. What is achieved in this way is that the bottom and top fingers move towards one another in order to accommodate vascular wall tissue between them. However, it is not entirely precluded that the bottom and top fingers extend in the same axial direction from the tubular body or the sleeve arranged around the latter, in which case it is then an advantage if the bottom fingers are shorter than the top fingers or, vice versa, that the top fingers are shorter than the bottom fingers, so that first the one type of fingers and then the second type of fingers go into their first position. A corollary of this embodiment will usually be that the sleeve is first partially slid off, in order then to position the fixing device precisely in place, and only then to slide the sleeve completely off.

According to a further advantageous embodiment, the bottom and top fingers will, in the first position, extend in the radial direction with respect to the tubular body.

According to a further advantageous embodiment, the sleeve is provided with an end which is sloping or tapered or curved with respect to the axial direction thereof. In particular said sloping, tapered or curved end will have been made sharp close to the outermost end of the sleeve. What this amounts to in the case of the sleeve being cut off at a slope is that the sloping cut runs at an angle of less than 45° with respect to the axial direction. This has the advantage that the sleeve can be used in order first to cut a passage of suitable size at the location where the fixing device has to be fitted, or to cut the passage somewhat larger if it is not large enough. It should be clear that the end edge of the sleeve will be made sharp for this purpose.

According to a further advantageous embodiment, it is possible, by, in the case of a tapered sleeve, leaving the central part of the tapered end of the sleeve open, to draw the sleeve up over a guide wire. Such embodiments are, for example, useful when producing STS or ETS anastomoses or when fitting prosthesis fixing devices, cannulas or working conduits. The sleeve can then be used for joining end-to-side to a major vessel (this, as it were, produces a T-joint) in order to form a passage in the wall of the major vessel. With this embodiment it can furthermore be advantageous if the ends of the bottom fingers span a surface which is sloping, tapered or curved with respect to the axial direction of the sleeve when the fingers are in the second position. In particular, this surface spanned by the ends of the bottom fingers will then follow the same course as the surface spanned by the sloping, tapered or curved end of the sleeve.

According to a further advantageous embodiment of the invention, the bottom and/or the top fingers can have pointed ends. Such pointed ends can then provide for penetration of the surrounding vascular wall tissue, in which case it is then possible that no clamping of this surrounding vascular wall tissue between the bottom and top fingers has to take place at all. Such clamping is, however, advantageous.

According to a further advantageous embodiment, in their first position, the bottom and/or top fingers define a flange surface extending uninterrupted or with interruptions around the tubular element. The fingers can then be, as it were, flange fingers, as discussed in Section X.1.

The fixing device according to Section X.3 can advantageously be constructed in accordance with various preferred embodiments as described in Section X.1.

In the case of the fixing device according to Section X.3 the terms bottom and top fingers are primarily intended to differentiate between first and second fingers. The terms bottom and top fingers are certainly not intended to differentiate between fingers located at a lower position and fingers located at a higher position with respect to one another in the vertical direction. Bottom fingers are in particular understood to be the fingers which are located closest to the fixing point on feeding to the fixing point, or, in the case of bottom and top fingers pointing in opposing axial directions in the second position, point towards the fixing point, in which latter case the bottom fingers will also pass through the fixing point in order to be able to accommodate the vascular wall tissue around the fixing point between the bottom and top fingers.

SECTION 1.4

According to a first aspect of Sections X.4, the invention relates to a vascular fixing device for fixing the end of a vessel.

Such vascular fixing devices are known, for example for joining two blood vessels end-to-end. In this case use can be made of a fixing device which is attached to the end of the vessel and is then coupled to a fixing device which is joined to the end of another vessel. However, it would also be possible to join the ends of the two vessels to one another at the same time.

According to this first aspect of Sections X.4, the aim of the invention is to provide a vascular fixing device for fixing to an end of a vessel, by means of which the end of the vessel can be fixed rapidly and efficiently to the fixing device.

According to the first aspect of Sections X.4, the above-mentioned aim is achieved by providing a vascular fixing device for fixing to an end of a vessel, comprising:
 a tubular body having an inner flange formed thereon for accommodating in the interior of the end of the vessel;
 an outer flange to be located, in a fixing position, around the end of the vessel, around and in contact with the outside of the vascular wall tissue, which outer flange, in said fixing position, runs around the inner flange and overlaps the latter, the outer flange being bendable or bent from the fixing position, against a resilient force, into a pretensioned fitting position located further away from the inner flange, and the outer flange, in said pretensioned fitting position, being fixable or fixed in such a way that said fixing can be released in order to cause the outer flange to bend back in the direction of the fixing position under the influence of the pretension.

The fixing device can be fixed relatively easily to an end of a vessel by inserting the inner flange in the end of the vessel after the outer flange has first been brought into its pretensioned fitting position. The fixing of the outer flange is then removed and the outer flange is allowed to return to its fixing position under the influence of the pretension in order, in said fixing position, together with the inner flange to clamp the vascular wall tissue located around the end of the vessel. With this arrangement the inner flange can be a rigid inner flange. The inner flange can be, for example, a cylindrical body, in which case the tubular body with inner flange formed thereon can be referred to as a single cylindrical body. The end of the vessel must then be slid over the rigid inner flange, the external diameter of which will then preferably be approximately equal to or smaller than the internal diameter of the end of the vessel.

In order to facilitate the insertion of the inner flange into the end of the vessel, it can, according to an advantageous embodiment of the first aspect of Section X.4, be advantageous if the inner flange is bendable or has been bent from the fixing position, against a resilient force, into a pretensioned fitting position located a greater distance away from the outer flange and if the inner flange is fixable or has been fixed in said pretensioned fitting position in such a way that said fixing can be released in order to cause the inner flange to bend back in the direction of the fixing position under the influence of the pretension. With this arrangement the functioning of the inner flange is essentially the same as that of the outer flange.

According to an advantageous embodiment of the first aspect of Section X.4, the outer flange, and optionally the inner flange, will have been made from a superelastic metal alloy or an alloy with a shape memory which has been activated/can be activated by heat, such as a nickel-titanium alloy, for example nitinol. Using an outer flange, and optionally an inner flange, made from such a material it is possible to bring said flange from the fixing position into a fitting position and to freeze the flange concerned in said fitting position. The frozen position can then be released by heating the flange concerned to above a certain temperature. This temperature can very well be in the region of the body temperature, for example approximately 38° to 40°, or even lower than the body temperature.

According to a further advantageous embodiment of the first aspect of Section X.4, in the fitting position the outer flange extends in a direction essentially opposed to that of the inner flange and the outer flange is fixed or is fixable in said fitting position by means of a sleeve in which the outer flange is accommodated. By subsequently sliding off or otherwise removing the sleeve, the outer flange is then released and is able to snap back, for example through approximately 180°, into a position running parallel to the inner flange, in which position the outer flange and the inner flange together clamp the end of the vessel.

A fixing device for producing an ETE anastomosis (where two vessels are joined to one another end-to-end) can be implemented advantageously according to the first aspect of Section X.4 if the fixing device comprises two of said inner flanges, which extend essentially in the extension of one another, and two of said outer flanges, which in the fitting position are essentially located transversely with respect to the inner flanges with the outsides facing one another. With such an embodiment the outer flanges can be held in their fitting position by means of a mechanical fixing, for example if the fixing device comprises a U-shaped annular element opening towards the middle, in which the ends of the outer flanges can be accommodated or are accommodated in the fitting position.

According to a further advantageous embodiment, a fixing device can, in accordance with the first aspect of Section X.4, be fixed to another blood vessel if the tubular element is provided all round with suture passages.

According to a second aspect of Sections X.4, the invention relates to a fixing device for fixing in a passage surrounded by vascular wall tissue.

Fixing devices of this type are needed, for example, to produce a so-called ETS anastomosis, for fixing a portal in a vessel wall for a cannula, working conduit or other type of surgical or medical instrument or implant to be inserted via the vessel wall, or as a coupling piece for a cannula or working conduit. Fixing devices of this type in accordance with the invention can also be useful for sealing undesired cavities, passages or connections in a vessel wall or hollow organ, such as, for example, a hole in the atrium or ventricle septum.

The aim of the invention according to this second aspect of Section X.4 is to provide a fixing device for fixing in a passage surrounded by vascular wall tissue, which fixing device can be fitted easily, rapidly and reliably.

To this end the invention in accordance with the second aspect of Section X.4 provides a fixing device for fixing in a passage surrounded by vascular wall tissue, comprising:

a tubular element that delimits a passage, an outer flange on the tubular element to come into contact, at the access side of the passage, with the vascular wall tissue surrounding the passage, an inner flange made up of inner flange segments, wherein each inner flange segment is arranged on an arm, one end of which is attached to the tubular element in a manner which allows swinging about a hinge axis, such as via a fold line or bending line, and wherein the arms and flange segments are movable, by swinging about the hinge axis, from an insertion position, located essentially within the outline of the passage, into a fixing position in which the inner flange segments, overlapping the outer flange, can come into contact, on that side of the passage which faces away from the access side, with the vascular wall tissue surrounding the passage.

The access side is understood to be that side of the vascular wall tissue from which the passage therein is approached. In the case of a blood vessel this can be either the inside or the outside. The fixing device is brought into position by bringing the outer flange of the fixing device, from the access side, into contact with the vascular wall tissue around the passage and then moving the arms with inner flange segments from the insertion position into the fixing position. In the fixing position the vascular wall tissue surrounding the passage will then be clamped between the inner flange segments and the outer flange. With this arrangement it is very readily conceivable that the inner flange segments, or parts thereof, also penetrate the vascular wall tissue. This can be useful, in particular with a view to firm anchoring. With this arrangement the arms with inner flange segments can be brought into their fixing position by exerting a force on the arms, for example by pressing an annular or tubular article between the arms with inner flange segments. Such an annular or tubular article can be, for example, a cannula, an obturator cap to be placed in the fixing device or the end of a vessel which is to be joined to the fixing device and is provided with a further fixing device. The arms with flange segments can, however, also have been bent inwards into their insertion position against a resilient force and automatically return to their fixing position after the fixing is removed. Such a fixing can be a mechanical impediment, such as a suture or ligature stretched around the arms with flange segments. It can also be highly advantageous to make the arms and inner flange segments, or at least the arms, from a superelastic metal alloy or an alloy with shape memory which has been activated or can be activated by heat, such as a nickel-titanium alloy, for example nitinol. As has already been indicated above in connection with the first aspect of Section X.4, the arms with inner flange segments are then able automatically to return to their fixing position from a freezing position after this has been cancelled, for example by heating the arms with inner flange segments to a certain temperature.

In order to prevent a further construction to be connected to a fixing device, which may or may not already have been implanted, being inserted too deeply through the fixing device, it is advantageous in accordance with the second aspect according to Section X.4 if the tubular element is provided with a lower limit in order to prevent a prosthesis, such as an obturator cap or vascular prosthesis or cannula, placed in the tubular element after implantation of the fixing device, from detaching from the tubular element in the downward direction. In order to prevent the further construction detaching from a fixing device in the opposite direction, it is advantageous if the fixing device is provided with a top closure in order to prevent a prosthesis, such as an obturator cap or vascular prosthesis or cannula, placed in the tubular element after implantation of the fixing device, from detaching from the tubular element in the upward direction. Since the second aspect of Section X.4 in particular is a more detailed embodiment of the invention according to Section X.2, the special embodiments outlined in that section also constitute special embodiments of the invention according to the second aspect of Section X.4.

BRIEF DESCRIPTION OF THE DRAWING FIGURES

The present invention will be explained in more detail below with reference to illustrative embodiments shown diagrammatically in the drawing. In the drawing:

SECTION 2.1

Figure 11A:
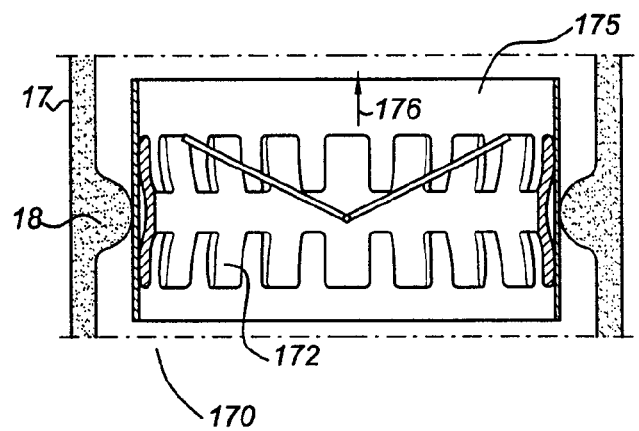
Figure 11B:
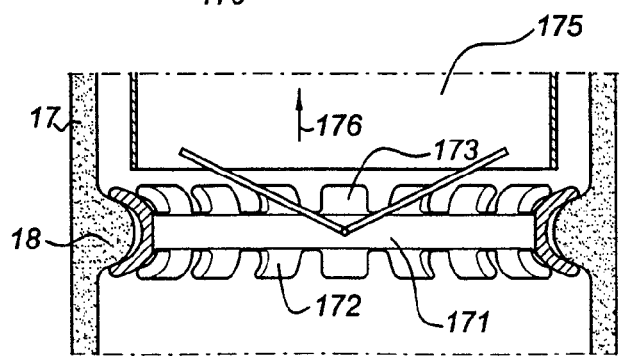
Figure 12:
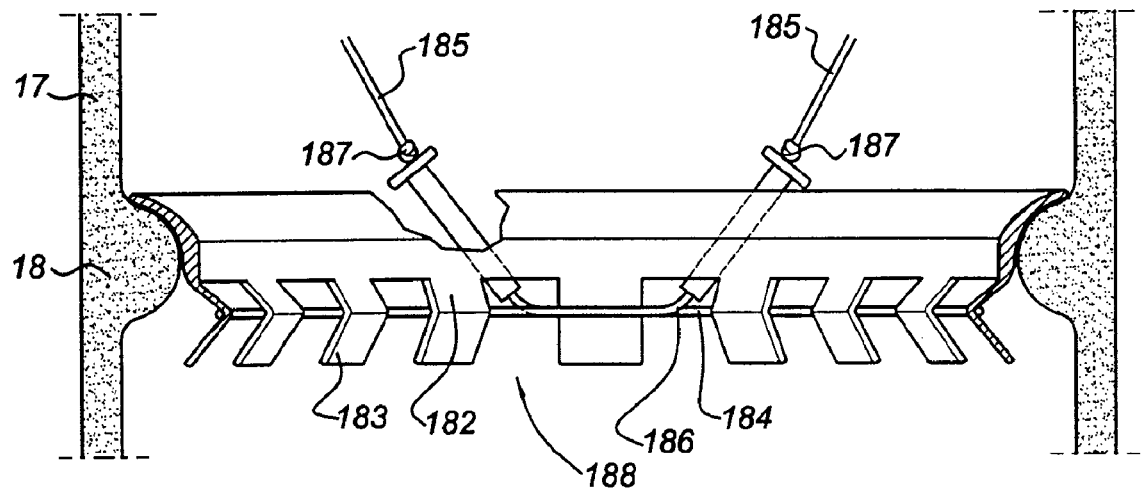
Figure 13A:
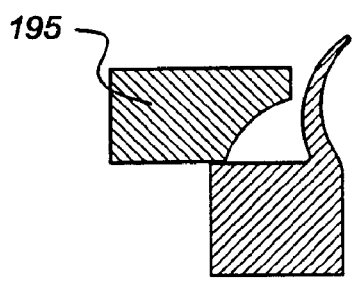
Figure 13B:
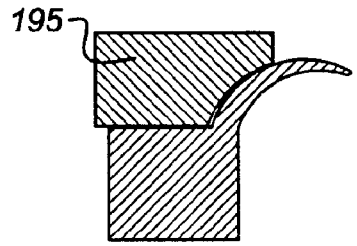
Figure 14:
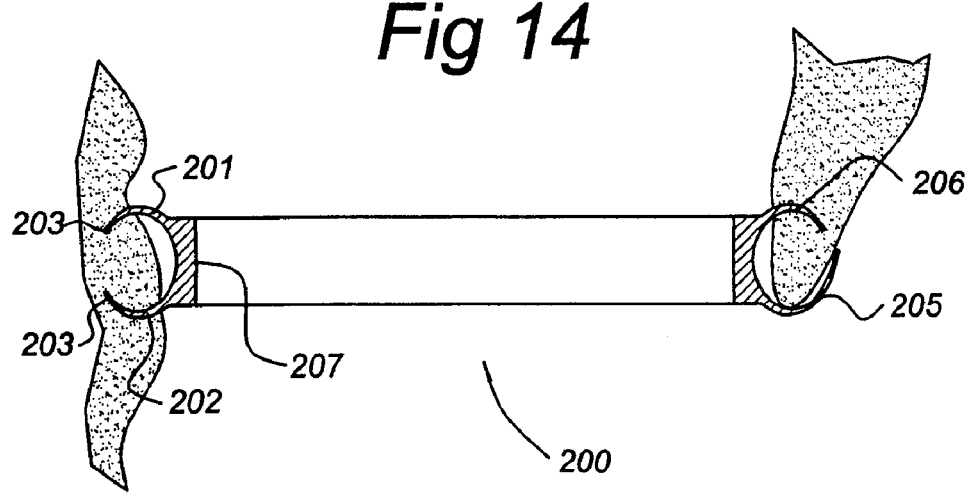

FIG. 11 shows, diagrammatically, a fourteenth embodiment of a cardiac prosthesis fixing device according to the invention, where FIG. 11A shows the cardiac prosthesis fixing device in a position suitable for fitting, that is to say bringing into position, inside the annulus of a heart valve and FIG. 11B shows the same cardiac prosthesis fixing device after removal of the fixing means for fixing the bottom and top flanges in the second position;

FIG. 12 shows a diagrammatic, perspective view of a fifteenth embodiment of a cardiac prosthesis fixing device according to the invention;

FIG. 13 shows, highly diagrammatically, as a detail a way in which in particular the bottom flange, but if desired also the top flange, can be brought back from the second position into the first position using aids, FIG. 13A showing the second position and FIG. 13B showing the first position;

FIG. 14 shows a diagrammatic longitudinal sectional view of a mitral valve prosthesis device according to the invention;

SECTION 2.2

Figure 18:
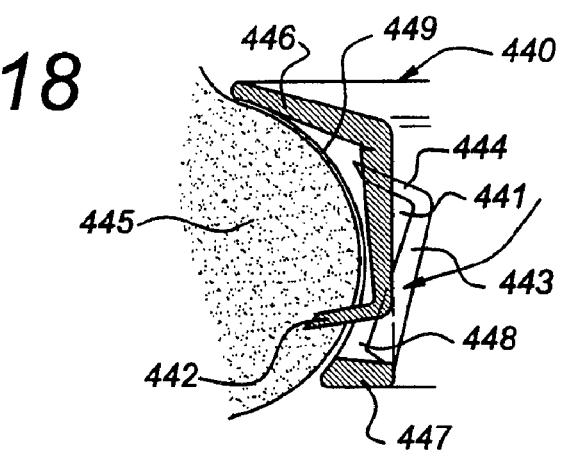
Figure 19:
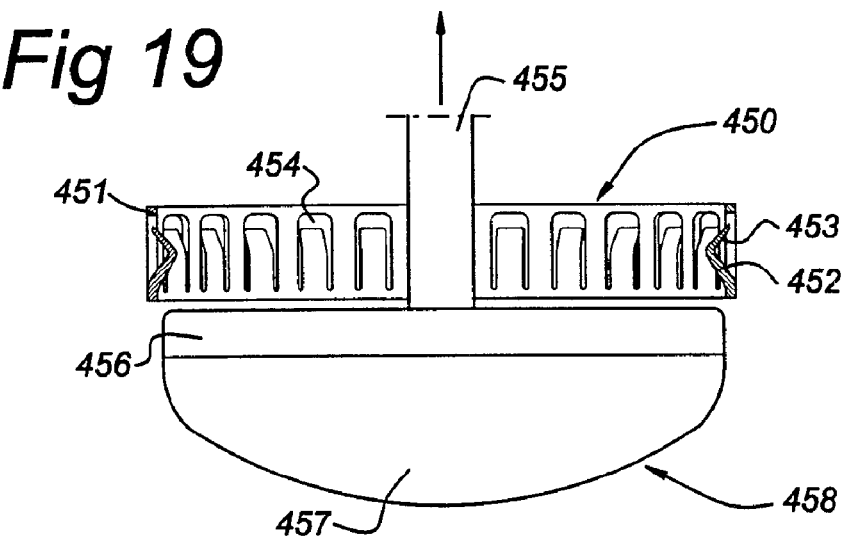
Figure 20A:
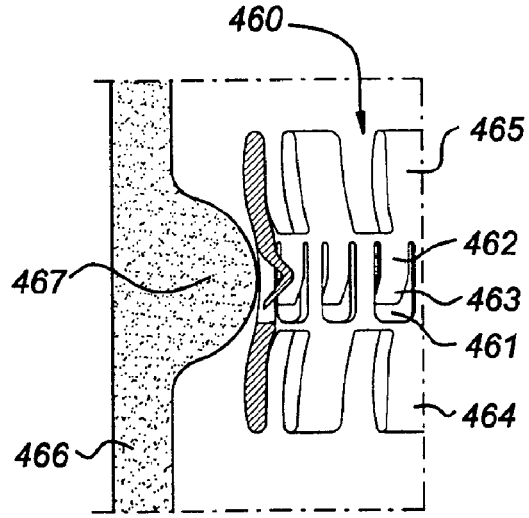
Figure 20B:
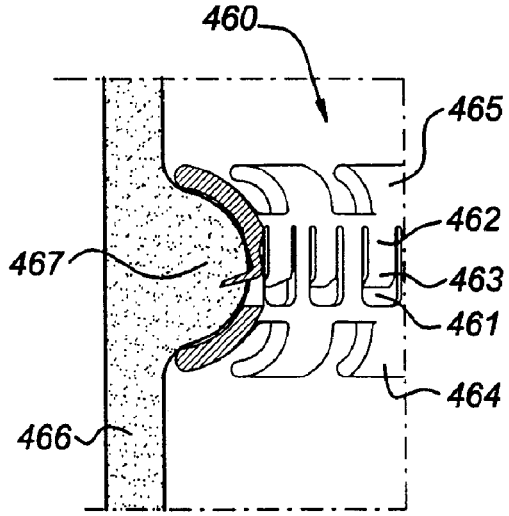
Figure 21:
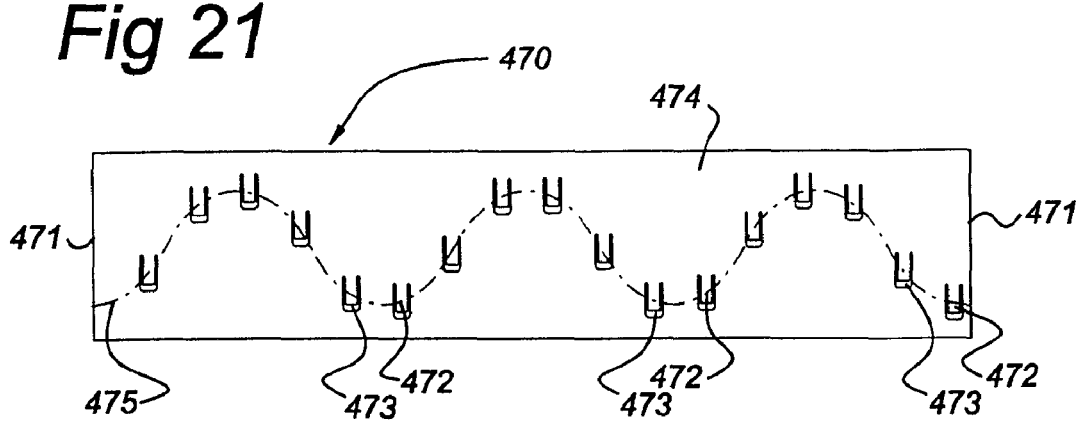
Figure 22:
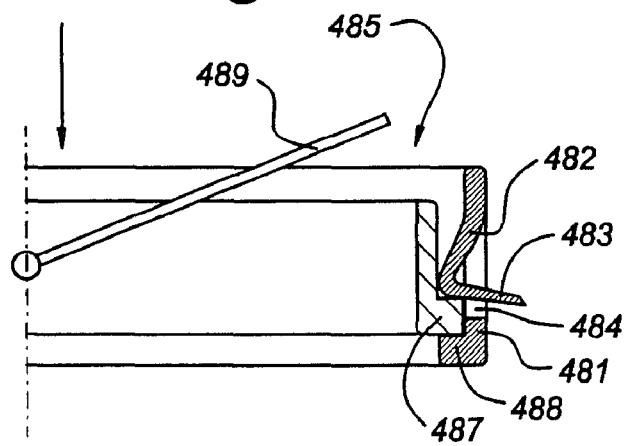
Figure 23A:
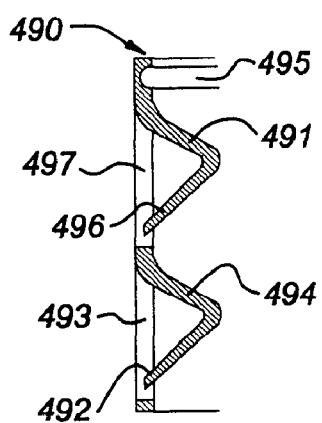
Figure 23B:
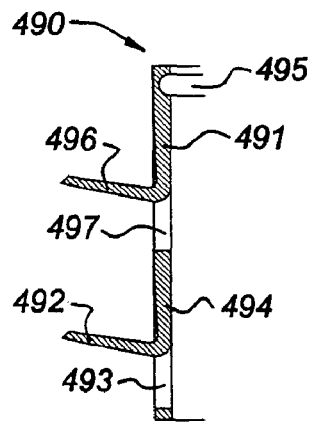
Figure 24A:
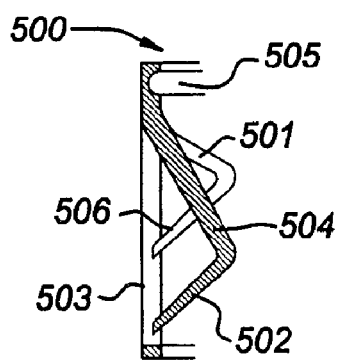
Figure 24B:
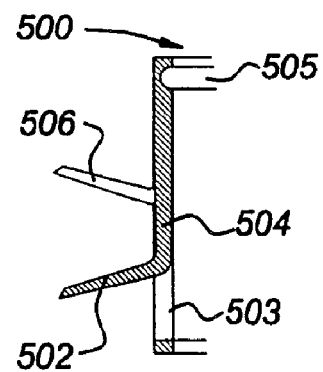
Figure 25:
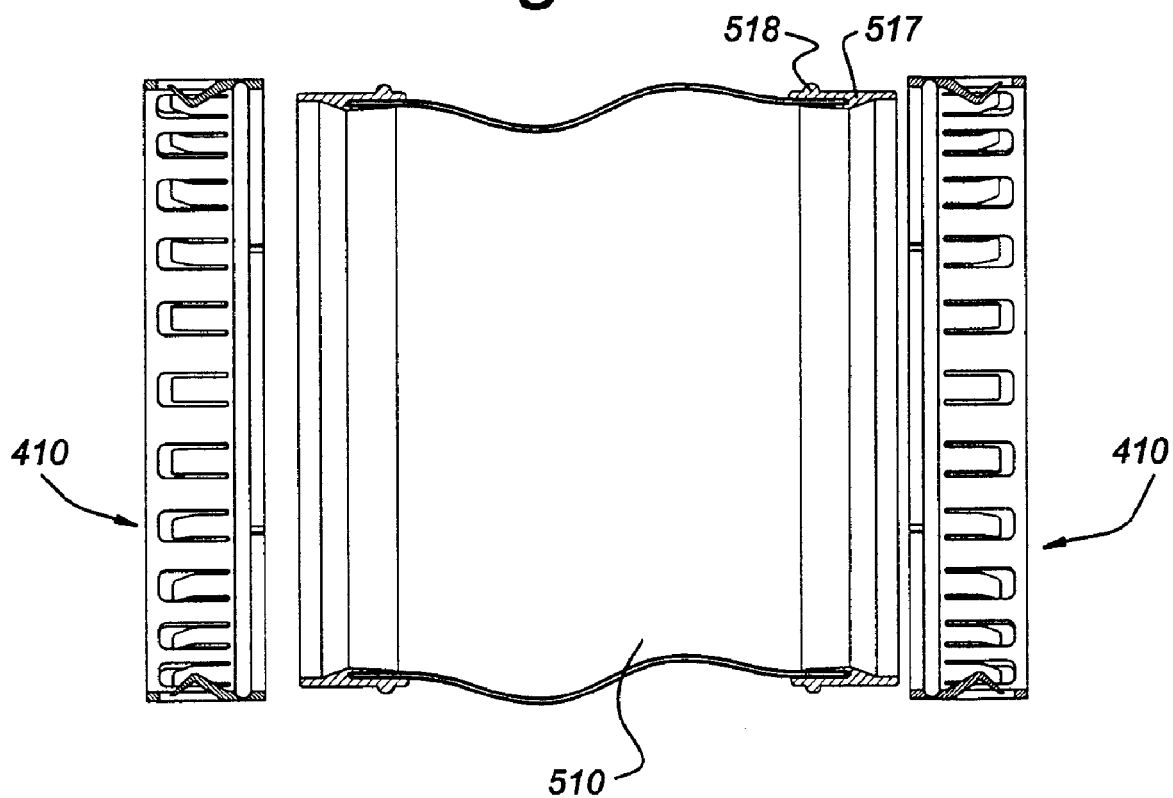

FIG. 15 shows a longitudinal sectional view of a prosthesis fixing device according to the invention (bottom) and a cardiac prosthesis which can be fitted therein (top);

FIG. 15A shows a detail a from FIG. 15 showing a pin provided on an arm, in the insertion position;

FIG. 15B shows the same detail as FIG. 15A but now with the pin provided on an arm in the fixing position;

FIGS. 16A and 16B show, as a detail corresponding to FIG. 15A and FIG. 15B, respectively, a variant of the prosthesis fixing device according to the invention;

FIGS. 17A and 17B show in a manner corresponding to FIGS. 15A and 15B, respectively, a further variant of a prosthesis fixing device according to the invention;

FIG. 18 shows, as a detail of a sectional view in a manner comparable to that in FIGS. 15A and 15B, yet a further variant of a prosthesis fixing device according to the invention;

FIG. 19 shows a longitudinal sectional view of yet a further variant of a prosthesis fixing device and, in plan view, an auxiliary element for swinging out the arms with pins;

FIGS. 20A and 20B show, as a detail, comparable with the detail in FIGS. 15A and 15B, a cross-sectional view of yet a further variant of the prosthesis fixing device according to the invention, vascular wall tissue also being shown in cross-section;

FIG. 21 shows an opened-up inside view of yet a further variant of the prosthesis fixing device according to the invention;

FIG. 22 shows part of a cross-sectional view of yet a further variant of a prosthesis fixing device according to the invention with a cardiac prosthesis locked therein;

FIGS. 23A and 23B show, as a detail corresponding to FIGS. 15A and 15B, respectively, a variant of the prosthesis fixing device according to the invention;

FIGS. 24A and 24B show, as a detail corresponding to FIGS. 15A and 15B, respectively, a variant of the prosthesis fixing device according to the invention;

FIG. 25 shows, diagrammatically, an application of the prosthesis fixing device according to the invention in a vascular prosthesis.

SECTION 2.3

Figure 26A:
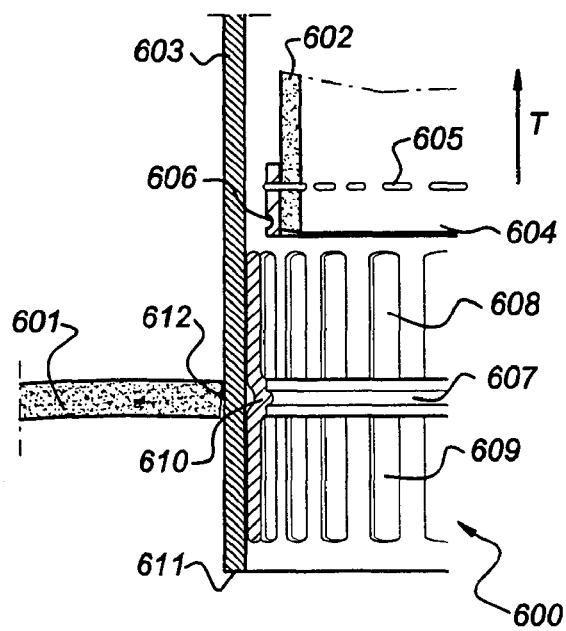
Figure 26B:
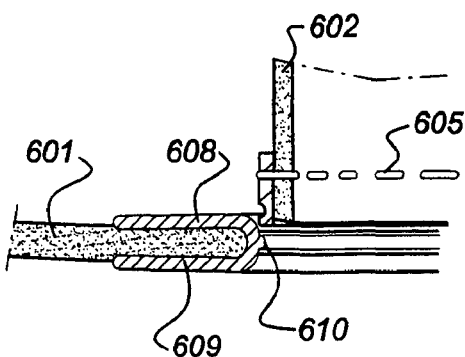
Figure 27A:
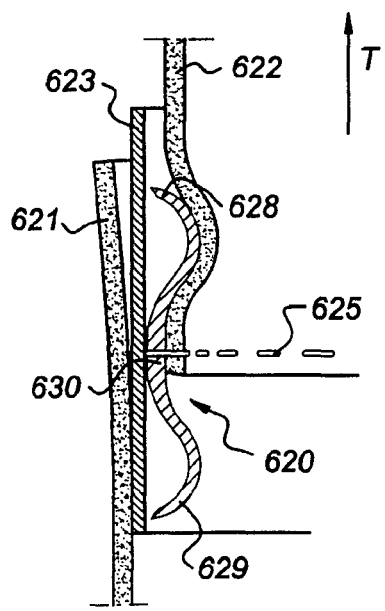
Figure 27B:
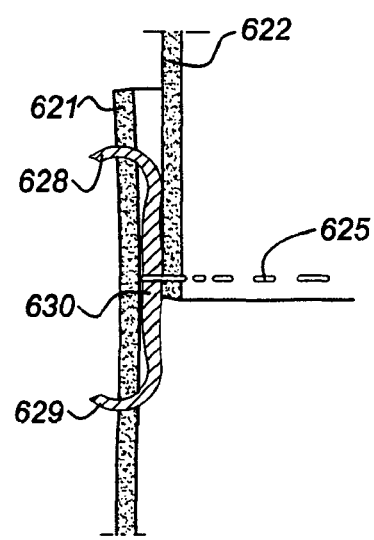
Figure 30A:
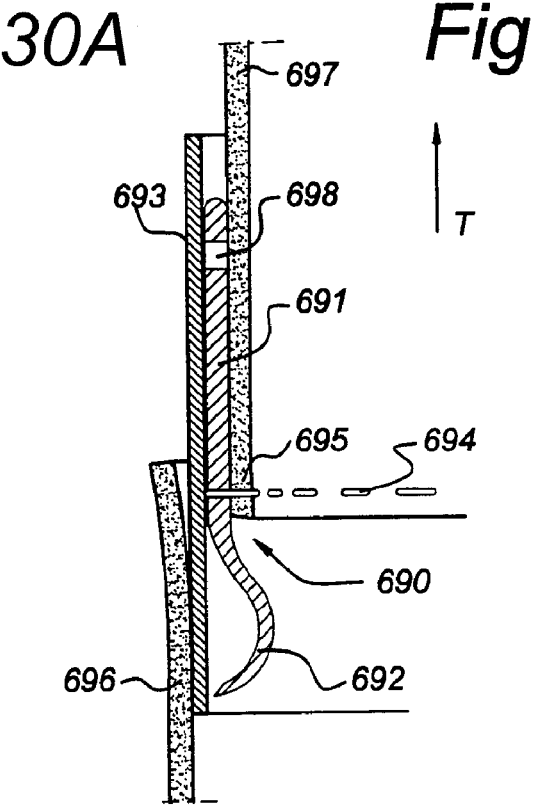
Figure 30B:
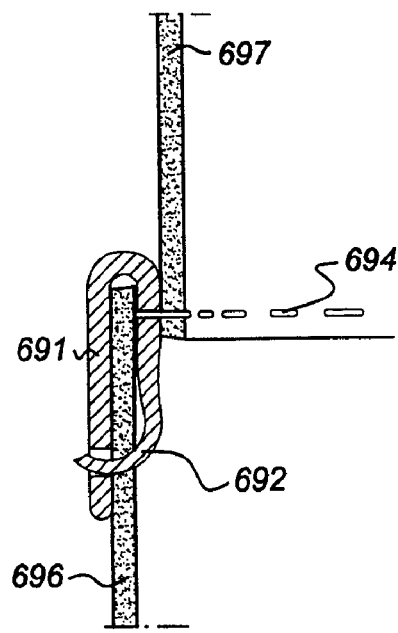
Figure 31A:
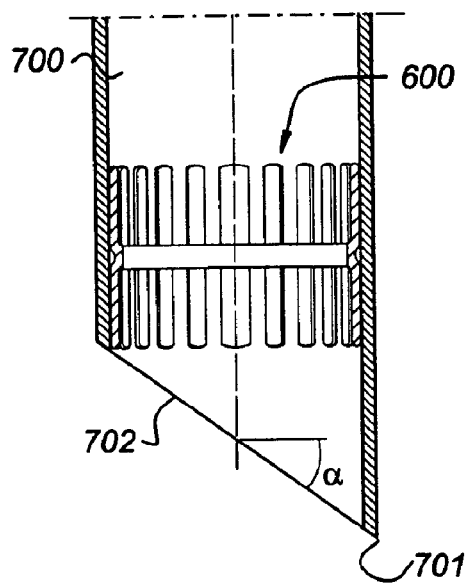
Figure 31B:
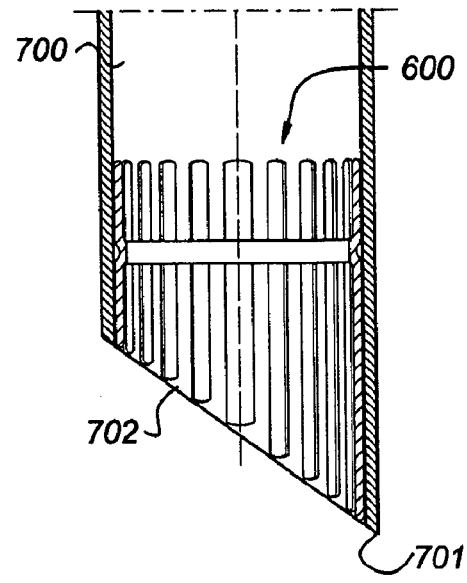
Figures 32A, 32B, 32C:
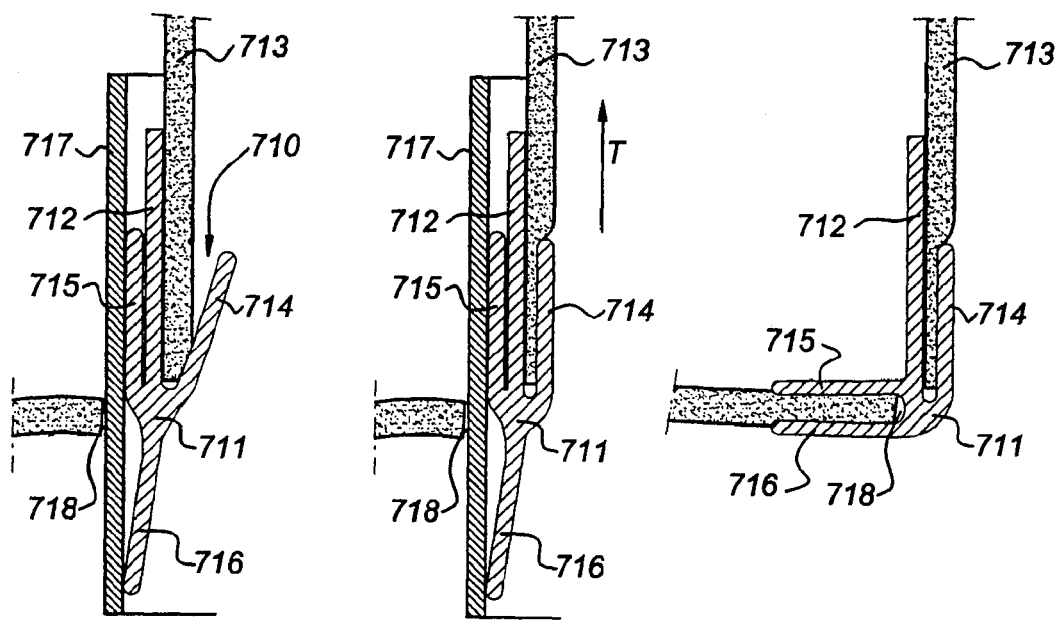

FIG. 26 shows, diagrammatically, as a detail (approximately the left-hand half of) a longitudinal sectional view of a first embodiment of a fixing device according to the invention, FIG. 26A showing an axial extended position and FIG. 26B showing a radial extended position;

FIG. 27 shows, diagrammatically, as a detail (approximately the left-hand half of) a longitudinal sectional view of a second embodiment of a fixing device according to the invention, FIG. 27A showing an axial extended position and FIG. 27B showing a radial extended position;

FIG. 28 shows, diagrammatically, as a detail (approximately the left-hand half of) a longitudinal sectional view of further embodiments of fixing devices according to the invention, FIG. 28A showing a position ready for fitting, FIG. 28B showing a radial, first position and FIG. 28C showing an obturator as further embodiment;

FIG. 29 shows, diagrammatically, as a detail (approximately the left-hand half of) a longitudinal sectional view of yet a further embodiment of a fixing device according to the invention,
FIG. 29A showing a position before joining two vessels and FIG. 29B showing a position after joining two vessels;

FIG. 30 shows, diagrammatically, as a detail (approximately the left-hand half of) a longitudinal sectional view of yet a further embodiment of a fixing device according to the invention,
FIG. 30A showing a position ready for insertion and FIG. 30B showing a released position;

FIG. 31 shows, diagrammatically, a longitudinal sectional view of yet a further embodiment of a fixing device according to the invention, FIG. 31A showing a first further embodiment and FIG. 31B showing second further embodiment;

FIG. 32 shows, diagrammatically, as a detail, (approximately the left-hand half of) a longitudinal sectional view of yet a further embodiment of a fixing device according to the invention,
FIG. 32A showing a first condition, FIG. 32B showing a second condition and FIG. 32C showing third condition.

SECTION 2.4

Figures 33A, 33B:
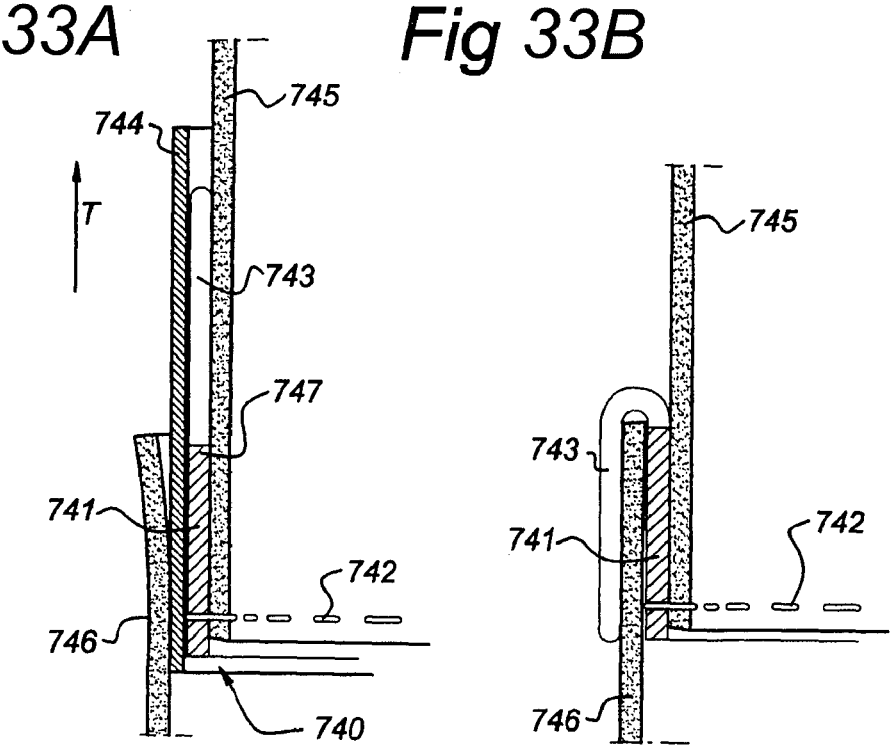
Figure 34:
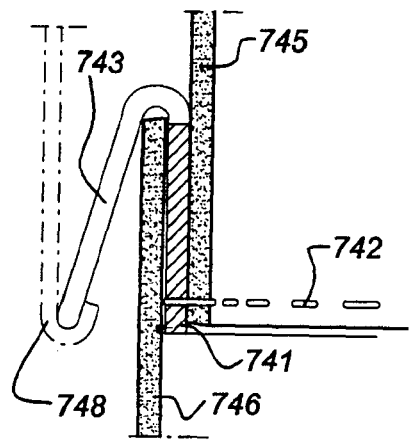
Figures 35A, 35B:
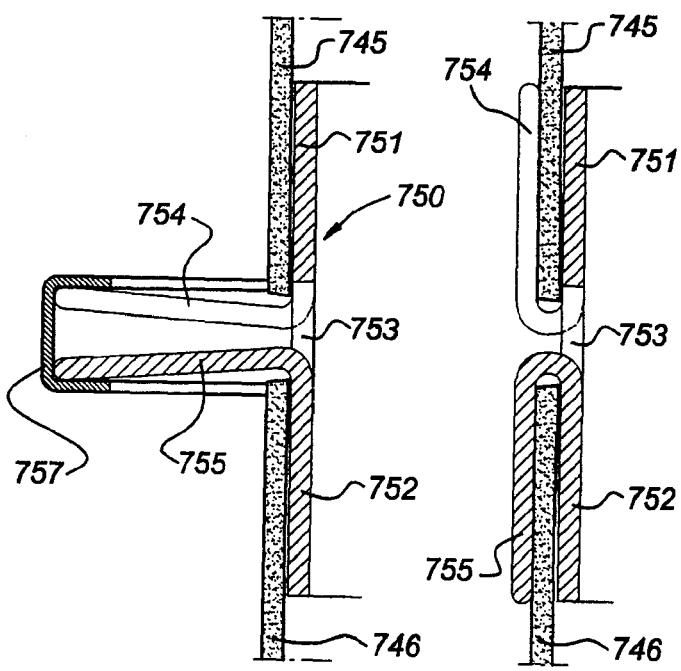
Figure 36A:
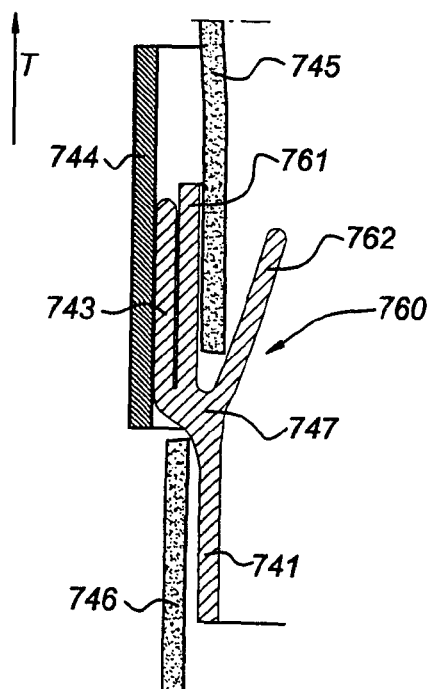
Figure 36B:
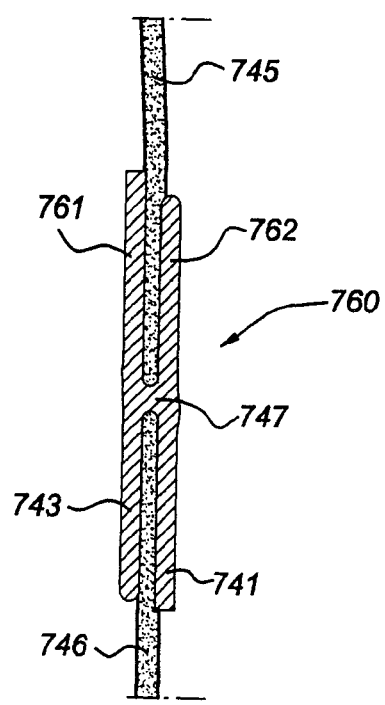
Figure 37A:
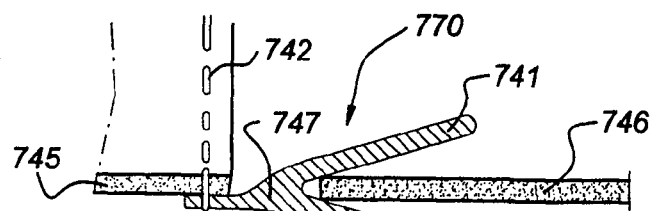
Figure 37B:
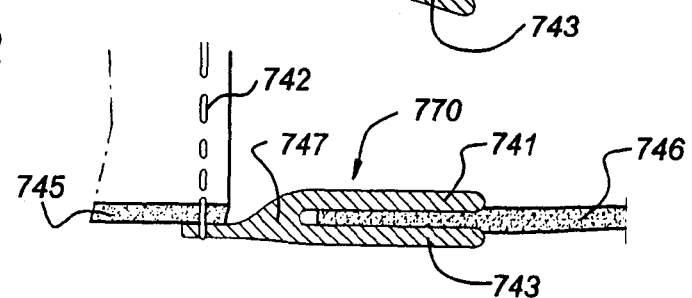
Figure 38A:
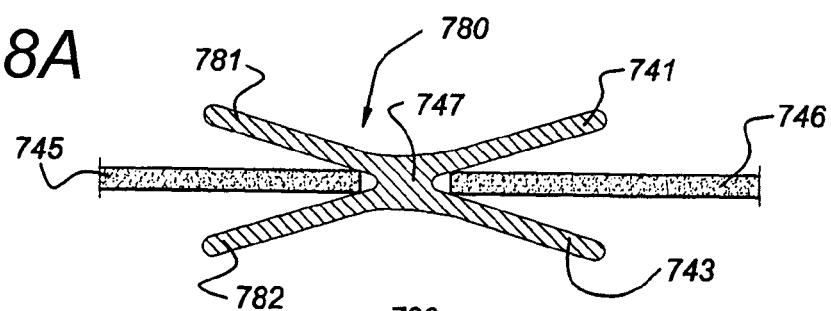
Figure 38B:
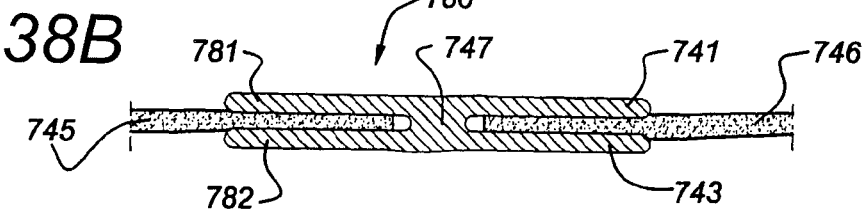
Figure 39A:
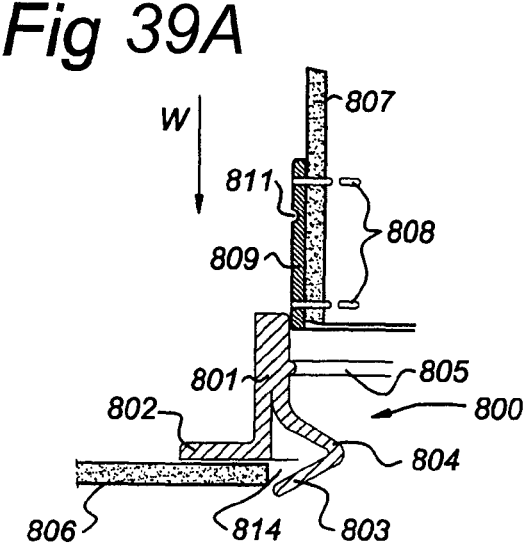
Figure 39B:
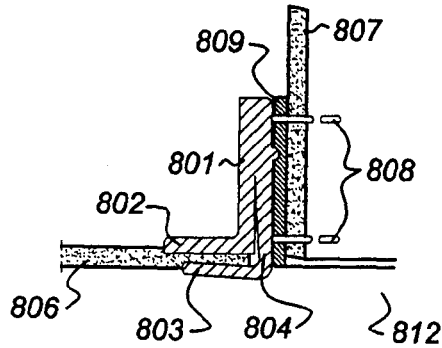
Figure 40B:
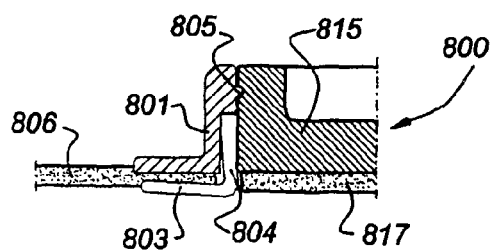
Figure 40A:
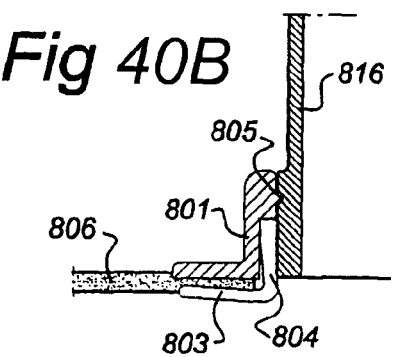
Figure 41A:
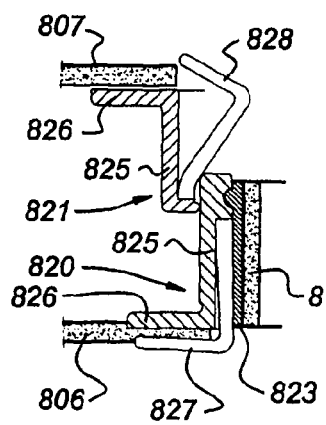
Figure 41B:
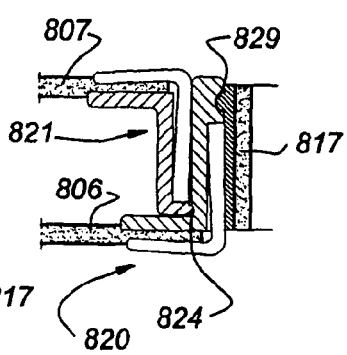
Figure 41C:
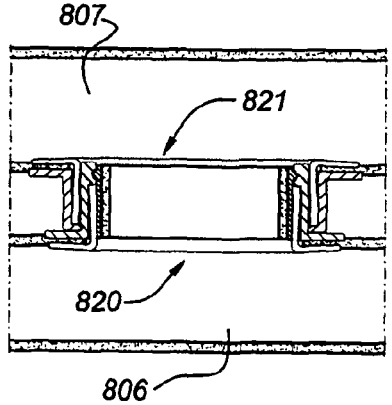
Figure 42A:
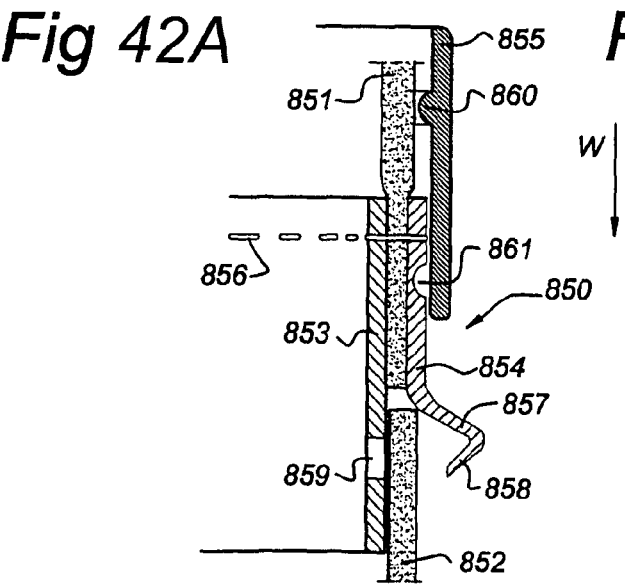
Figure 42B:
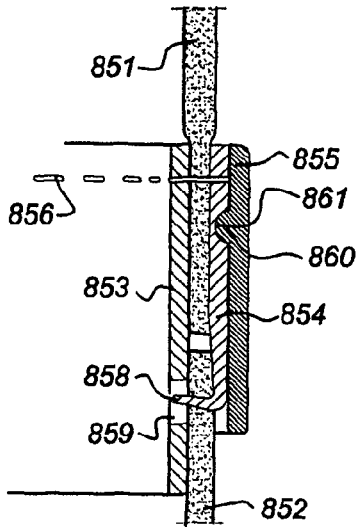
Figure 43A:
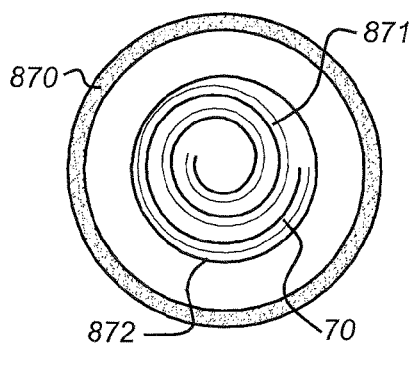
Figure 43B:
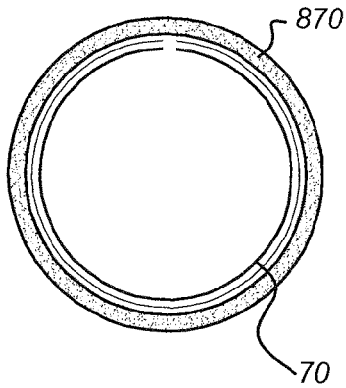
Figure 43C:
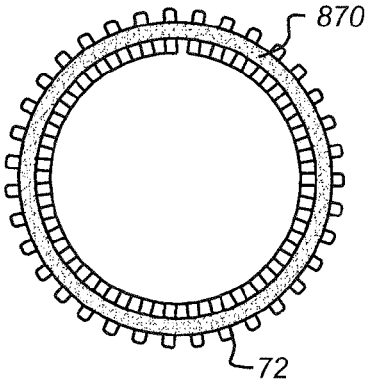
Figure 44:
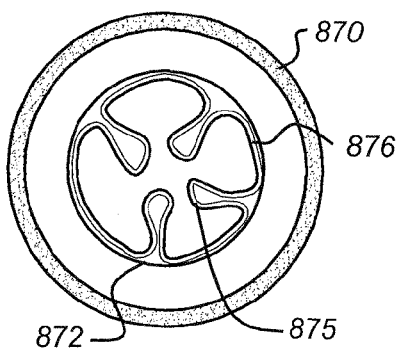
Figure 45:
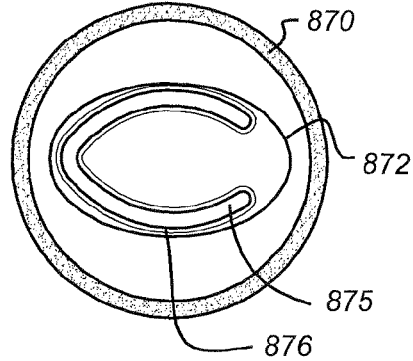
Figure 46:
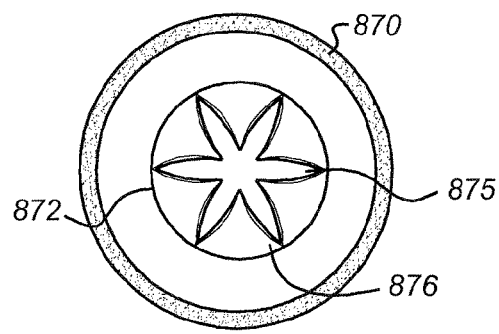
Figure 47A:
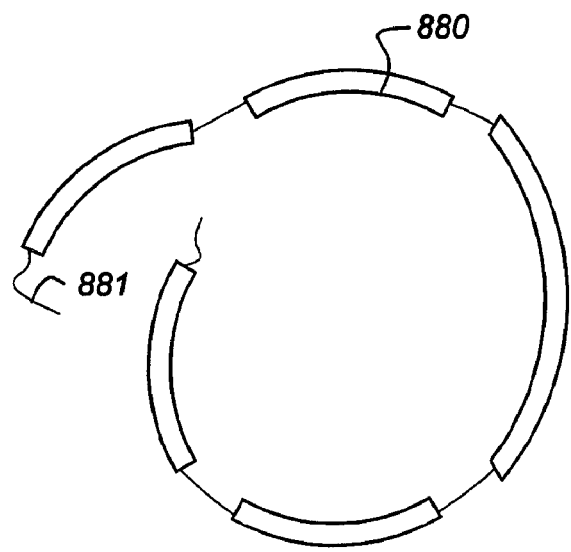
Figure 47B:
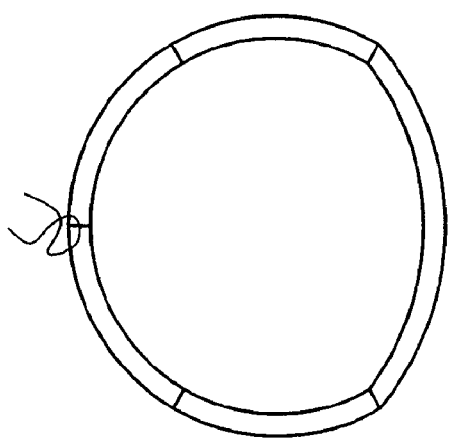
Figure 48A:
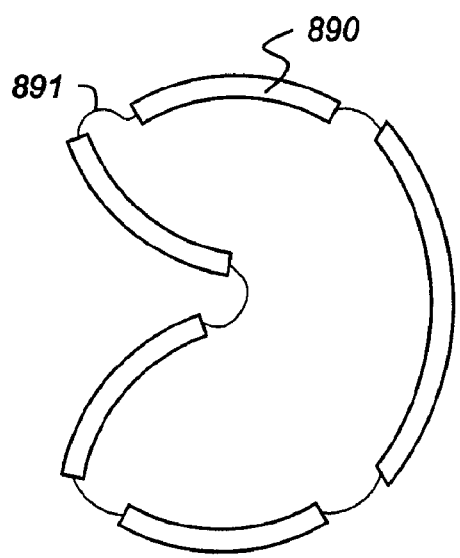
Figure 48B:
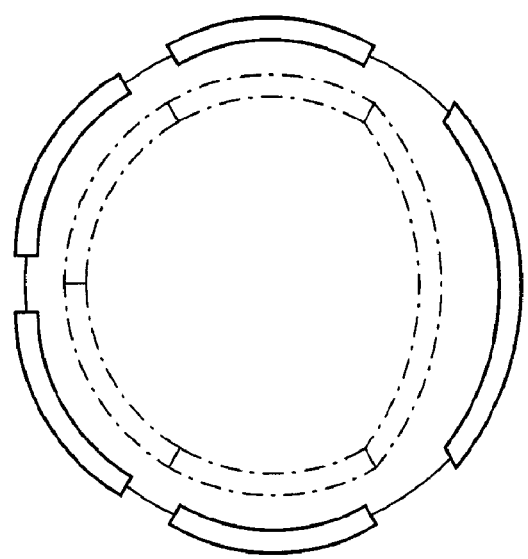
Figure 49A:
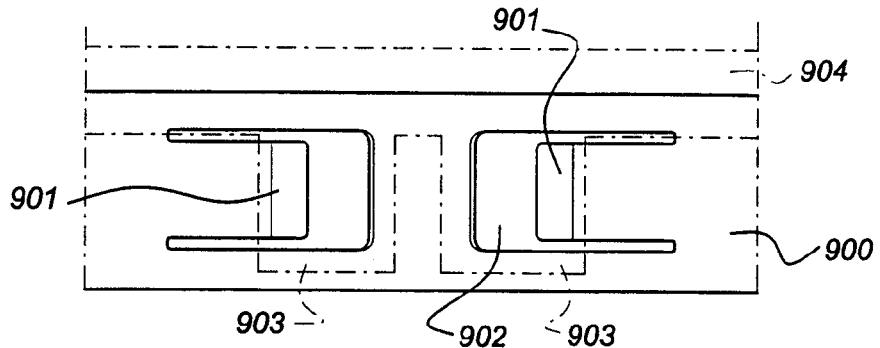
Figure 49B:
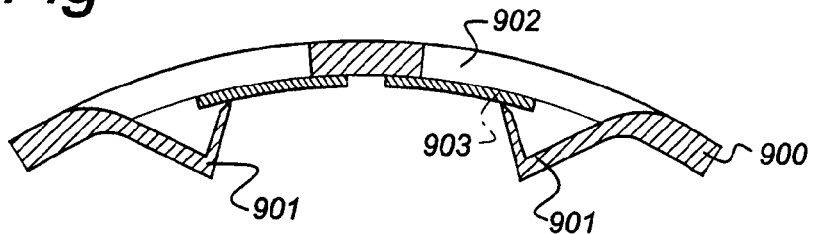
Figure 49C:
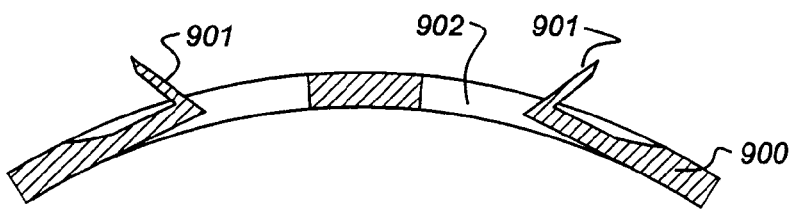
Figure 50A:
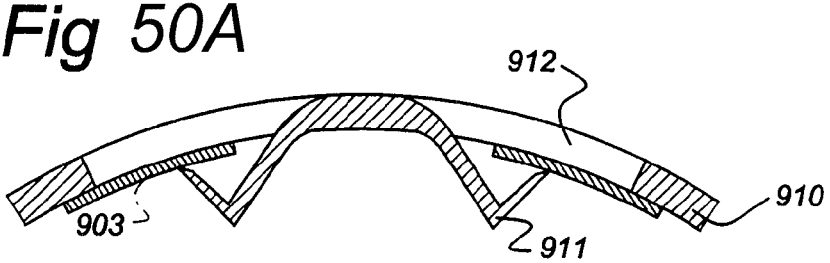
Figure 50B:
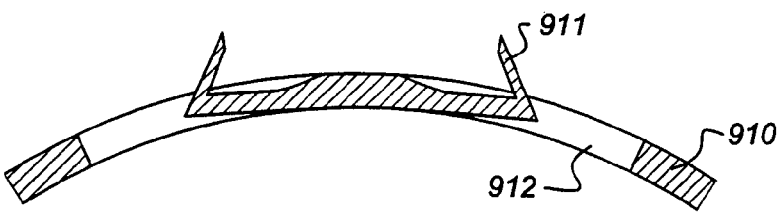
Figure 51A:
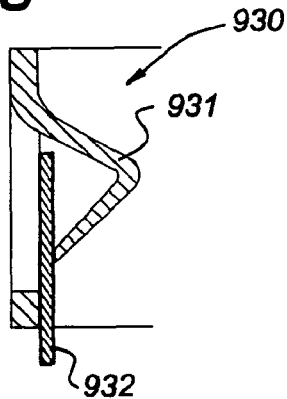
Figure 51B:
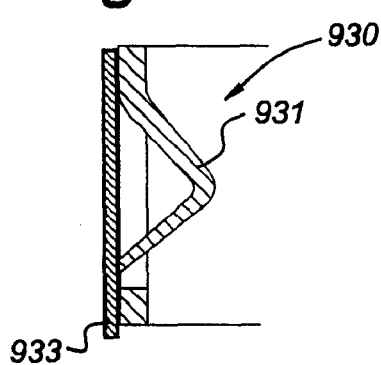
Figure 51C:
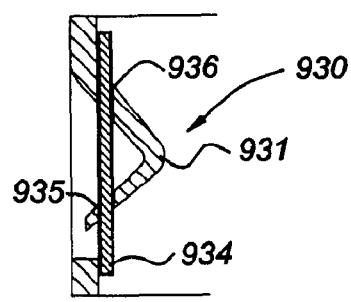
Figure 52:
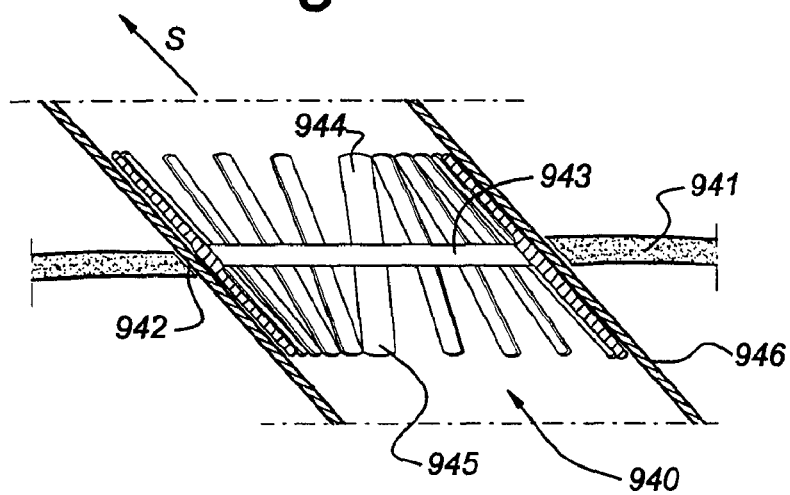
Figure 53:
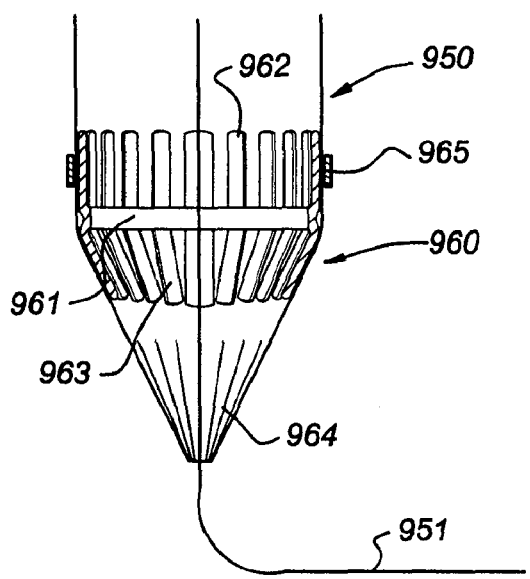

FIG. 33 shows, diagrammatically, as a detail, (approximately the left-hand half of) a longitudinal sectional view of an embodiment of a fixing device according to the first aspect of Section X.4, FIG. 33A showing an axial extended position and FIG. 33B showing a fixing position;

FIG. 34 shows, diagrammatically, as a detail, (approximately the left-hand half of) a longitudinal sectional view of a further embodiment of a fixing device according to the first aspect of Section X.4;

FIG. 35 shows, diagrammatically, as a detail, (approximately the left-hand half of) a longitudinal sectional view of a further embodiment of a fixing device according to the first aspect of Section X.4, FIG. 35A showing a fitting position and FIG. 35B showing a fixing position;

FIG. 36 shows, diagrammatically, as a detail, (approximately the left-hand half of) a longitudinal sectional view of yet a further embodiment of a fixing device according to the first aspect of Section X.4, FIG. 36A showing a fitting position and FIG. 36B showing a fixing position;

FIG. 37 shows, diagrammatically, as a detail, (approximately the left-hand half of) a longitudinal sectional view of an embodiment of a fixing device according to the second aspect of Section X.4, FIG. 37A showing a fitting position and FIG. 37B showing a fixing position;

FIG. 38 shows, diagrammatically, as a detail, (approximately the left-hand half of) a longitudinal sectional view of yet a further embodiment of a fixing device according to the second aspect of Section X.4, FIG. 38A showing a fitting position and FIG. 38B showing a fixing position;

FIG. 39 shows, diagrammatically, as a detail, (approximately the left-hand half of) a longitudinal sectional view of a first embodiment according to the third aspect of Section X.4, FIG. 39A showing a first position and FIG. 39B showing a second position;

FIG. 40 shows, diagrammatically, as a detail, (approximately the left-hand half of) a longitudinal sectional view of yet further embodiments of a fixing device according to the third aspect of Section X.4, FIG. 40A showing the fixing device with a cannula and FIG. 40B showing the fixing device with an obturator cap;

FIG. 41 shows, diagrammatically, as a detail, (approximately the left-hand half of) a longitudinal sectional view of yet a further embodiment of a fixing device according to the third aspect of Section X.4, FIG. 41A showing the fixing device in a first position, FIG. 41B showing the fixing device in a second position and FIG. 41C showing the fixing device in a third position;

FIG. 42 shows, diagrammatically, as a detail, (approximately the right hand half of) a longitudinal sectional view of a further embodiment of a fixing device according to the third aspect of Section X.4, FIG. 42A showing the fixing device in a first position and FIG. 42B showing the fixing device in a second position;

FIG. 43 shows a diagrammatic cross-sectional view of a first embodiment of a fixing device according to a fourth aspect of Section X.4, FIG. 43A showing the fixing device in a first position, FIG. 43B showing the fixing device in a second position and FIG. 43C showing the fixing device in a third position;

FIG. 44 shows a diagrammatic cross-sectional view of a further embodiment of a fixing device according to the fourth aspect of Section X.4;

FIG. 45 shows a diagrammatic cross-sectional view of a further embodiment of a fixing device according to the fourth aspect of Section X.4;

FIG. 46 shows a diagrammatic cross-sectional view of a further embodiment of a fixing device according to the fourth aspect of Section X.4;

FIG. 47 shows, diagrammatically, a plan view of an embodiment according to a fifth aspect of Section X.4, FIG. 47A showing it in a first position and FIG. 47B showing it in a second position;

FIG. 48 shows, diagrammatically, a plan view of a further embodiment according to the fifth aspect of Section X.4, FIG. 48A showing it in a first position and FIG. 48B showing it in a second position;

FIG. 49 shows, diagrammatically, in FIG. 49A a detail view and in FIG. 49B and FIG. 49C radial sectional views of an embodiment according to a sixth aspect of Section X.4;

FIG. 50 shows, diagrammatically, radial sectional views of a further embodiment according to the sixth aspect of Section X.4, FIG. 50A showing it in a first position and FIG. 50B showing it in a second position;

FIG. 51 shows, diagrammatically, axial sectional views of embodiments according to the seventh aspect of Section X.4, FIG. 51A showing it in a first position, FIG. 51B showing it in a second position and FIG. 51C showing it in a third position;

FIG. 52 shows, diagrammatically, an axial sectional view of embodiments according to the eighth aspect of Section X.4;

FIG. 53 shows, diagrammatically, an axial sectional view of an embodiment according to the ninth aspect of Section X.4.

SECTION 3.1

Figure 1A:
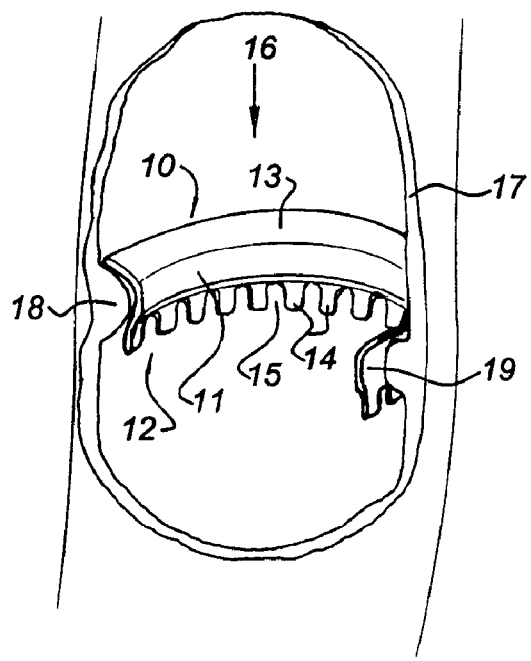
FIG. 1 shows a diagrammatic, perspective view of a first embodiment of a cardiac prosthesis fixing device according to the invention, the bottom flange being in the second position in FIG. 1A and the bottom flange being in the first position in FIG. 1B.
Figure 1B:
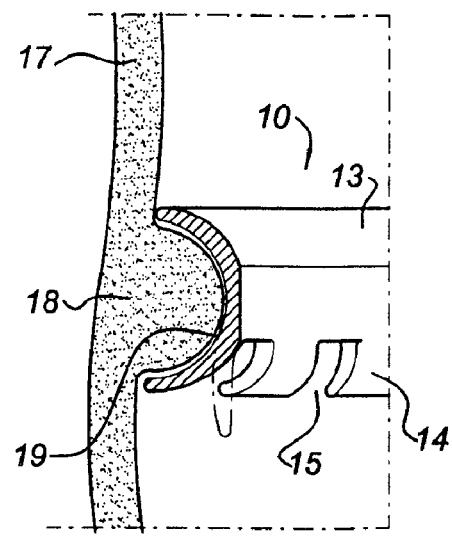

FIG. 1 shows a cardiac prosthesis fixing device in accordance with the invention, intended for fixing a heart valve prosthesis, also referred to as a heart valve fixing device. Said heart valve fixing device 10 consists of a tubular element 11 having a so-called bottom flange 12 and a so-called top flange 13. The top flange 13 extends in an essentially radial direction and is uninterrupted in the peripheral direction of the tubular element 11. Said top flange 13 is permanently in the so-called first position, is essentially rigidly joined to the tubular body 11 and thus cannot be bent with respect to the tubular element 11. The bottom flange 12 is made up of a number of bottom flange segments 14, which are separated from one another by incisions 15. The bottom flange 12 thus forms an interrupted flange extending in the peripheral direction of the tubular element 11. In FIG. 1A the bottom flange 12 is shown in the so-called second position, which is also referred to as the extended position, in which the bottom flange 12 when projected on a diametral cross-sectional surface of the tubular body 11 is located on and/or within the circumference of the tubular body 11. The bottom flange 12 is fixed in said second position, for example by making it from a so-called memory metal, the bottom flange 12 then being frozen in the position shown in FIG. 1A after it has been bent, against resilient force, from the radial position shown in FIG. 1B into the second position shown in FIG. 1A. However, it is also very readily conceivable that the bottom flange 12 has been bent from the first position shown in FIG. 1B into the second position shown in FIG. 1A and has been fixed in said second position by means of a fixing suture, which is not shown, for example a suture as shown in FIG. 12. The second position of the bottom flange 12 makes it possible for the heart valve fixing device 10 to be fed in accordance with arrow 16 to its destination and for the bottom flange 12 to pass through the annulus 18 during this operation, which annulus 18 is located on the inside of a blood vessel 17 or heart. After the heart valve fixing device 10 has been brought into the position shown in FIG. 1A, fixing of the bottom flange 12 in the second position can be released, after which the latter is able to return to the first position shown in FIG. 1B under the influence of the resilient force. In this first position the bottom flange 12 and the top flange 13 enclose the annulus 18 so as to clamp it. The closure between the tubular element 11 and the annulus 18 can, in particular, be improved by providing the outside of the tubular body 11 with a concavity 19 extending in the circumferential direction of the tubular body.

Figure 2A:
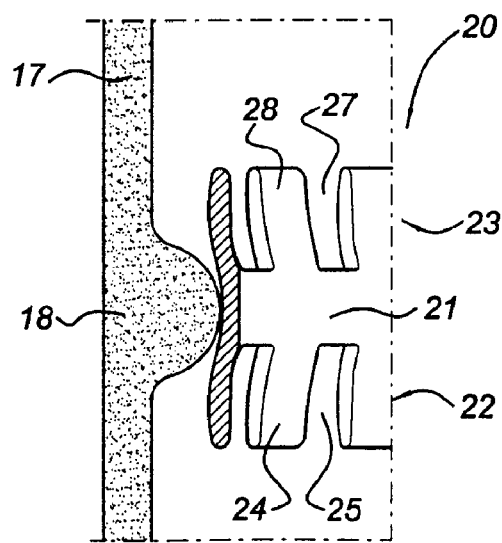
FIG. 2 shows, diagrammatically and in perspective, a second example of an embodiment of a cardiac prosthesis fixing device according to the invention; the bottom and top flanges being in the second position in FIG. 2A and the bottom and top flanges being in the first position in FIG. 2B.
Figure 2B:
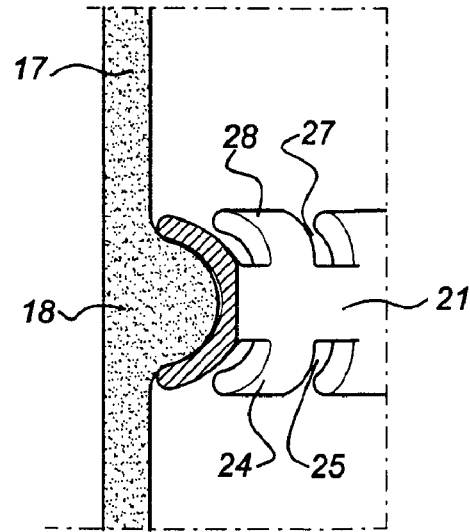

FIG. 2 shows a second embodiment of a heart valve fixing device according to the invention. This second embodiment differs from the first embodiment in FIG. 1 essentially in that in the case of the second embodiment the so-called top flange can also be bent from a first position (shown in FIG. 2B) into a second position (FIG. 2A) against a resilient force in order to position the heart valve fixing device, where, in said second position, the top flange, or at least the projection thereof on a diametral transverse surface of the tubular body, is located within and/or on the periphery of the tubular body. In accordance with FIG. 1, in FIG. 2 the blood vessel or heart is again indicated by 17 and the annulus by 18. Since a substantial proportion of the heart valve fixing device 20 is essentially identical to the heart valve fixing device 10, corresponding reference numerals increased by 10 are used for the heart valve fixing device 20. Although it is not necessarily identical, the top flange 23 in the embodiment according to FIG. 2 is essentially the same as the bottom flange 22. The top flange 23 is made up of flange segments 28 which are separated from one another by incisions 27. The heart valve fixing device 20 can be fed in accordance with arrow 26 to its destination, after which the fixings of the bottom and top flanges can be released and the bottom and top flanges are able to assume their outward-pointing position, shown in FIG. 2B, under the influence of the resilient force. Fixing of the bottom and top flanges in their second position can have been produced by making the heart valve fixing device 20 of memory metal and freezing the bottom and top flanges in a pretensioned, as it were extended, position shown in FIG. 2A. On raising the temperature to above a specific threshold value the bottom and top flanges will then return to their first, outward-pointing position shown in FIG. 2B. The bottom and top flanges can, however, also have been fixed in their second position by means of a suture drawn around them, for example the suture as shown in FIG. 12. However, a sleeve as shown in FIG. 11 can also be used for this fixing. The embodiment of the heart valve fixing device according to FIG. 2 has the additional advantage over the heart valve fixing device 10 in FIG. 1 that as a consequence of both the bottom and the top flanges being in the second position while the heart valve fixing device is brought into position said device is movable with some play S or at least relatively unimpeded, through the blood vessel 17 or heart.

Figure 3:
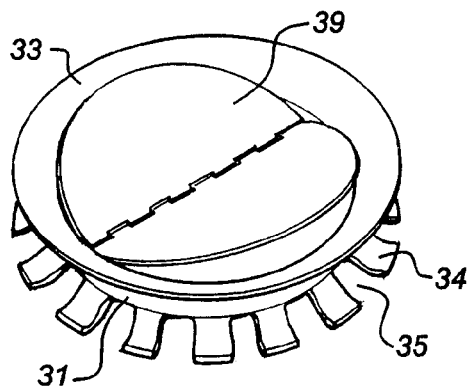
FIG. 3 shows a third illustrative embodiment of a cardiac prosthesis fixing device according to the invention, which is integrated with a two-cusp heart valve prosthesis.

FIG. 3 shows, diagrammatically, a heart valve fixing device 30 with a two-cusp heart valve prosthesis integrated therein. Since, except for the integration of the two-cusp heart valve prosthesis therein, the heart valve fixing device 30 is broadly the same as the heart valve fixing device 20 in FIG. 1, the same reference numerals, increased by 10, have been used for corresponding components. The integrated heart valve prosthesis has two valve cusps 39 which can be rotated about a common axis of rotation.

Figure 4:
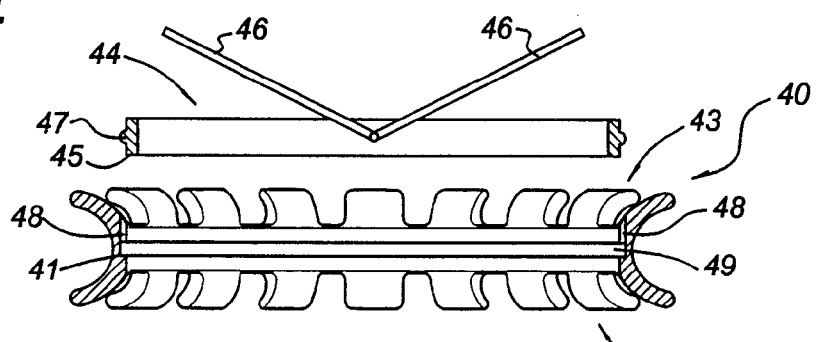
FIG. 4 shows a diagrammatic, perspective view of a fourth embodiment of a cardiac prosthesis fixing device according to the invention, it being possible for a two-cusp heart valve prosthesis with annular or cylindrical housing to be mounted as a separate component in the cardiac prosthesis fixing device according to the invention.

FIG. 4 shows a further variant of a heart valve fixing device 40 according to the invention. Said heart valve fixing device 40 essentially consists of a tubular element 41 which has a bottom flange 42 and top flange 43, both of which are shown in the so-called first position. However, it will be clear that the bottom flange 42 can also assume a so-called second position, whilst this is an optional possibility for the top flange 43. FIG. 4 also shows a heart valve prosthesis 44 consisting of a ring 45 with two valve cusps 46 which can be rotated about a common axis, which heart valve prosthesis is to be considered as conventional per se although it has been modified somewhat in connection with the present invention. The ring 45 can be accommodated inside the tubular element 41 such that it fits tightly. Deviating from the conventional, two projections 47 diametrically opposite one another are provided on the outside of the ring 45. Said projections 47 can each be accommodated in a longitudinal slot 48 in the interior of the tubular element 41. The longitudinal slots 48 terminate in a peripheral groove 49, in which the projections 47 can likewise be accommodated. In this way the valve prosthesis 44 is fixable by a sort of bayonet fitting in the tubular element 41 and, moreover, can be turned in the tubular element 41 in order to be able to position the valve prosthesis 44 correctly as required by the circumstances. When the valve prosthesis 44 has been positioned in its correct position it can be locked with respect to the tubular element 41 using means which are not shown, such as, for example, the locking screw or some other means.

In contrast to what is conventional it is possible according to this invention, as may easily be seen from FIG. 4, to provide an assembly of heart valve fixing device 40 and valve prosthesis 44, in which case during implantation the heart valve fixing device 40 is first positioned and fixed to the annulus and only then is the valve prosthesis 44 positioned and fixed in the heart valve fixing device 40. In order to make such a valve prosthesis assembly possible at a later date, modifications to the conventional are required. Thus, according to the invention the following can be provided:

- some form of bottom stop, such as a stop ridge formed on the inside and at the bottom of the tubular element 41, which stop ridge prevents the valve prosthesis from being able to become detached from the tubular element in the downward direction; and/or
- some form of top closure, such as a capping ring or resilient snap-fit lips, which prevents (prevent) the valve prosthesis from being able to become detached from the tubular element in the upward direction; and/or
- interacting means on, on the one hand, the inside of the tubular element and, on the other hand, the outside of the valve prosthesis housing, which means, for example, provide for axial enclosure of the valve prosthesis in the tubular element and/or, for example, allow rotation of the valve prosthesis in the tubular element, such as, for example, interacting screw threads, a bayonet fitting, snap-fit means, etc.

Figure 5:
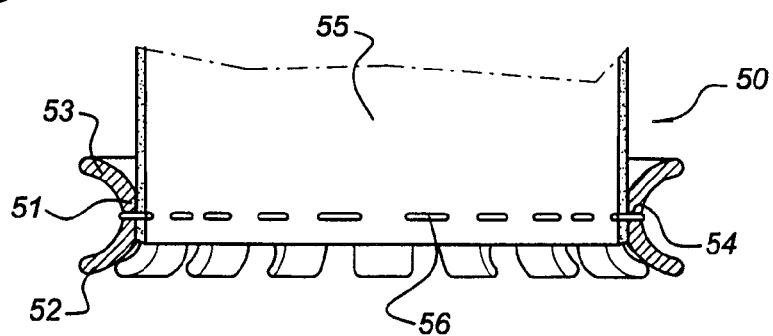
FIG. 5 shows a diagrammatic view of a fifth embodiment of a cardiac prosthesis fixing device according to the invention, it being possible to attach a biological heart valve prosthesis, which may or may not have a stent, to the cardiac prosthesis fixing device by suturing.

FIG. 5 shows, as a further embodiment, a heart valve fixing device 50 according to the invention. Said heart valve fixing device 50 comprises a tubular element 51, a bottom flange 52 and a top flange 53. A ring of suture passages 54 has been made in the tubular element 51. An animal or human donor heart valve prosthesis 55, which may or may not have been provided with a stent, can be fixed in this heart valve fixing device 50 by means of suturing. The suture 56 can be inserted and threaded through the suture passages 54 and the lower section of the prosthesis 55. In this case the donor heart valve prosthesis 55 can consist of a blood vessel section in which an original heart valve is still present.

With reference to FIG. 5 it will be clear that fixing of the biological donor heart valve prosthesis 55 to the heart valve fixing device 50 can also take place prior to positioning the heart valve fixing device 50 in the heart. Furthermore, it is possible to secure an animal or human donor prosthesis, such as no. 55 in FIG. 5, to the prosthesis fixing device according to the invention by means of a locking tie or ligature. For this purpose the tubular body could be extended beyond one of the flanges, it then being possible to insert the extension in a donor prosthesis 55 and to fit the locking tie or ligature around the overlapping section of extension and donor prosthesis. Furthermore, it is possible to fix the biological valve between one or more flanges to the inside of or on top of the tubular element. It is also possible to fix a flexible ring to the bottom of the biological valve, which ring is clamped in a recess in the inside of the tubular element.

Figure 6:
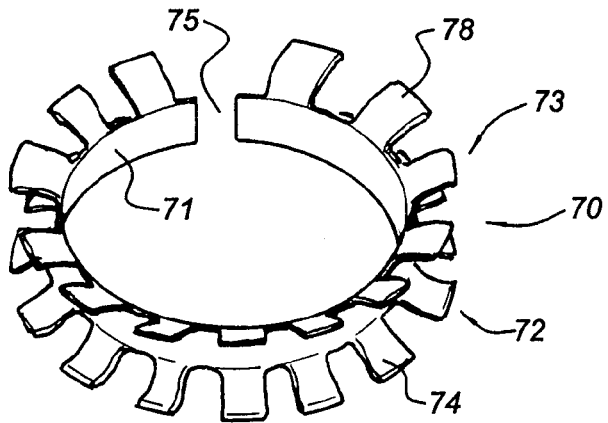
FIG. 6 shows a sixth example of a variant of a cardiac prosthesis fixing device according to the invention and specifically shows an annular prosthesis for repairing, and in particular constricting, a leaking heart valve, such as a mitral valve.

FIG. 6 shows an example of a cardiac prosthesis fixing device 70 in the form of the so-called ring prosthesis for narrowing the diameter of the opening of a leaking valve. In practice an operation of this type is mainly carried out on mitral and tricuspid valves, although it could optionally also be carried out on other heart valves. The heart valve fixing device 70 consists of a tubular element 71 which is bean-shaped in the peripheral direction but is not completely closed, as can be seen at 75 in FIG. 6. The tubular element 71 is provided with a highly segmented bottom flange 72 and a highly segmented top flange 73. The bottom flange 72 is made up of bottom flange segments 74 arranged relatively far apart in the peripheral direction and associated top flange segments 78. The tubular element 71 can optionally be a ring which is closed in the peripheral direction.

FIG. 7 relates in particular to a so-called aortic valve. By way of illustration, FIG. 7A shows an exposed, perspective view of the wave-shaped annulus of the aortic valve. In this figure, 17 indicates the aorta wall and 18 the aorta annulus.

Figure 7A:
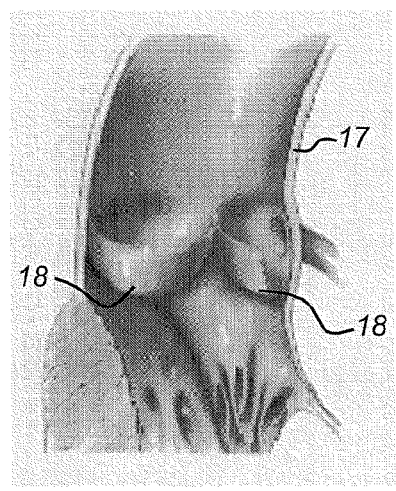
FIG. 7A shows, diagrammatically, an exposed view of the wave-shaped annulus of an aortic valve.
Figure 7B:
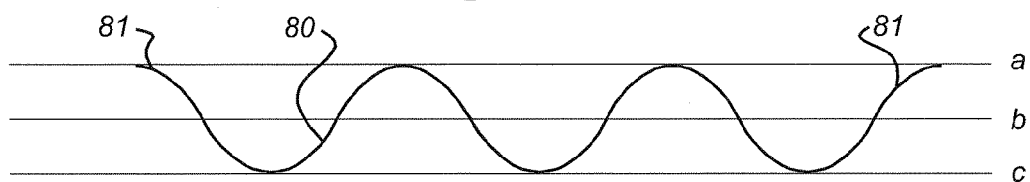
FIG. 7B shows, diagrammatically, a wave-shaped annulus of an aortic valve laid out in a flat plane.

For further illustration, FIG. 7B shows, diagrammatically, the wave-shaped annulus 80 of an aortic valve laid out in a flat plane. This view can be regarded as a view of a section of the aorta which has been cut open in the longitudinal direction and then has been laid out in a flat plane. The horizontal line a in FIG. 7B indicates the height of the peaks of the wave-shaped annulus 80, which are also referred to as the commissuras. The horizontal line c indicates the depth of the troughs of the wave-shaped annulus 80. The horizontal line b indicates the height of the origins of the wave-shaped annulus 80. As may be seen from FIG. 7B, the wave-shaped annulus 80 of the aortic valve is to be regarded as a sine wave-shaped annulus with a length of 3 wave periods. The start and end points of the sine wave-shaped annulus 80 in FIG. 7B are each indicated by 81, since these are in fact the same point in the annulus 80, that is to say the point where the latter has been cut through for the purposes of the flat extended representation.

Figure 7C:
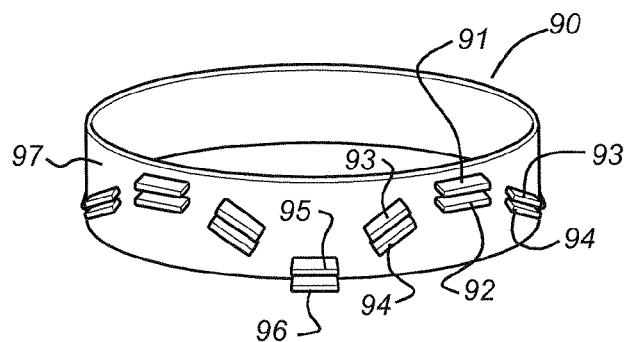
FIG. 7C shows, highly diagrammatically, a seventh embodiment of a cardiac prosthesis fixing device according to the invention.

FIG. 7C shows, as a further illustrative embodiment, a heart valve fixing device 90 which in particular is suitable for fixing an aortic heart valve prosthesis. The heart valve fixing device 90 consists of a tubular element 97 with three types of bottom flange/top flange pairs arranged distributed over the periphery thereof. Bottom flange/top flange pairs 91, 92 are provided at the height of the level line a (corresponding to the level line a in FIG. 7B) for clamping the commissuras of the annulus 80. Top flange/bottom flange pairs 95, 96 are provided at the level line c (corresponding to the level line c in FIG. 7B) for clamping the troughs of the valve annulus 80. Bottom flange/top flange pairs 93, 94 are provided at the level line b (corresponding to the level line b in FIG. 7B) for clamping the origins of the wave-shaped annulus 80. Viewed in the circumferential direction of the tubular element 97, the flange pairs 91, 92 are arranged 120° apart, the flange pairs 96 and 95 are arranged 120° apart and the flange pairs 93, 94 are arranged 60° apart. Although in general 12 flange pairs 91, 92, 93, 94, 95 and 96 will preferably be used, an arbitrary combination of flange pairs at levels a, b and c can be chosen depending on the circumstances, which can be highly patient-dependent.

Figure 7D:
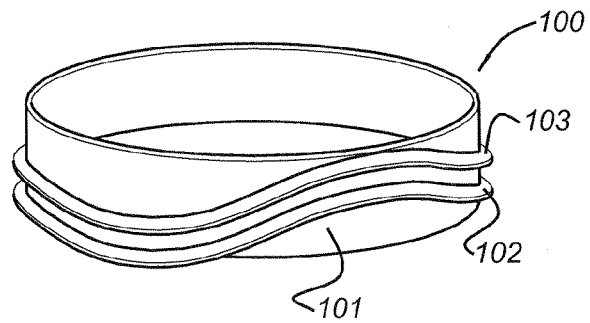
FIG. 7D shows, highly diagrammatically, an eighth embodiment of a cardiac prosthesis fixing device according to the invention.

FIG. 7D shows a highly diagrammatic representation of a further embodiment of a heart valve fixing device, specifically a heart valve fixing device 100. Heart valve fixing device 100 is somewhat similar to heart valve fixing device 90 in FIG. 7C. Heart valve fixing device 100 consists of a tubular element 101, a bottom flange 102, to be regarded more or less as continuous, and a top flange 103, to be regarded more or less as continuous. As can be seen, the bottom flange 102 and top flange 103 follow a sine wave pattern over the circumference of the tubular element 101. Since, certainly in the case of the bottom flange and optionally also the top flange being bendable between a first and a second position and vice versa, this is less easy to achieve in practice with a flange extending continuously over the circumference of the tubular element 101, the bottom flange 102 and, where appropriate, the top flange 103 will have been made essentially discontinuous by means of, for example, radial incisions.

The embodiment according to FIG. 7D offers the major advantage that a good seal on the sine wave-shaped valve annulus of an aortic valve can be ensured to a large extent.

Figure 8A:
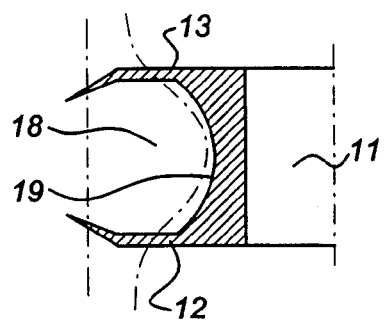
FIG. 8A showing a first variant and FIG. 8B showing a second variant.
Figure 8B:
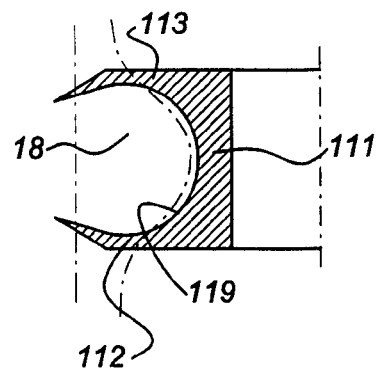
FIG. 8 shows a diagrammatic cross-section of two details of further variant embodiments of a cardiac prosthesis fixing device according to the invention.

By way of illustration, FIG. 8A shows, as a detail, the clamping/enclosure of the annulus 18 according to FIG. 1B. It can clearly be seen from the detail in FIG. 8A that the tubular body can have been provided on its outside with a concavity 19, which ensures a good seal on the annulus 18. FIG. 8B shows a variant of FIG. 8A. The tubular body is indicated by 111, the top flange by 113 and the bottom flange by 112. FIG. 8B shows that the concavity 119 continues into the bottom and top flanges. With this arrangement the top flange 113 and bottom flange 112 can each be bendable into a so-called second position. As is further illustrated in FIGS. 8A and 8B, the bottom and top flanges can have been provided at their periphery with fingers or pins which pierce the tissue behind and/or adjacent to the annulus.

FIG. 9 shows a number of embodiments with which the inner and outer flanges are formed by fingers arranged on support arms, the support arms themselves being bendable in order to be able to bend the top and bottom flanges between a first and a second position.

Figure 9A:
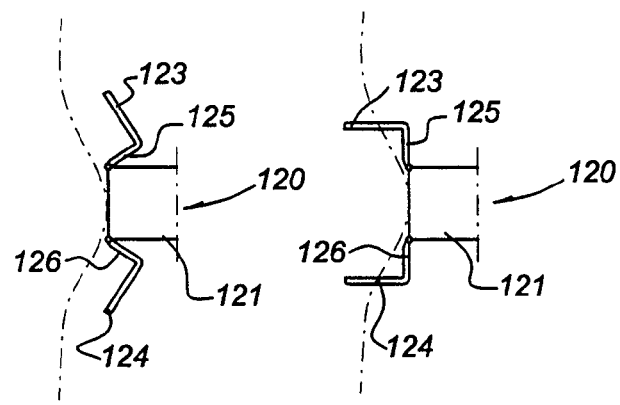
FIG. 9A shows, diagrammatically and in perspective, a ninth embodiment of a cardiac prosthesis fixing device according to the invention.

FIG. 9A shows a tubular body 121 which has a number of top flange fingers 123 and bottom flange fingers 124 (only two of each type are shown but in practice several of each type will have been provided distributed around the periphery). The top flange fingers 123 are arranged on arms 125 and the bottom flange fingers 124 are arranged on arms 126. On the left of FIG. 9A the heart valve fixing device 120 is shown with the bottom and top flange fingers in the so-called second position and on the right in FIG. 9A the heart valve fixing device 120 is shown with the bottom and top flange fingers in the so-called first position. If the arms 125 and top flange fingers 123 are of equal length and the arms 126 and bottom flange fingers 124 are of equal length, the arms 125 and 126 will have to be bent through at least 45° in order to move the bottom flange fingers and top flange fingers between the first and the second position.

Figure 9B:
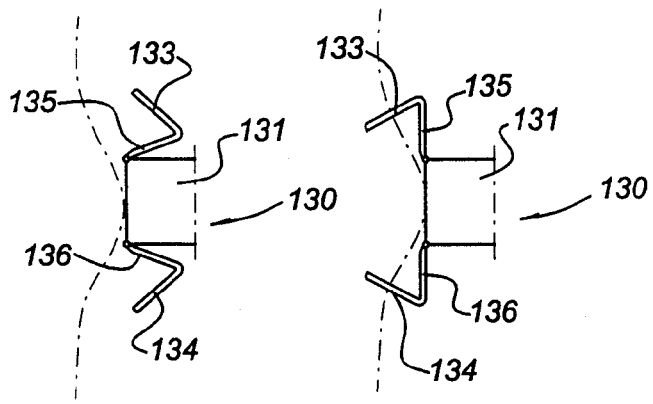
FIG. 9B shows, diagrammatically and in perspective, a tenth embodiment of a cardiac prosthesis fixing device according to the invention.

FIG. 9B shows a variant of FIG. 9A. Corresponding components are indicated in FIG. 9B using the reference numeral from FIG. 9A plus 10. In order to move the bottom flange fingers 134 and top flange fingers 133 from the so-called second position, shown on the left, into the so-called first position, shown on the right, the arms 135 and 136 must bend back through 90° under the influence of resilient force. What is achieved by allowing the bottom flange fingers 134 and top flange fingers 133 to point towards one another obliquely in the so-called first position is that said fingers are able to pierce the tissue, in particular the valve annulus, and thus further fix the heart valve fixing device 130.

Figure 9C:
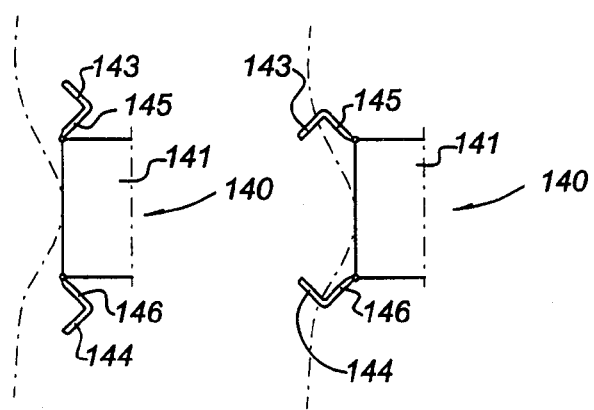
FIG. 9C shows, in cross-section, a diagrammatic detail of an eleventh embodiment of a cardiac prosthesis fixing device according to the invention.

FIG. 9C shows a further variant of FIGS. 9B and 9A. Compared with FIG. 9B the reference numerals for corresponding components have again been increased by 10. The heart valve fixing device 140 in FIG. 9C differs from the heart valve fixing device 120 in FIG. 9A essentially in that the support arms 145 and 146 point inwards at 45° with respect to the tubular element 141 in the so-called first position and point outwards at 45° with respect to the tubular element in the so-called second position. The embodiment according to FIG. 9C will, in particular, be advantageous in the case of a more pronounced annulus. For a less pronounced, relatively flat annulus or in a blood vessel (without annulus) the preference will be for the embodiments according to FIGS. 9A, 9B and FIG. 9D, which is to be discussed below.

Figure 9D:
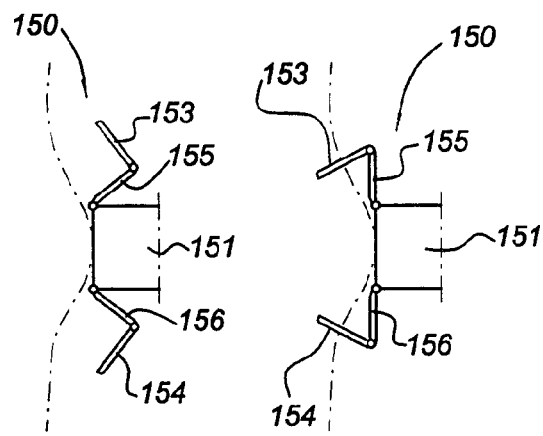
FIG. 9D shows, in diagrammatic cross-section, a detail of a twelfth embodiment of a cardiac prosthesis fixing device according to the invention.

FIG. 9D shows yet a further variant of a heart valve fixing device 150, corresponding components again being indicated by reference numerals increased by 10 compared with those used in FIG. 9C. The difference compared with the embodiments according to FIGS. 9A-9C is that in the case of the heart valve fixing device 150 according to FIG. 9D not only the arms 155 and 156 but also the bottom flanges 154 and top flanges 153 are bent with respect to the tubular element 151. Bottom flange fingers 154 bend towards the associated support arm 156 under the influence of a pretension when moving from the so-called second position (on the left) to the so-called first position (on the right). The same also applies in the case of the top flange finger 153, which bends towards the support arm 155 during this movement.

Figure 10:
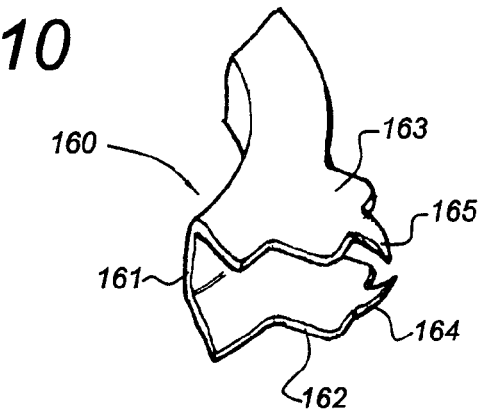
FIG. 10 shows, in perspective, a detail of a thirteenth embodiment of a cardiac prosthesis fixing device according to the invention.

FIG. 10 shows a detail of a heart valve fixing device 160. Said heart valve fixing device 160 consists of a tubular element 161, a number of bottom flange segments 162 arranged distributed over the periphery of said tubular element and a number of top flange segments 163 arranged distributed over the periphery of the tubular element. The bottom flange segments 162 and top flange segments 163 are each provided with points 164 and 165, respectively, which in the first position shown point towards one another and which are able to anchor in the tissue, in particular the valve annulus. In the case of the heart valve fixing device 160 shown in FIG. 10, in any event the bottom flange segments 162 can be bent against a resilient force from the so-called first position shown into a so-called second position and optionally the top flange segments 163 can also be bent against a resilient force from the so-called first position shown into a so-called second position. By making the flange segments broader or continuous or virtually continuous in the centre and making the peripheral sections narrower, the sealing ability of the centre is improved and the piercing ability of the periphery is improved.

FIG. 11 shows a heart valve fixing device with a two-cusp heart valve prosthesis mounted therein beforehand. FIG. 11A shows the heart valve fixing device 170, which as such can readily be compared with the heart valve fixing device 20 in FIG. 2A or the heart valve fixing device 30 in FIG. 3, in a position ready for fitting. The heart valve fixing device 170 comprises a tubular element 171, bottom flange segments or flange fingers 172 and top flange segments or flange fingers 173. In FIG. 11A the bottom flange fingers 172 and top flange fingers 173 are shown in the so-called second position, in which they are, as it were, stretched in the longitudinal direction of the tubular element 171 and under pretension for bending outwards. The bottom flange fingers 172 and top flange fingers 173 are held in an extended, so-called second position by means of a sleeve 175 arranged around the whole. After the whole has been brought into position inside the valve annulus to which the heart valve fixing device 170 has to be fixed, the sleeve 175 can be pulled upwards, as is shown by arrow 176, which is shown diagrammatically in FIG. 11B. After pulling away the sleeve 175 the bottom flange fingers 172 and top flange fingers 173 will spring back into their first position.

FIG. 12 shows a heart valve fixing device 180 consisting of a tubular element 181 and bottom flange fingers 182 provided with anchoring points 183. The bottom flange fingers 182 are shown in the so-called second position. The bottom flange fingers 182 are held in this second position by means of a suture 184, which extends stretched tautly around the bottom flange fingers 182. The suture 184 overlaps itself in the region 186, it being possible for the suture to be fed behind the next flange finger after it has passed flange finger 188 in order to be guided out towards the front through a tube 185 or, instead of a tube, through a small conduit made in the wall of the tubular element, after which the ends of the suture can be held stretched taut at 187 by means of a knot or the like. After the heart valve fixing device 180 has been positioned in place inside the annulus 18, one knot 187, for example, can then be cut off or otherwise removed and the suture 184 can then be pulled out completely by means of the other knotted end 187, the suture 184 being guided within the tubes 185 on passing through the annulus 18 and thus not acting on or cutting into the annulus 18. The tubes 185 run along the outside of the tubular element 181. If the fixing by means of the bottom flange fingers 182 and anchoring points 183 is sufficiently firm, the so-called top flange can optionally be dispensed with in its entirety. In this case the so-called bottom flange can optionally also be fitted as a top flange during implantation. This top flange can still be fixed to the tubular element 181 even after fitting the tubular element 181, for example by screwing on, if appropriate only after removing the suture 184. The so-called top flange, which is not shown in FIG. 12, can also form an integral whole with the tubular element and be temporarily held in the so-called second or extended position by, for example, once again a suture or ligature, in order to facilitate positioning inside the annulus.

FIG. 13 shows, highly diagrammatically, that folding the bottom flange or bottom flange segments outwards from the so-called second position into the first position can be assisted by means of push elements 195, which can be moved outwards in the radial direction.

With regard to accommodating the valve annulus between the top and bottom flange for fixing it is also pointed out in particular that the valve annulus is not always equally pronounced. In practice the valve annulus can even be a barely discernible narrowing on the inside of the blood vessel or the heart or, in the case of the removal of the natural heart valve cusps, can have been cut away to a greater or lesser extent. In the case of a relatively little pronounced annulus, such as, for example, is naturally the case with aortic valves which have a relatively flat or plane annulus, the bottom and top flanges according to the invention will grip the annulus or the remainder thereof, as, for example, can be seen in FIG. 14, in particular on the left, rather than clamp the annulus between them. However, according to the invention "accommodation of the valve annulus between the bottom and top flanges for fixing the cardiac prosthesis fixing device" must be understood to cover this case as well. In the case of fairly flat annuli, such as is naturally the case with aortic valves, the bottom and top flanges will advantageously, by means of arms or other projecting elements, pierce the tissue around, below and above the annulus. To illustrate this, FIG. 14 shows, diagrammatically, a mitral valve prosthesis device according to the invention. In the case of the mitral valve the natural annulus is conical over three quarters of the periphery on either side of an imaginary horizontal cross-sectional surface (see left-hand side of FIG. 14). One quarter of the annulus is very thin and this ultimately forms only a partition between two hollow spaces, which partition is at approximately 60° to the vertical. A mitral valve prosthesis fixing device according to the invention, such as is indicated diagrammatically by 200 in FIG. 14, will then have a bottom flange edge 202 and top flange 201 over three quarters of the periphery, which flange edge 202 and top flange 201 preferably bear at least periphery anchoring points 203. The bottom flange edge 202 and top flange 201 can be of approximately the same construction over said three quarters of the periphery. For the remaining quarter of the periphery it will be advantageous for good fixing of the mitral valve prosthesis fixing device according to the invention if the bottom flange 205 makes an acute upward angle with respect to the tubular element 207 when it is in the first position. The bottom flange 205 can also optionally be made longer at this location.

SECTION 3.2

FIG. 15 shows a prosthesis fixing device 410, in particular a cardiac prosthesis fixing device consisting of a tubular, in general cylindrical, element 416 having slit-shaped passages 413 arranged distributed around the periphery, and, per passage 413, an arm 411 extending from the top of the slit-shaped passage 413 obliquely inwards and downwards (at least according to FIG. 15), which arm bears at its end an outward-pointing pin 412 which, at least in the embodiment according to FIG. 15, is approximately at right angles to the arm 411.

FIG. 15 also shows a valve prosthesis, also shown in section, above the cardiac prosthesis fixing device 410. The valve prosthesis consists of a cylindrical body 417 with the valve cusps 419 hingeably mounted therein. The cylindrical body 417 is provided on its outer periphery with four ridges 418 arranged distributed around said outer periphery. The cardiac prosthesis fixing device 410 is provided with four axial slots 414, formed in the interior, which are arranged distributed—in the same way as the ridges 418—over the inner periphery of the cardiac prosthesis fixing device 410. The slots 414 open into an interior peripheral groove 415. The cardiac prosthesis can be fitted in the cardiac prosthesis fixing device by positioning the ridges 418 above the respective slots 414 and then allowing the valve prosthesis to lower into the valve prosthesis fixing device until the ridges 418 are located in the peripheral grooves 415. The valve prosthesis can then be turned into a desired position and fixed in the desired position by means of fixing means, which are not shown.

The cardiac prosthesis fixing device is intended to be fixed in the interior of the circulatory system in contact with the peripheral wall of a part thereof. To this end the cardiac prosthesis fixing device is usually fed through a section of the circulatory system to its destination. This is carried out with the arms 411 and pins 412 in the position as shown in FIG. 15 and FIG. 15A. Once the device is at its destination, pressure is exerted by means of an aid, such as a balloon, float element or valve prosthesis, from the inside on the arms 411 in order to push these outwards or, to put it more accurately, to swing them about the fold/bending line which extends in the tangential direction and is at the level of the top of the passage 413. In this way the pin 412 which initially is located inside the tubular element 416 emerges in order to penetrate the surrounding tissue and thus to anchor the cardiac prosthesis fixing device 410 in the surrounding tissue.

This outward pushing or outward swinging of the arms 411 with pins 412 can be effected by pushing the arms 411 outwards, always one arm at a time or optionally a few arms 411 at a time, by means of one or other suitable tool. It is also conceivable to insert a balloon until it is inside the tubular element 416 and to inflate this balloon in order to push all arms 411 with pins 412 outwards at the same time. However, it is also possible to perform this outward pushing of the arms 411 with pins 412 at the same time as positioning the valve prosthesis. When the valve prosthesis, viewed according to FIG. 15, is slid into the cardiac prosthesis fixing device 410 from above, the bottom edge of the cylindrical body 417 will gradually push the arms 411 further outwards until the arms 411 are located entirely in contact with or in the tubular element 416, in which latter case they are located within the passages 413. It is optionally also conceivable that the arms 411 with pins 412 have been initially pushed/swung partly or substantially outwards using a tool and that this outward pushing/swinging is completed on fitting the valve prosthesis in the cardiac prosthesis fixing device 410.

FIG. 15A shows a detail a from FIG. 15, where it can clearly be seen that in the so-called insertion position the arms 411 with pins 412 are located completely within the tubular element 416. In FIG. 15B the so-called fixing position is shown and the swinging movement of the arm 411 with pin 412 is indicated by means of an arrow.

FIGS. 16A and 16B show, as a detail corresponding to FIGS. 15A and 15B respectively, a variant of a cardiac prosthesis fixing device according to FIG. 15. The cardiac prosthesis fixing device is indicated in its entirety by 420, the peripheral groove is indicated by 425 (compare 415 in FIG. 15), the passage is indicated by 423 (compare 413 in FIG. 15), the arm is indicated by 421 (compare 411 in FIG. 15) and a bottom pin is indicated by 422 (compare 412 in FIG. 15). The embodiment according to FIGS. 16A and 16B essentially differs from that in FIGS. 15A and 15B in that the arm 421 is provided with a second pin, or top pin 426. The pin 426 is shorter than pin 422, although if the arm 421 were to be bent further inwards pin 426 could also be the same length as pin 422. The additional pin 426 improves the anchoring in the surrounding tissue. It should be clear that more pins per arm 421 can also be provided. For example, consideration can be given to three or four pins per arm 421.

As a variant on the arm 421 with two pins 422, 426 it is also very readily conceivable to attach/provide the pins 422 and 426 each on a separate arm. This can then, for example, lead to an embodiment as in FIG. 18. However, instead of the embodiment according to FIG. 18 with arms oriented in opposing directions, it is also very readily conceivable that the arms are oriented in the same direction, it then being possible for the pins 426 to be mounted on shorter arms than the pins 422 (see, for example, FIGS. 24A and 24B) or the hinge axes of the arms bearing the pins 426 located at the top being located above the hinge axes of the arms bearing the pins 422 located at the bottom. It is also very well possible that the arms of the top pins 426 come to lie completely above those of the bottom pins 422 and thus two rows of arms with pins, located above one another, are formed (see, for example, FIGS. 23A and 23B). For an explanation of the variants just mentioned reference is made to FIGS. 23A and 23B and FIGS. 24A and 24B.

FIGS. 23A and 23B show, as a detail corresponding to FIGS. 15A and 15B, respectively, a variant of the cardiac prosthesis fixing device according to the invention. In the variant according to FIGS. 23A and 23B there are two rows of arms, provided with pins, positioned above one another in the peripheral direction of the tubular element. The top row consists of arms 491 with pins 496 and the bottom row of arms 494 with pins 492. Slits 497 are provided for the arms 491 with pins 496 and slits 493 are provided for the arms 494 with pins 492. Groove 495 is for fixing, for example, a valve prosthesis, in accordance with what is known from FIG. 15; compare groove 415 in the latter figure.

FIGS. 24A and 24B show a corresponding variant, but now with a double row of arms, provided with pins, which as it were are located within one another instead of above one another. The so-called hinge axes of the short arms 501 and the long arms 504 are essentially at the same level or at least approximately at the same level. However, it is also conceivable that the hinge axes for the arms 501 are located substantially lower than those for the arms 504, the arms 501, with pins 506, then coming to lie, as it were, completely within the arms 504 with pins 502. If the hinge axes for the arms 501 and 504 are essentially in an identical location, a common groove 505 can then in each case be provided for the arms 501 with pins 506 and arms 504 with pins 502. Groove 505 is again comparable with groove 415 in FIG. 15.

FIGS. 17A and 17B show, again as a detail corresponding to that in FIGS. 15A and 15B, respectively, a variant of a cardiac prosthesis fixing device according to the invention. The cardiac prosthesis fixing device is indicated in its entirety by 430; 435 indicates the peripheral groove (compare 415 in FIG. 15); 431 indicates the arm (compare 411 in FIG. 15); 432 indicates the pin (compare 412 in FIG. 15); 433 indicates the passage (compare 413 in FIG. 15). The difference between the embodiment according to FIGS. 17A and 17B and the embodiment according to FIGS. 15, 15A and 15B essentially lies in the shape of the pin 432 and to a lesser extent in the shape of the arm 431. As can be seen in particular from FIG. 17A, the arm 431 is curved slightly inwards and the pin 432 is curved fairly pronouncedly outwards, preferably in accordance with an arc of a circle. Such a curvature of, in particular, the pin 432 makes penetration of the tissue in accordance with a circular path possible, minimal damage occurring to the surrounding tissue.

FIG. 18 shows by way of a detail sectional view yet a further variant of a cardiac prosthesis fixing device according to the invention. This detail can as such be compared with the details in FIGS. 15A, 15B, 16A, 16B, 17A, and 17B. Corresponding to the embodiment in FIGS. 15, 15A and 15B, the cardiac prosthesis fixing device 440 according to FIG. 18 is provided with an arm 441 with a pin 442 at the end. However, a significant difference compared with the embodiment according to FIGS. 15, 15A and 15B is that the cardiac prosthesis fixing device 440 is also provided with arms 443 which are oriented in the opposite direction to arms 441 and are provided with pins 444 at the free end. The arms 441 with pins 442 and the arms 443 with pins 444 will preferably be arranged distributed over the periphery of the cardiac prosthesis fixing device 440 such that they alternate with one another. Separate passages can in each case have been formed in the tubular element for the arms 441 with pins 442 and for the arms 443 with pins 444, but it is also conceivable, as is shown in FIG. 18, to provide a single common passage 448 for each pair of adjacent arms 441 and 443. The embodiment according to FIG. 18 further differs from that according to FIGS. 15, 15A and 15B in that a relatively short, outward-pointing peripheral flange 447 is provided at the bottom and a relatively longer, outward-pointing flange 446 is provided at the top. The task of said flanges 447 and 446 is to enclose the annulus tissue 445 of a faulty natural heart valve to some extent. The cardiac prosthesis fixing device 440 further differs from the cardiac prosthesis fixing device 410 in that the external peripheral surface of the tubular element is provided with a concave recess 449 extending in the peripheral direction. This concavity 449 ensures better abutment with the surrounding annulus tissue 445.

To summarise, the cardiac prosthesis fixing device 440 differs from the cardiac prosthesis fixing device 410 in respect of three aspects. These aspects are:
a) the arms 441, 443 oriented in opposing directions;
b) the bottom flange 447 and the top flange 446; and
c) the concavity 449.

It should be clear that it is in no way essential for these three differences a), b) and c) all to occur together in combination in one embodiment. These differences a), b) and c) can also be employed, each individually or in combination with another, in any other embodiment of the cardiac prosthesis fixing device according to the invention.

In FIG. 18 the arm 441 with pin 442 is shown in the so-called fixing position, whereas the arm 443 with pin 444 is shown in the so-called insertion position. With the use of suitable tools it is possible first to swing the arms 441 with pins 442 outwards and only thereafter the arms 443 with pins 444, or vice versa. However, it is also very readily possible, for example using the abovementioned balloon or other tool driven by compressed air or manually, to swing the arms 441 with pins 442 and arms 443 with pins 444 outwards at the same time.

FIG. 19 shows a cardiac prosthesis fixing device 450 which is largely identical to the cardiac prosthesis fixing device 410. 451 indicates the tubular element (compare 416), 452 the arms (compare 411), 453 the pins (compare 412) and 454 the passages (compare 413).

FIG. 19 further shows an auxiliary element 458 for pushing/swinging the arms 452 with pins 453 outwards. The auxiliary element 458 consists of a pull element 455 which can be pulled upwards in accordance with the arrow, viewed in, in accordance with FIG. 19, in order to pull the forcing body 456 inside the cardiac prosthesis fixing device 450 or at least inside the tubular element 451. When this takes place the arms 452 will be pressed outwards by the forcing body 456 and the pins 453 will thus penetrate the surrounding tissue. A nose-piece 457 which is spherical at the bottom has been formed on the underside of the forcing body 456, viewed in accordance with FIG. 19. Said nosepiece 457 facilitates feeding of the tool 458 through the circulatory system to the destination. It is possible that the cardiac prosthesis fixing device 450 has already been fitted around the pull element 455 before this operation, but it is also possible first to bring the tool 458 to the destination and then to bring the cardiac prosthesis fixing device, slid over the pull element 455, along the pull element 455 to its destination. When pulling on the pull element 455 the direction of pull will preferably be directed away from the heart.

FIGS. 20A and 20B show details corresponding to FIGS. 15A and 15B, respectively, of a further variant of the cardiac prosthesis fixing device, specifically cardiac prosthesis fixing device 460 according to the invention. 461 indicates the passages (compare 413), 462 the arms (compare 411) and 463 the pins (compare 412). The difference compared with the embodiment according to FIGS. 15, 15A, 15B, 16A, 16B, 17A, 17B and 19 essentially lies in the top flange 464 and/or bottom flange 465. The top flange 464 and bottom flange 465 do not necessarily both have to be present. In the so-called insertion position, shown in FIG. 20A, the top flange 464 and bottom flange 465 are in the so-called extended position. Both the top flange 464 and bottom flange 465 consist of flange fingers which are separated from one another by incisions. When the cardiac prosthesis fixing device 460 has been positioned in its place inside the valve annulus 467 which is still present on the inside of the circulatory system 466, the top flange fingers 464, bottom flange fingers 465 and arms 462 are swung outwards. This can be carried out in an arbitrary sequence, for example the arms 462 with pins 463, then the bottom flange fingers 465 and then the top flange fingers 464, but it is also possible for all to be swung outwards simultaneously or for just the bottom and top flange fingers to be swung outwards simultaneously. The top and bottom flange fingers 464 and 465, respectively, can be swung outwards by forcing, bending taking place. It is also conceivable that the extended position of the top flange fingers 464 and bottom flange fingers 465 is a position in which these are under a pretension tending to swing outwards and have been fixed in said pretensioned position. This fixing can then be released, for example by removing a physical impediment or in the case of, for example, memory metals, such as nickel-titanium alloys, by heating to above a certain temperature. FIG. 20B shows the cardiac prosthesis fixing device 460 in the fully fixed position.

FIG. 21 shows a cardiac prosthesis fixing device 470, or at least an inside view of a tubular element 474 that has been opened out. The tubular element has been opened out by cutting it open along axial cut lines 471. In the case of the cardiac prosthesis fixing device 470 the arms 472 with pins, which are not visible here, pointing towards the rear and the associated passages 473 are arranged in a sine-wave pattern. The reason for this is so that in the case of a valve annulus of sine-wave shape the arms 472 with pins are able to follow the shape of said annulus and all pins are thus able to penetrate the annulus tissue.

FIG. 22 shows, diagrammatically, a sectional view of yet a further variant of a cardiac prosthesis fixing device, specifically cardiac prosthesis fixing device 480 in which a valve prosthesis 485 consisting broadly of a ring 486 with valve cusps 489 has been mounted. The cardiac prosthesis fixing device 480 consists of a tubular element 481, a multiplicity of arms 482, each with a pin 483, arranged distributed over the periphery thereof and with one pin passage 484 per arm. In the so-called insertion position the arm 482 has been bent so far inwards that the pin 483 is located completely within the tubular body 481, in accordance with, for example, what is shown in FIG. 15A. In the case of the embodiment according to FIG. 22 it is possible to fix the cardiac prosthesis fixing device 480 at its destination, after it has been positioned at the destination, by swinging the pins 483 outwards at the same time as fitting the valve prosthesis 485. Viewed in accordance with FIG. 22, the valve prosthesis 485 is fed from the top, in accordance with the arrow, and introduced into the tubular body 481. During this operation the broadening 487 at the bottom will press on the arms 482 and swing the arms 482 with pins 483 outwards in order finally to pass beyond the transition between the arms 482 and pin 483, after which the arms 482 spring back inwards to snap behind the broadening. In this way the valve prosthesis 485 is fixed in the upward direction in the cardiac prosthesis fixing device 480. In the downward direction the cardiac prosthesis 485 is then fixed in the cardiac prosthesis fixing device 480 by the bottom stop 488, which can be a rim projecting inwards around the entire periphery or optionally can consist of a number of ridges projecting inwards. It should be clear that the valve prosthesis can optionally also be pulled from bottom to top, in which case at least the cardiac prosthesis fixing device 480 and ring element 486 have to be rotated through 180° about an axis transverse to the plane of the drawing.

For further explanation, FIG. 25 shows, diagrammatically, yet a further example of the use of a prosthesis fixing device according to the invention for fixing a vascular prosthesis. In this case use is made essentially of the same prosthesis fixing device as in FIG. 15, which prosthesis fixing device, in this case a vascular prosthesis fixing device, is for this reason indicated by 410 in FIG. 25. It should be clear that the prosthesis fixing device 410 in FIG. 25 can essentially be replaced by other prosthesis fixing devices according to the invention, such as, for example, shown in FIGS. 16A, 16B, 17A, 17B, 22, 23A, 23B, 24A and 24B. The vascular prosthesis 510 can be a natural or synthetic vascular prosthesis here. The vascular prosthesis 500 is provided at its ends with a relatively rigid ring 517 (comparable with ring 417 in FIG. 15), which ring 517 is provided with ridges 518 (comparable with the ridges 418 in FIG. 15) arranged distributed around the periphery. In accordance with the invention, the vascular prosthesis 110 can be fixed inside the circulatory system by positioning a prosthesis fixing device 410, with arms provided with pins, at each of the ends of the vascular prosthesis in the circulatory system and then fixing these, for example by pushing the ring 517 into the tubular element of the prosthesis fixing device 410 and thus pushing the arms 411 with pins 412 outwards for anchoring.

Many more variants of the invention described above which fall within the scope of the clauses but are not shown in the drawing are possible and conceivable. For instance, the arms and pins, for example, do not have to have the same shape over the entire periphery of the tubular element. Specifically, this shape can vary over the periphery depending on the type of natural valve to be replaced. Consider, for example, the mitral valve and what has already been described about this in the abovementioned Netherlands Patent Application 1 012 150, which has not been previously published and has been incorporated in its entirety in this PCT application in the form of Section X.1. According to a further variant it is conceivable that the tubular element and the valve prosthesis, such as the outside ring thereof, form an integral, preassembled whole.

In general, everywhere in this application and in particular in Section X.2, cardiac prosthesis fixing device can be read in the broader sense as prosthesis fixing device, in particular vascular prosthesis fixing device.

SECTION 3.3

FIGS. 26-32 show particular embodiments of the subject of Section X.1, which particular embodiments are further developed in Section X.3.

FIG. 26 shows a fixing device which, for example, can be used as an anastomosis device for producing an ETS anastomosis. In this context FIGS. 26A, 26B show various stages in the production of the anastomosis.

FIGS. 26-30 and 32 each show details of longitudinal sectional views. Viewed in a plane transverse to the plane of the drawing, the fixing devices shown in these figures will have a ring-shaped cross-sectional profile, such as a circular, oval or ellipsoidal cross-section.

In FIG. 26, 601 indicates the vascular wall tissue that surrounds the passage in which the fixing device 600 is to be accommodated. This vascular wall tissue 601 can, for example, be the vascular wall tissue of an aorta, but can also be cardiac wall tissue. 602 indicates the blood vessel, usually referred to as the graft vessel, to be joined to vascular wall tissue 601. The graft vessel 602 is firmly attached to the inside of a ring or cylindrical element 604 by means of suturing or stitching 605. The graft vessel 602 can also be attached to 604 in some other way. Thus, for example, this fixing can take place by clamping by resilient inner fingers which are joined at the inside and the bottom to the tubular element 604, the graft vessel 602 being clamped between these interior fingers of the tubular element 604.

The fixing device 600, which is also referred to as an anastomosis device, comprises a tubular body 610, which can also be referred to as annular, with bottom fingers 609 and top fingers 608. The bottom and top fingers 609 and 608 have been bent from a radial extended position (comparable to the position shown in FIG. 26B) into an axial extended position, as is shown in FIG. 26A. The bottom fingers 609 and top fingers 608 are held in this axially extended position by a sleeve 603 fitted around anastomosis device 600. In FIG. 26A the graft vessel 602 and the connecting ring 604 attached thereto are also shown as located inside the sleeve 603. However, as should be clear, these do not have to be located inside the sleeve 603, although this can be an advantage. The sleeve 603, with the anastomosis device 600 inside it, is inserted through the passage 612 in the vascular wall tissue 601, it being possible for the passage 612 already to have been preformed or optionally to be formed by a sharp or pointed bottom cutting edge 611, which is not shown, of the sleeve. The sleeve 603 is inserted into the passage 612 until the tubular body 610 is located approximately at the level of the passage 612. The sleeve 603 can then be withdrawn in the direction of arrow T while restraining the anastomosis device 600. When the sleeve 603 has been withdrawn sufficiently far, first of all the bottom fingers 609 will spring radially outwards into the position shown in FIG. 26B and when the sleeve 603 has been further withdrawn the top fingers 608 will also spring into a radial first position shown in FIG. 26B. On springing radially outwards the fingers 609 and 608 will clamp the vascular wall tissue surrounding the passage. To reinforce the anchoring in the vascular wall tissue 601, the fingers 608 and 609 can also be provided with roughenings, pointed projections, etc. on the sides thereof which face one another in FIG. 26B and optionally can even be provided with projections which extend as far as the opposite finger and which therefore pierce completely through the vascular wall tissue 601.

The ring 604 can then be fixed in place in anastomosis device 600 by snapping home the annular groove 606 on the annular rib 607 of the anastomosis device 600. The join between the ring 604 and the anastomosis device 600 can optionally already have been produced prior to inserting the device in passage 602 or at least prior to withdrawing the sleeve 603 from the passage 612.

In the radial position shown in FIG. 26B the fingers 608 and 609 form an interrupted flange in the peripheral direction of the anastomosis device 600. However, it should be clear that these interrupted flanges can optionally also have been constructed as continuous flanges by providing bodies between the flange fingers 608 and 609, which bodies, in the position shown in FIG. 26A, have been folded inwards between the respective fingers.

FIG. 27 shows an anastomosis device 620 which is particularly suitable for ETE anastomoses. The anastomosis device 620 consists of a tubular body 630 with bottom fingers 629 and top fingers 628, which in their axially extended position, the so-called second position, shown in FIG. 27A, are surrounded by a sleeve 623 in order to be held in said second position. The tubular element is provided with suture passages, with the aid of which one of the blood vessels, that is to say blood vessel 622, has been fixed in place by means of a suture join 625. This will in general be carried out before placing the tubular element 630 with top fingers 628 and bottom fingers 629 in sleeve 623. The assembly comprising sleeve 623, blood vessel 622, tubular element 630 and bottom fingers 629 and top fingers 628 has been inserted in a second blood vessel 621, or the second blood vessel 621 has been slid over the sleeve 623. The sleeve 623 is then withdrawn in upward direction T from the second blood vessel 621, after which first of all the bottom fingers 629 can fold outwards in the radial direction and, with a sharp point, will pierce the wall of the second blood vessel 621 for anchoring, in order then, on further withdrawal of the sleeve, to allow the top fingers 628 to fold radially outwards in order, likewise with a sharp point, to pierce the wall of the blood vessel 621. Optionally, the ends of the fingers 628 and 629 protruding through the blood vessel wall 621 can then be further flattened against the outside of the blood vessel wall 621 in order to anchor even better therewith.

It should be clear that in the case of the anastomosis device in FIG. 26 as well, the blood vessel 602 can have been directly sutured to the tubular element 610 in a manner corresponding to that in FIG. 27, or, conversely, that in the case of the embodiment according to FIG. 27 use can also be made of a ring 604 which snap-fits by means of an annular groove 606 on a rib formed on the tubular element 630.

FIG. 28A shows an example of a fixing device in the form of an anastomosis device 640 for producing an STS anastomosis between two blood vessels 641 and 642 running alongside one another. The STS anastomosis device 640 consists of a tubular element 643, bottom fingers 644 and top fingers 645, which are accommodated in their entirety in a sleeve 646 in a position ready for fitting. The procedure for fitting the anastomosis device 640 essentially corresponds to that for anastomosis device 600 in FIG. 26. However, one difference is that the bottom fingers 644 and top fingers 645, which in the radial, first position shown in FIG. 28B together each form an interrupted flange extending in the peripheral direction of the tubular body 643, now clamp two vascular wall tissues 642 and 641 together one above the other, and hold these clamped to one another, rather than clamping a single vascular wall tissue. Although the STS anastomosis device 640 could be fed to the fixing point via one of the vessels 641 or 642, in FIG. 28 it has been elected to do this via an additional passage 647 made in one of the vessels, in this case the upper vessel 641, opposite the fixing point. This additional passage 647 must be closed off after fitting the STS anastomosis device 640 and removing the sleeve 646. This could possibly be effected by suturing the passage 647 in situ, but can also be effected by fitting an obturator prosthesis 650. The obturator prosthesis 650 can essentially be absolutely identical to the STS anastomosis device 640, with the proviso that the tubular element 643 will generally be shorter in the axial direction and that the STS anastomosis device 640 has an open passage on the inside, whilst the obturator prosthesis 650 will be completely closed within the tubular element 651 or will already have been completely closed by a plate-like element in advance. In this context it is optionally possible to accommodate the obturator prosthesis 650 with the STS anastomosis device 640 in the same sleeve 646 at the same time and to fix it at its destination by withdrawing the sleeve 646 even further after fixing the STS anastomosis device 640. However, it is also conceivable to fix the obturator prosthesis 650 in place only after the sleeve 646 has been completely removed. It is also conceivable that first of all the obturator prosthesis 650 is fixed in the passage 647 and only then is the sleeve 646, together with the STS anastomosis device 640, fed through the obturator prosthesis 650 to the fixing point for the STS anastomosis device. In such a situation prosthesis 650 then acts as a portal prosthesis.

The fixing prosthesis 650 could also be constructed as is indicated in more detail by the broken lines in FIG. 28. With this more detailed embodiment the top fingers 652 will assume a radial position and will preferably not be individual fingers but a flange which extends uninterrupted around the periphery of the tubular element 651. A raised ring 653, which can be provided internally or externally with screw thread for fixing to, for example, a cannula or working conduit, is present on said flange 652. As is further indicated by broken lines, the bottom fingers 654 will be in an extended position for fitting in the passage 647. They can be held in this extended position by means of a suture or ligature running round the extended arms 654, which suture or ligature can be removed after positioning the obturator prosthesis 650 in the passage 647 in order to cause the fingers 654 to spring into the radial position. The raised edge 653 can also be used for fixing an obturator cap on the obturator prosthesis 650. This obturator cap (not shown) will then preferably also be located in the passage enclosed by the tubular element 651 in order to prevent a space forming in which the blood is not flowing or remains stagnant. Specifically, this could give rise to undesired blood clotting phenomena. That side of such an obturator cap, which is not shown, which faces the inside of the vessel 641 will preferably have been covered with vascular wall tissue in order, as far as possible, to restrict contact of the blood with material foreign to the body.

FIG. 28C shows a further embodiment of an obturator prosthesis or portal prosthesis. As should be clear, a portal prosthesis will have to be closed after the medical intervention and will then act as an obturator prosthesis and for this reason can also be utilised directly as an obturator prosthesis if the portal function is not needed. The portal/obturator prosthesis shown in FIG. 28C is essentially identical to the portal/obturator prosthesis 650 shown in FIG. 28B, with the proviso that the threaded ring 653 indicated by broken lines in FIG. 28B is missing and that the fixing device in FIG. 28C is provided inside the tubular element with screw thread 655, into which a cap 660 provided with external screw thread 661 can be screwed tight. Although screw thread is to be preferred in connection with it being possible to remove the cap 660 again, it is also very well possible to make use of the snap-fit connection by means of an annular groove 606 and annular rib 607, shown in FIG. 26, or another coupling, such as a bayonet fitting.

For fixing, for example, vascular wall tissue to that side of cap 660 which faces the bloodstream, said cap is provided on this side with an annular rib with radial passages for suture. In FIG. 28C this annular rib with radial suture passages is indicated by broken lines and provided with reference numeral 662.

FIGS. 29A and B show a further variant of an STS anastomosis device, consisting of two parts, each of which is individually fixed in the side wall of a blood vessel in a manner corresponding to that outlined with reference to FIGS. 26 and 28. The position in which the two vessels have each been provided with one part, 670 and 680, respectively, of the anastomosis device is shown in FIG. 29A and the position where these parts 670 and 680 have been joined to one another is shown in FIG. 29B. 671 and 672 indicate the inner and the outer fingers, respectively, of the one anastomosis device 670, and 681 and 682 indicate the inner and the outer fingers, respectively, of the other anastomosis device 680. Anastomosis device 670 is provided with a body 673, formed on the tubular element, with a peripheral slit 674 on the inside, and the tubular element of anastomosis device 680 is provided with a body 683 with a peripheral rib 684, which may or may not be interrupted, on the outside. The peripheral slit 674 and peripheral rib 684 can together form a snap-fit joint, as shown in FIG. 29B.

FIG. 30 shows an ETE anastomosis device 690. The ETE anastomosis device 690 consists of a tubular element 695 with suture passages, with the aid of which a first blood vessel 697 can be sutured internally in the tubular element 695 by means of a suture join 694. The tubular element 695 has, at the bottom, bottom fingers 692, which display a curvature, and top fingers 691. In a position ready for insertion, both the bottom and the top fingers 692 and 691, respectively, are held in the axially extended, second position by means of a sleeve 693. Said sleeve 693 makes it possible to insert the entire assembly of sleeve 693, ETE anastomosis device 690 and blood vessel 697 already fixed therein beforehand into a second blood vessel 696, or to slide said blood vessel 696 over the sleeve 693. This position is shown in FIG. 30A. When the sleeve is withdrawn upwards in the direction of arrow T, first of all the bottom fingers 692 will move outwards in the radial direction and pierce the wall of blood vessel 696. On further withdrawal of the sleeve 693 in direction T the top fingers 691 will be released and will be able to spring downwards under the influence of the resilient force into the position shown in FIG. 30B. When the top arm 691 and bottom arm 692 are in line, viewed in the axial direction of the tubular element 695, the top fingers 691, if these are longer than the axial length of the bottom fingers 692, will have been provided with passages 698 for accommodating the ends of the bottom fingers 692. When the top fingers 691 and bottom fingers 692 are offset with respect to one another in the radial direction of the tubular element 695, the pointed ends of the bottom fingers 692 will then be able to pass precisely between two sprung-back top fingers 691.

FIG. 31 shows two further advantageous embodiments, in particular with regard to the shape of the sleeve to be used with the fixing device according to Section X.3. By way of example, the fixing device indicated in the sleeve according to FIG. 31A is indicated by 600, corresponding to the indication in FIG. 26. The other reference numerals relating to the fixing device 600 itself have been omitted. The sleeve 700 has an end cut off obliquely at an angle α at the end where the bottom fingers are located. The angle α will in general be 45° or more, but can also be in the range from 30° to 45°. With this arrangement the bottom edge 702 of the sleeve 700 in particular forms a cutting edge, to which end this edge will also have been made sharp. The vascular wall tissue can be pierced by the cutting edge in order to form a passage for fitting the fixing device or the passage in which the fixing device has to be fitted can be made larger. In particular, the end 701 of the sleeve 700 will have been made sharp for this purpose. FIG. 31B shows a further variant, in which the bottom fingers of the fixing device run correspondingly to the sloping edge 702 of the sleeve 700.

FIG. 32 shows a one-piece ETS anastomosis device 710 according to Section X.3 of the application. The ETS anastomosis device 710 consists of a tubular element 711 from which a tubular part 712 runs upwards, which tubular part 712 is able to accommodate a blood vessel 713 on the inside. The blood vessel 713 can be clamped against the tubular part 712 by means of spring fingers or flange parts 714 and optionally anchored between the tubular part 712 and the fingers 714 by means of pointed parts. The fingers 714 can be sprung into one direction of the tubular part 712 under the influence of a pretension present in the fingers 714, for example by using a memory metal, such as nitinol, or by using a mechanical spring tension, in which latter case a mechanical impediment will be removed. However, this can also take place under mechanical action by means of a force exerted externally on the fingers 714, such as by means of a balloon or an element to be forced between the fingers 714 in the direction of the arrow T. After the blood vessel 713 has been fixed between the tubular part 712 and the fingers 714, the bottom fingers 716 and top fingers 715 can be brought into an extended position and the assembly as a whole can be fitted in the sleeve 717. It is also conceivable that the anastomosis device 710 is first placed in the sleeve 717, that the blood vessel 713 is only then inserted between the tubular part 712 and fingers 714 (as shown in FIG. 32A), the fingers 714 are then pushed in the direction of the tubular part 712 (shown in FIG. 32B) and only then is the whole inserted in a passage 718 in a vessel wall in a manner corresponding to that described with reference to, inter alia, FIG. 26 and the sleeve 717 is withdrawn in the direction of arrow T. This then results in the manner already described above in the join shown in FIG. 32C.

SECTION 3.4

FIG. 33 shows a fixing device according to the first aspect of Section X.4 and specifically in particular a fixing device of this type for the production of an ETE anastomosis.

In FIG. 33 the fixing device is indicated in its entirety by 740. The fixing device 740 consists of a tubular element 747, which is not much more than a ring with suture passages for producing a suture join 742 to one end of a blood vessel 745. The tubular element 747 continues downwards in a cylindrical inner flange 741. The tubular body 747 and cylindrical inner flange 741 together form, as it were, one cylindrical body. At its top, the tubular element 747 has an outer flange in the form of outer flange fingers 743 which are arranged distributed around the periphery of the tubular element 747. The outer flange fingers 743 can assume a fixing position, shown in FIG. 33B, and can be bent, against a resilient force, from said fixing position into the position in which they are extended with respect to the inner flange 741, which position is shown in FIG. 33A, and can be held in said extended position by means of a sleeve 744. In the extended position with sleeve 744 around them, the outer flange fingers 743 are in the so-called fitting position, as shown in FIG. 33A. In this fitting position the assembly made up of blood vessel 745, previously sutured via suture join 742, inner flange 741 and sleeve 744 can be inserted in the end 746 of a further vessel. The sleeve 744 can then be pulled upwards in accordance with arrow T, after which the outer flange fingers 743 return to the position shown in FIG. 33B under the influence of the resilient force, in which latter position they, together with the inner flange 741, clamp the end 746 of the vessel.

FIG. 34 shows a variant of the fixing device as shown in FIG. 33, likewise corresponding to the first aspect of Section X.4. Therefore, the same reference numerals as in FIG. 33 have been used in FIG. 34 for parts which are otherwise identical. The difference between the embodiment according to FIG. 34 and that according to FIG. 33 lies in the fact that the sleeve (744 in FIG. 33) is missing and in that the fixing device, or at least the outer flange fingers 743 thereof, has/have been made from superelastic metal alloy or an alloy with shape memory. In the position shown in FIG. 34 the outer flange fingers 743 are in a so-called frozen position. The outer flange fingers 743 can be released from this frozen position by heating the outer flange fingers 743 and optionally the entire fixing device to above a certain temperature, for example 38-40° C. Instead of this the outer flange fingers 743 can be retained by means of a sleeve 748 with a beaded edge, shown by broken lines, even after they have bent outwards under a pretension. This sleeve can then be slid downwards in order to release the outer flange fingers and then removed upwards, downwards or, after cutting open axially, laterally.

FIG. 35 shows a further embodiment of a fixing device according to the first aspect of Section X.4, which fixing device is primarily intended for the production of an ETE anastomosis of ends of vessels. The vessels to be joined by their ends are indicated by 745 and 746. The fixing device 750 consists of a tubular body 753 which at the opposing ends of the tube continues in a first inner flange 751 and a second inner flange 752. The inner flanges 751 and 752 each form an essentially tubular body. Outer flange fingers 754 and 755, which as such are comparable with the outer flange fingers 743 in FIGS. 33 and 34, also extend from the tubular body 753. These outer flange fingers have been bent against an internal resilient force from a fixing position, shown in FIG. 35B, into the essentially radially outward-pointing fitting position shown in FIG. 35A. In the fitting position the outer flange fingers 754 and 755 are, as it were, located back to back. The outer flange fingers 754 and 755 are held in this back-to-back position by means of a U-shaped ring element 757 which is open towards the middle and extends in the peripheral direction of the tubular body 753. The outer flange fingers 754 and 755 are released by removing the ring element 757, for example by folding open inward-pointing parts thereof, or by cutting through this ring element in an axial direction and then removing it. Under the influence of the spring tension which has been generated by bending the outer flange fingers into the position shown in FIG. 35A, these flange fingers are then able to return to the position shown in FIG. 35B in order, together with the inner flanges 751 and 752, to clamp the end 745 or 746 of the vessel concerned.

FIG. 36 shows yet a further variant of the fixing device according to the first aspect of the Sections X.4. As far as the bottom half is concerned, FIG. 36 shows considerable correspondence with the embodiment according to FIG. 33. The difference between the embodiments according to FIG. 36 and the embodiment according to FIG. 33 lies mainly in the way in which the fixing to the top vessel end 745 is produced. For these reasons the reference numerals 741, 743, 744, 745, 746 and 747 from FIG. 33 have therefore been used again for essentially the same parts. Reference can therefore also be made to FIG. 33 for the discussion of the functioning of the parts 741, 743, 744 for fixing vessel end 746. As has been stated, the difference lies in the way in which vessel end 745, shown as the upper end in FIG. 36, is attached. Said upper vessel end 745 is fixed by clamping between an essentially rigid outer flange 761, which can be a tubular body closed in the peripheral direction, and an inner flange that can be sprung out into contact with the latter and preferably will have been made up of inner flange fingers 762. Before producing the join to vessel end 746, the inner flange fingers 762 can already have been bent into the fixing position shown in FIG. 36B by pushing an article, such as a ring or cylinder, in the direction of arrow T between the periphery spanned by the inner flange fingers 762. It is also conceivable to make the inner flange fingers 762 from a superelastic metal alloy or an alloy with shape memory which can be activated. As already discussed above, it is then possible to freeze the inner flange fingers 762 in their position shown in FIG. 36A and to release them from this position in order to return to their position shown in FIG. 36B. In this case as well the fixing to vessel end 745 can be produced before fixing to vessel end 746, but it is also conceivable first to produce the fixing to vessel end 746 and only thereafter the fixing to vessel end 745. Furthermore, it is also possible to fix the inner flange fingers 762 by means of a mechanical impediment, for example a sleeve with an outwardly beaded edge placed between them (compare 748, FIG. 34).

FIG. 37 shows a variant of the ETE anastomosis device according to FIG. 34. The same reference numerals as in FIG. 34 have been used for corresponding parts. FIG. 37A shows the ETE anastomosis device in a so-called fitting position and FIG. 37B shows the anastomosis device in a so-called fixing position. The difference compared with the embodiment according to FIG. 34 is mainly that the inner flange 741 is now also able to assume a fitting position, in which it runs in the direction of vessel end 746 to be fixed thereto. The inner flange 741 will preferably have been made up of a number of inner flange fingers 741 arranged distributed around the periphery of the tubular body 747. The mode of operation of the inner flange fingers 741 is essentially identical to that of the outer flange fingers 743. Both can have been made of a superelastic metal alloy or an alloy with shape memory which can be activated. Fixing to vessel end 745 will once again preferably take place in advance by means of a suture join 742. Vessel end 746 to be joined to vessel end 745 will then be inserted between the inner flange fingers 741 and outer flange fingers 743, which are open in a V-shape. The ETE anastomosis device 770 will then be heated to a suitable temperature, as a consequence of which the flange fingers move into the position shown in FIG. 37B, the fixing position. In the case of the embodiment according to FIG. 37 as well, mechanical impediments for the inner flange fingers and/or outer flange fingers are again possible, for example by making use of sleeves with beaded edges (see what has been stated in this regard with reference to FIG. 34 and FIG. 36).

FIG. 38 shows, as a variant of FIG. 37, a double embodiment, with which the two vessel ends, that is to say vessel end 745 and vessel end 746, are clamped between movable inner flange fingers 741 and outer flange fingers 743 in the case of vessel end 746 and inner flange fingers 781 and outer flange fingers 782 in the case of vessel end 745. The mode of operation of the inner flange fingers 781 and outer flange fingers 782 corresponds to that of the inner flange fingers 741 and outer flange fingers 743 described with reference to FIG. 37.

FIG. 39 shows an embodiment of a fixing device according to the second aspect of Section X.4. FIG. 39 shows a fixing device 800 which, as shown in FIG. 39, can be used to produce a so-called ETS anastomosis and also to produce a portal prosthesis for joining a cannula or working conduit to a hole made in vascular wall tissue, or even for producing a so-called obturator prosthesis.

The fixing device 800 consists of a tubular element 801 that delimits a passage 812, an outer flange 802, fixed to the tubular element 801, and an inner flange made up of inner flange segments 803. The inner flange segments are each mounted on an arm 804. The arms 804 with inner flange segments 803 attached thereto are arranged distributed around the periphery of the tubular element 801. The arms 804 are bent inwards by one end about a hinge axis 813, such that the inner flange segments 803 are located entirely within the periphery, in particular the inner periphery, of the tubular element 801. By exerting a force directed radially outwards on an arm, such an arm 804 can be bent towards the tubular element 801, the inner flange segment 803 attached to the arm 804 moving radially outwards in order to overlap the outer flange 802 (FIG. 39B). With this arrangement all arms 804 can be bent outwards essentially simultaneously by pressing an auxiliary element covering the passage 812 into the passage 812 in accordance with arrow W. In the case of an ETS anastomosis, such a tool can be an assembly part 809, for example a ring or tubular assembly part, fixed to the blood vessel 807 to be fixed at the end. The assembly part 809 shown in FIG. 39A is a tubular body to which a blood vessel 807, which is to be joined at the end, has been fixed, preferably beforehand, by means of suture joins 808. When fitting the fixing device 800 the latter will be placed with its outer flange 802 in contact with the vascular wall tissue 806 surrounding the passage 814. The arms 804 will then be bent into an axially extended position, for example by pushing the tubular assembly part 809, to which the blood vessel 807 has already been fixed beforehand, into the passage 812. The tubular assembly part 809 is provided with a peripheral groove 811 for anchoring in the tubular element 801 and the tubular element 801 is provided with a corresponding peripheral rib 805. As can be seen in FIG. 39B, the tubular assembly part 809 will be pushed into the tubular element until the rib 805 snaps into the peripheral groove 811. It is optionally conceivable to push the fingers 803 through passages made in the tubular element 801 to the outside, in which case the tubular element could then be lengthened.

FIGS. 40A and 40B show essentially the same fixing device 800 as in FIG. 39, but now used as fixing device for a cannula 816, working conduit or an obturator cap 815. Therefore, the same reference numerals have been used for identical parts. The way in which the fixing device 800 according to FIGS. 40A and 40B is positioned in a passage surrounded by the vascular tissue 806, which, for example, can be the wall of the blood vessel or the wall of the cardiac chamber, in essence does not have to differ from the way in which this can be carried out in the case of the embodiment according to FIG. 39. The cannula 816, the working conduit or the obturator cap 815 can in this respect take over the task of the cylindrical assembly part 809. Various medical aids, such as surgical instruments, can be fed into the circulatory system, such as a blood vessel or cardiac chamber, via the cannula or working conduit. The underside of the obturator cap 815 is preferably covered with vascular wall tissue 817 that can have been fixed to the cap 815 in various ways, for example in the manner described with reference to FIG. 28C. In connection with, in particular, the coupling and uncoupling of a cannula 816 or working conduit, it can be preferable to replace the snap-fit connection 805 by a screw thread connection, bayonet fitting or a connection which can be uncoupled and recoupled in some other way. In the course of time the vascular wall tissue 817 can grow together with the vascular wall tissue 806 between the arms 804 and inner flange segments 803.

FIG. 41 shows a further variant of the fixing device according to the second aspect of Section X.4 in three positions. This figure actually relates to two fixing devices, i.e. 820 and 821, which together form a pair. Considered individually, the fixing devices 820 and 821 are, as far as their mode of operation is concerned, essentially identical to the fixing device 800. 807 is the vascular wall tissue, surrounding the passage, to which the fixing device 821 is fixed and 806 is the vascular wall tissue, surrounding the passage, to which fixing device 820 is fixed. Corresponding to fixing device 800, the fixing devices 820 and 821 are both made up of a tubular element 825 that bears an outer flange 826 and, via arms 828 which are bendable about a hinge axis, bears inner flange segments 827. As already described with reference to FIG. 39, the fixing devices 820 and 821 will first be positioned with an outer flange 826 in contact with the vascular wall tissue concerned and a force directed radially outwards will then be exerted from the inside on the arms 828 in order to bring the inner flange segments 827 into the position shown in FIG. 41B. In the case of the fixing device 820 this can be effected by pressing in a tubular body 823, covered on the inside with vascular wall tissue 817, here and fixing by means of a snap-fit connection 824. In the case of fixing device 821 this can be effected by pressing fixing device 820 herein until a snap-fit connection 824 snaps home. An STS anastomosis, for example, can be produced in this way, as can be seen in FIG. 41C from the way in which the vascular wall tissue 806 and 807 is shown.

FIG. 42 shows a third aspect of the invention according to Section X.4. This figure relates to a fixing device for producing an ETE anastomosis between two vessels 851 and 852 to be joined end to end. The fixing device 850 consists of an inner tubular body 853 and an outer tubular body 854, as well as a clamping sleeve 855. The tubular body 853 is inserted in vessel end 851 and the tubular body 854 is then slid over vessel end 851, after which vessel end 851 is fixed to the tubular body 853 and tubular body 854 by means of a suture join 856. The tubular body 853 is then inserted in a vessel end 852. The clamping sleeve 855 is then slid downwards in accordance with arrow W. Clamping sleeve 855 will then press in the axial direction against the outward-pointing fingers 857. The outward-pointing fingers 857 have pins 858 at their free ends. On pushing the clamping sleeve 855 further, the fingers 857 will then go into an axially extended position and the pins 858 will penetrate into the vascular wall tissue 851. If holes 859 have been made in the inner tubular body 853 at the location of the pins 858, the pins 858 are able to pierce completely through the vascular wall tissue 852 and extend into the tubular body 853 and preferably not protrude into the interior of the tubular body 853. The hole 859 can optionally be a tie hole, in which case the pointed end of the pin 858 is able to curl back like a paper staple in order to anchor in the inside of the vessel wall tissue 852. The clamping sleeve 855 is held in place by a rib 860 formed thereon (or optionally a cavity formed therein) snapping home with a cavity 861 (or, if appropriate, rib) formed in the tubular body 854.

With regard to the embodiment according to FIG. 42 it is pointed out that when using materials which are soluble in the human body it is not absolutely essential to make use of the pins 858. These could optionally be omitted, in which case pure clamping of the vascular wall tissue 852 between a tubular body 853, acting as inner flange, and fingers 857, acting as outer flange, takes place.

With regard to FIG. 42 it should also be pointed out that the blood vessel 851 can also be fixed to the inside of 853, and 853 and 854 can then be integrated to give a one-piece whole. The suture join 856 can then be retained, but movable inner arms can then also be used.

FIG. 43 shows an embodiment of a fourth aspect of the invention according to Section X.4 in three positions. The embodiment concerned here is in particular a particular embodiment of the invention according to Section X.1 and X.2 of this Application. FIGS. 43 and 44 show, diagrammatically, a cross-section of a blood vessel 870 with a spirally wound device 70 according to FIG. 6, with flange fingers 72 and 73 (not indicated in FIG. 43) extended in the axial direction, therein. The flange fingers 72 and 73 are held in their axially extended position by means of a sleeve which has been axially cut open, extends over the fixing device 70 and likewise has been wound in spiral form, which sleeve as such is comparable with the sleeve 175 in, for example, FIG. 11. The assembly comprising 70 and 871 is held together in spiral form by a sleeve 872 which is located around it and which is preferably closed in the circumferential direction. The construction 70, 871 and 872 has the advantage that in this way the fixing device 70 can be fed through narrow conduits to its destination. Once it has arrived at the destination, the sleeve 872 can then be pulled away, after which the situation shown in FIG. 43B remains. If the sleeve 871, which has been cut through in the axial direction, is then removed by pulling it away in the longitudinal direction of the blood vessel 870, the bottom and top flange fingers 72 and 73 can then, in the manner discussed with reference to FIG. 11, come to lie around, for example, a valve annulus or, as is shown in FIG. 43C, pierce through the vascular wall tissue 871 in accordance with FIG. 14.

FIG. 44 shows a variant of FIG. 43, where the ring prosthesis used is not so much an open ring prosthesis 70 but a version thereof which is closed in the peripheral direction, indicated here by 875, or an animal or human donor heart valve prosthesis, as shown in FIG. 5. A sleeve 876, which in contrast to the sleeve 871 can now be closed in the peripheral direction, runs over fixing device 875 at the outer periphery. Once again a surrounding sleeve 872 is provided in order to keep the whole in the compressed position. Once the device has reached its destination, the surrounding sleeve 872 can be removed, after which the position shown in FIG. 44B results. The sleeve 876 can then be removed, after which the position shown in FIG. 44C results. As should be clear, FIGS. 44B and 44C are very similar to FIGS. 43B and 43C, respectively. The main difference is that the fixing device 875 and the sleeve 876 are closed in the peripheral direction.

With reference to the fixing device 410 in FIG. 15 and FIG. 25 or one of the other fixing devices 420, 430, 440, 450, 460, 470, 480, 490 or 500 in Section X.2, or one of the other fixing devices in Sections X.3 or X.4, including the fifth and sixth aspect according to Section X.4, to be mentioned below, it is also pointed out that, if the respective tubular element has an axial cut-through in accordance with FIG. 6, these can also be wound into a spiral or, even without such an axial cut-through, can be compressed into a shape as shown in FIGS. 44, 45 and 46. Once the device is in position, the arms with pins can then be driven outwards, optionally with the aid of a balloon, or it is even conceivable that said arms with pins are held in an inward-pointing pretensioned position by a sleeve 871 or 876 or that they are made of a metal alloy which can be brought into a pretensioned frozen position.

FIG. 45 shows a variant of FIG. 43, where the fixing device 875 is held pinched together in sleeve 876.

FIG. 46 shows, as a variant to FIG. 44, an embodiment with which the fixing device 875 and sleeve 876 have been compressed into a star shape.

FIGS. 47 and 48 show a fifth aspect of the inventions according to Section X.4. This fifth aspect relates to a particular embodiment of the invention according to Section X.1 and Section X.2. What it comes down to is that the tubular or tube-shaped element is made up of segments and can thus be fed in a compressed or optionally ribbon-shaped position to the destination. At the destination the ring position of the tubular element can be restored, for example by placing a segment 880 in contact with the surrounding vascular wall tissue and engaging in the tissue with this segment. This engagement into the tissue can be effected by means of pins which pierce the vascular wall tissue, but also by means of clamping between flanges or at least flange segments. In the embodiment according to FIG. 47 the segments 880 are held together by means of a draw cord or tensioning wire 881. By pulling on the draw cord or tensioning wire 881 the segments 880 automatically come closer together in the form of a ring. Pulling on draw cord or tensioning wire 881 can optionally take place after the segments 880 have been anchored to the surrounding vascular wall tissue. If the passage in the surrounding vascular wall tissue is wider than the diameter of the ring of segments 880 shown in FIG. 47B, it is then possible to narrow the passage through the circulatory system in this way by pulling on the draw cord or tensioning wire 881. This can be of very great benefit in the case of so-called ring prostheses. Ring prostheses are prostheses which are used to reduce the size of the passage in a heart valve in connection with a heart valve that is leaking as a consequence of vessel widening.

The embodiment according to FIG. 48 differs from that according to FIG. 47 essentially in that use is made not of a draw cord or tensioning wire but of connecting wires 891 positioned between the segments 890. These are always individual connecting wires 891. These connecting wires can, for example, have been made of a superelastic metal alloy or of a metal alloy with shape memory, such as, for example, nitinol. The advantage of connecting wires 891 made of such a material is that instead of pulling on the draw cord 881 it can suffice to heat the connecting wires 891 to above a certain temperature, after which the connecting wires 891 will return from a frozen, extended position into a shortened position and thus be able to reduce the ring of segments 890 to the smaller diameter shown by broken lines in FIG. 48B. This reducing of the diameter can take place after the segments 890 have been joined to the surrounding vascular wall tissue or at least have been anchored herein. In this way a constriction of the circulatory system at the location of the fixing device can again be achieved. With regard to the mode of action of connecting wires 891 made from a superelastic metal alloy or a metal alloy with shape memory, which has been outlined here, reference can be made to, for example, orthodontics, where such wires are also used for exerting forces on teeth to correct the position thereof. In orthodontics as well the wires are then usually first put in place in order then to be heated to above a specific temperature, so that they shorten or shrink and start to exert the desired tensile force on the teeth.

With reference to FIGS. 49 and 50, which show embodiments according to the sixth aspect of Section X.4, it is also possible to make use of individual elements 900 and 910, which, for example, are joined to one another by means of memory metal or other elastic materials. Each element individually contains pins 901 and 911 which have been bent inwards and which can be introduced radially through openings 902 and 912 in the elements 900 and 910 (see FIGS. 49B and 50A), either by direct exertion of force from the inside or by means of the memory function of the pins. This radial movement is temporarily counteracted by impediments 903 on the inside or outside of the elements 900 and 910, which impediments prevent the pins 901 and 911 being able to emerge through the openings 902 and 912. Said elements 900 and 910 can be mounted on, for example, a balloon or expandable auxiliary instrument which, for example, is placed in a sleeve and is brought into place in compressed form via a narrow access path. After expanding the balloon or the auxiliary instrument, the elements 900 and 910 are brought into contact with the widened valve annulus. After removing an internal or external impediment 903, the pins 901 and 911 located inside are pressed in pairs, or all at the same time, radially through the openings 902 in the elements into the surrounding tissue. After decompression of the balloon or the auxiliary instrument, the elements assume their pre-programmed mutual spacing by means of the elastic connecting means located between them and in doing so will constrict the valve opening. In the case of a mitral valve ring the elements 900 and 910 will usually consist of a fairly straight larger section along the inter-atrial septum, with smaller elements constructed symmetrically in a sort of bean shape. In the case of an aortic valve ring, a circular form can suffice, which will consist of three or multiples of three elements. The impediments can be projections 903 arranged on a strip 904. This has the advantage that multiple impediments are removed at the same time when the strip 904 is pulled away.

FIG. 51 shows three embodiments of a seventh aspect of Section X.4. This seventh aspect is a further development of what has already been described in Section X.2. What is concerned here is in each case one ring or tubular element 930 with a multiplicity of pins 931, fixed to arms, distributed over the periphery, which pins 931, in accordance with the subject of Section X.2, are able, after the removal of an impediment 932 or 933 or 934, to move into a position in which they point radially outwards and in doing so to penetrate or pierce the surrounding vascular wall tissue. With this arrangement, in the position ready for fitting, the pins 931, fixed to arms, are permanently under spring tension against the impediment 932, 933 or 934. The impediment can be a sleeve-shaped body 932 that is located inside the tubular body 930. The impediment can also be a sleeve-shaped body 933 that is located in contact with the outside of the tubular body 930. According to FIG. 51C, the impediment is a securing pin 934, which has been inserted through two passages 935 and 936, which passages 935 and 936 have been made in the pin and, respectively, the arm of the assembly 931. Such impediments, for pins 931, which are located entirely or partially in the (hollow) wall of the tubular element are not shown.

FIG. 52 shows, as the eighth aspect of Section X.4, a further development of the subject of Section X.3. What is concerned here is a fixing device 940 for fixing in a passage 942 surrounded by vascular wall tissue 941. The fixing device 940 consists of a ring or tubular element 943 on which sloping, top flange fingers 944 are provided at the top and sloping bottom flange fingers 945 are provided at the bottom. The flange fingers 945 and 944 are here in a sloping position in order to make it possible to join, for example, another vessel or cannula to the vascular wall tissue 941, which, for example, can be a small vein, at an oblique angle of 45° or less. The bottom flange fingers 945 and top flange fingers 944 are held in a circumferential plane determined by the sleeve 946, which is likewise sloping, and, as should be clear, can in this way be fed obliquely through the passage 942. If the sleeve 946 is now pulled away in the direction according to arrow S, first of all the bottom flange fingers 945 will spring into contact with the bottom of the vascular wall tissue 941 under the influence of a spring tension and then the top flange fingers 944 will spring against the top of the vascular wall tissue 941. By choosing suitable oblique positions for the bottom flange fingers 945 and top flange fingers 944, a uniform distribution of flange fingers around the periphery of the passage 942 can be achieved, which is advantageous for good fixing.

FIG. 53 shows yet a ninth aspect of the subject of Section X.4, which in fact is once again a further development of the subject of Section X.3. What is concerned here is a sleeve 950 arranged around a guide wire 951. In this way by first feeding the guide wire 951 into the body, the sleeve 950 can then be guided along said guide wire to a specific destination, such as the position where, for example, a fixing device 960 has to be fixed in a passage surrounded by vascular wall tissue. The sleeve 950 has a pointed end to facilitate guiding over the guide wire 951. Such a pointed end can comprise a multiplicity of triangle-like elements 964, which are held together in a pointed shape (in FIG. 53 drawn only over a short distance in the longitudinal direction of the sleeve). The fixing device 960 can be provided relatively far away from the pointed end of the sleeve 950 in a cylindrical section of the sleeve 950, it being possible, for example, for the sleeve 950 to assume a curved shape at the end in order, for example, partially to follow the shape and form of the destination vessel, with or without the guide wire therein. However, this is by far from always being practical. For this reason the eighth aspect provides for the fixing device 960 to be located entirely or, as shown, partially in the pointed end of the sleeve 950. The fixing device 960 consists of a tubular or annular element 961 with top flange fingers 962 and bottom flange fingers 963 running in a cylindrical pattern mounted thereon, which flange fingers follow the tapering wall elements 964 of the pointed end of the sleeve 950. It should be clear that the fixing device 960 can optionally have been inserted more deeply into the pointed end or, optionally, can be located entirely in the pointed end, in which case the top flange fingers 962 could then project somewhat outwards, lying as it were in the extension of the bottom flange fingers 963. A further ring 965 is provided on the outside around the sleeve 950, and in this case also around the top flange fingers 962, in order to hold the multiplicity of triangular elements 964 together, preferably some distance away from the pointed end. Said ring 965 can also consist of an additional outer sleeve, which can be removed in its entirety or in parts. It should also be clear that the assembly shown in FIG. 53 can also be modified in order to be able to be connected arriving at an angle, corresponding to what is shown in FIG. 52. The top flange fingers 962 can then form essentially the same pattern as the top flange fingers 944 in FIG. 52 and the bottom flange fingers 963 will, if the fixing device 960 is located with the bottom flange fingers 963 within the pointed end 964 of sleeve 950, not only have a sloping position but will also taper.

The invention claimed is:

1. An implantable cardiac ring prosthesis for reducing the size of an annulus of a heart valve, said cardiac ring prosthesis comprising:
 a ring shaped element which is elastically contractile under influence of a resilient force for radially contracting the ring shaped element from an expanded, wide condition to a narrow condition to narrow said annulus,
 wherein the ring shaped element comprises a plurality of discrete ring segments, an individual connecting wire between each adjacent ring segment joining together the ring segments, and pins provided on the circumference of the ring segments for anchoring each ring segment to said annulus,
 wherein said connecting wires are elastically contractile in a circumferential direction of the ring shaped element for radially contracting the ring shaped element from said expanded, wide condition to said narrow condition,
 wherein the connecting wires are made from a shape memory metal,
 wherein the ring shaped element is compressible to a compressed condition smaller than the narrow condition for feeding and positioning said ring shaped element within said annulus,
 wherein the ring shaped element is expandable into said expanded, wide condition for bringing the ring shaped element into contact with the vascular wall tissue surrounding the annulus,
 wherein each pin is radially movable for anchoring each ring segment to said vascular wall tissue surrounding the annulus therefore anchoring the implantable cardiac ring prosthesis to said annulus, and
 wherein the ring shaped element is elastically contractible to return to said narrow condition therefore narrowing said annulus.

2. The ring prosthesis according to claim 1, further comprising an expandable instrument for expanding said ring shaped element to said expanded, wide condition upon expansion of said instrument and for allowing the ring shaped element to elastically contract to said narrow condition upon removal of said instrument.

3. The ring prothesis according to claim 2, wherein the expandable instrument comprises a balloon which can be inflated for expansion of said instrument and deflated for removal of said instrument.

4. The ring prosthesis according to claim 1, wherein the ring shaped element comprises a super elastic metal alloy capable of returning the ring shaped element from said expanded, wide condition into said narrow condition upon heating the ring shaped element.

5. The ring prothesis according to claim 1, wherein the ring shaped element comprises a metal alloy with shape memory capable of returning the ring shaped element from said expanded, wide condition into said narrow condition upon heating the ring shaped element.

6. The ring prosthesis according to claim 1, wherein the ring shaped element is an open C-shaped ring, having an opening in its circumference.

7. The ring prosthesis according to claim 6, wherein the ring shaped element can be brought into a ribbon-shaped condition for delivery to said passage.

8. The ring prothesis according to claim 1, wherein the ring shaped element can be brought into a ribbon-shaped condition for delivery to said passage.

9. The ring prosthesis according to claim 1, wherein the ring shaped element is in compressed condition and placed in a sleeve to keep the ring shaped element in the compressed condition.

10. The ring prosthesis according to claim 1, wherein each pin is radially movable from an inwardly bent position, in which said pin lies, viewed in radial direction, entirely inside said ring shaped element, through an opening in said ring shaped element to an emerging position, in which the pin emerge through said opening at the radial outside of said ring shaped element.

11. The ring prosthesis according to claim 10, wherein the pins, when lying inside the ring shaped element, are in a pretensioned state pretensioned towards an emerging position.

12. The ring prosthesis according to claim 11, wherein the pins are frozen in said pretensioned state.

13. The ring prosthesis according to claim 10, further comprising removable impediments counteracting radial outward movement of said pins when in the inwardly bent position.

14. The ring prostheses according to claim 1, wherein said ring prosthesis is for a mitral heart valve.

15. The ring prosthesis according to claim 1, wherein said ring prosthesis is for an aortic valve and has a circular form.

16. The ring prosthesis according to claim 15, wherein said ring prosthesis has a sinusoidal form 17. The ring prosthesis according to claim 15, wherein said ring shaped element comprises three or a multiple of three said ring segments.

18. The ring prosthesis according to claim 1, wherein said ring prosthesis is for a tricusbid valve.

* * * * *